United States Patent
Lee et al.

(10) Patent No.: US 9,457,053 B2
(45) Date of Patent: Oct. 4, 2016

(54) METHODS OF DIFFERENTIATING STEM CELLS BY MODULATING MIR-124

(71) Applicant: Accelerated BioSciences Corp., Manhattan Beach, CA (US)

(72) Inventors: Jau-Nan Lee, Kaohsiung (TW); Tony Tung-Yin Lee, Yarrow Point, WA (US); Yuta Lee, Kaohsiung (TW)

(73) Assignee: ACCELERATED BIOSCIENCES CORP., Manhattan Beach, CA (US)

( * ) Notice: Subject to any disclaimer, the term of this patent is extended or adjusted under 35 U.S.C. 154(b) by 0 days.

(21) Appl. No.: 14/090,804

(22) Filed: Nov. 26, 2013

(65) Prior Publication Data

US 2014/0170118 A1 Jun. 19, 2014

Related U.S. Application Data

(60) Provisional application No. 61/732,162, filed on Nov. 30, 2012, provisional application No. 61/877,156, filed on Sep. 12, 2013.

(51) Int. Cl.
*C12N 5/073* (2010.01)
*A61K 35/39* (2015.01)
*G01N 33/50* (2006.01)

(52) U.S. Cl.
CPC ............. *A61K 35/39* (2013.01); *C12N 5/0605* (2013.01); *G01N 33/507* (2013.01); *G01N 33/5073* (2013.01); *C12N 2501/115* (2013.01); *C12N 2501/65* (2013.01)

(58) Field of Classification Search
CPC .................................................. C12N 5/0605
USPC ......................................................... 435/377
See application file for complete search history.

(56) References Cited

U.S. PATENT DOCUMENTS

| | | |
|---|---|---|
| 4,683,202 A | 7/1987 | Mullis |
| 5,384,261 A | 1/1995 | Winkler et al. |
| 5,445,934 A | 8/1995 | Fodor et al. |
| 5,677,195 A | 10/1997 | Winkler et al. |
| 5,708,153 A | 1/1998 | Dower et al. |
| 5,744,305 A | 4/1998 | Fodor et al. |
| 5,770,358 A | 6/1998 | Dower et al. |
| 5,770,722 A | 6/1998 | Lockhart et al. |
| 5,789,162 A | 8/1998 | Dower et al. |
| 5,800,992 A | 9/1998 | Fodor et al. |
| 5,854,033 A | 12/1998 | Lizardi |
| 5,874,219 A | 2/1999 | Rava et al. |
| 6,020,135 A | 2/2000 | Levine et al. |
| 6,033,860 A | 3/2000 | Lockhart et al. |
| 6,040,138 A | 3/2000 | Lockhart et al. |
| 6,040,193 A | 3/2000 | Winkler et al. |
| 6,330,349 B1 | 12/2001 | Hays et al. |
| 6,344,316 B1 | 2/2002 | Lockhart et al. |
| 6,630,349 B1 | 10/2003 | Rossant et al. |
| 7,432,104 B2 | 10/2008 | Mitalipova et al. |
| 7,510,876 B2 | 3/2009 | D'Amour et al. |
| 7,534,608 B2 | 5/2009 | Martinson et al. |
| 7,541,185 B2 | 6/2009 | D'Amour et al. |
| 7,642,091 B2 | 1/2010 | Lee et al. |
| 7,695,963 B2 | 4/2010 | Agulnick et al. |
| 7,695,965 B2 | 4/2010 | Martinson et al. |
| 7,704,738 B2 | 4/2010 | D'Amour et al. |
| 7,892,534 B2 | 2/2011 | Lee et al. |
| 8,071,562 B2 | 12/2011 | Bader et al. |
| 8,163,553 B2 | 4/2012 | Lee et al. |
| 8,247,229 B2 | 8/2012 | Odorico et al. |
| 8,497,120 B2 | 7/2013 | Lee et al. |
| 8,557,580 B2 | 10/2013 | Daigh et al. |
| 8,691,274 B2 | 4/2014 | Xu et al. |
| 8,691,974 B2 | 4/2014 | Gatenholm et al. |
| 9,335,322 B2 | 5/2016 | Lee et al. |
| 2003/0104616 A1 | 6/2003 | Parikh et al. |
| 2004/0072288 A1 | 4/2004 | Collas et al. |
| 2006/0062769 A1 | 3/2006 | Habener et al. |
| 2006/0211110 A1 | 9/2006 | Lee et al. |
| 2007/0026405 A1 | 2/2007 | Alitalo et al. |
| 2007/0128174 A1 | 6/2007 | Kleinsek et al. |
| 2009/0087417 A1 | 4/2009 | Arenas et al. |
| 2009/0208466 A1 | 8/2009 | Yoo et al. |
| 2009/0263361 A1 | 10/2009 | Lee et al. |
| 2009/0263849 A1 | 10/2009 | Sun et al. |
| 2011/0136162 A1 | 6/2011 | Sun et al. |
| 2011/0151560 A1 | 6/2011 | Xu |
| 2011/0165682 A1 | 7/2011 | Lee et al. |
| 2011/0188728 A1 | 8/2011 | Sammak et al. |
| 2011/0250688 A1 | 10/2011 | Hasan |

(Continued)

FOREIGN PATENT DOCUMENTS

| | | |
|---|---|---|
| EP | 2233566 A1 | 9/2010 |
| EP | 2679669 A1 | 1/2014 |

(Continued)

OTHER PUBLICATIONS

Haimovici et al. (1993, Biol. Reprod., vol. 49, pp. 124-130).*
D'Amour et al. (2006, Nature Biotechnology, vol. 24(11), pp. 1392-1401).*
International search report and written opinion dated Mar. 13, 2014 for PCT/US2013/072073.
Jiang, et al. In vitro derivation of functional insulin-producing cells from human embryonic stem cells. Cell Res. Apr. 2007;17(4):333-44.
Xu, et al. Activin, BMP and FGF pathways cooperate to promote endoderm and pancreatic lineage cell differentiation from human embryonic stem cells. Mech Dev. Sep.-Dec. 2011;128(7-10):412-27. doi: 10.1016/j.mod.2011.08.001. Epub Aug. 10, 2011.

(Continued)

*Primary Examiner* — Anoop Singh
*Assistant Examiner* — David A Montanari
(74) *Attorney, Agent, or Firm* — Wilson Sonsini Goodrich & Rosati

(57) ABSTRACT

Provided herein are methods of differentiating stem cells via modulating miR-124, and the differentiated cells thereby. Also provided herein are methods for the treatment of diseases using the differentiated cells.

14 Claims, 47 Drawing Sheets

(56) References Cited

U.S. PATENT DOCUMENTS

| | | |
|---|---|---|
| 2012/0089238 A1 | 4/2012 | Kang et al. |
| 2012/0116568 A1 | 5/2012 | Murphy et al. |
| 2012/0135878 A1 | 5/2012 | Lee et al. |
| 2012/0148550 A1 | 6/2012 | Brodie et al. |
| 2012/0190078 A1 | 7/2012 | Gatenholm et al. |
| 2012/0190730 A1 | 7/2012 | Michael |
| 2012/0277111 A1 | 11/2012 | Crabtree et al. |
| 2012/0328579 A1 | 12/2012 | Lee et al. |
| 2013/0004469 A1 | 1/2013 | Glazier et al. |
| 2013/0017564 A1 | 1/2013 | Guillemot et al. |
| 2013/0028872 A1 | 1/2013 | Bone et al. |
| 2013/0164339 A1 | 6/2013 | Murphy et al. |
| 2013/0304233 A1 | 11/2013 | Dean et al. |
| 2013/0337458 A1 | 12/2013 | Lee et al. |
| 2014/0012407 A1 | 1/2014 | Murphy et al. |
| 2014/0052285 A1 | 2/2014 | Butcher et al. |
| 2014/0093932 A1 | 4/2014 | Murphy et al. |
| 2014/0099709 A1 | 4/2014 | Presnell et al. |

FOREIGN PATENT DOCUMENTS

| | | |
|---|---|---|
| JP | 2009533056 A | 9/2009 |
| WO | WO-03050249 A2 | 6/2003 |
| WO | WO-2005030961 A1 | 4/2005 |
| WO | WO 2006/091766 A2 | 8/2006 |
| WO | WO 2010/096496 A2 | 8/2010 |
| WO | WO 2011/050476 A1 | 5/2011 |
| WO | WO 2011/054100 A1 | 5/2011 |
| WO | WO 2012/068170 A2 | 5/2012 |
| WO | WO-2012070014 A2 | 5/2012 |
| WO | WO-2012122105 A1 | 9/2012 |
| WO | WO-2013040087 A2 | 3/2013 |
| WO | WO-2013181375 A1 | 12/2013 |
| WO | WO-2014039427 A1 | 3/2014 |
| WO | WO 2014/085493 A1 | 6/2014 |

OTHER PUBLICATIONS

Alexiou, et al. miRGen 2.0: a database of microRNA genomic information and regulation. Nucleic Acids Res. Jan. 2010;38(Database issue):D137-41. doi: 10.1093/nar/gkp888. Epub Oct. 22, 2009.
Anderson. Human gene therapy. Science. May 8, 1992;256(5058):808-13.
Anneren, et al. The Srs family of tyrosine kinases is important for embryonic stem cell self-renewal. J Biol Chem. Jul. 23, 2004;279(30):31590-8. Epub May 7, 2004.
Arnit, et al. Clonally Derived Human Embryonic Stem Cell Lines Maintain Pluripotency and Proliferative Potential for Prolonged Periods of Culture, Developmental Biology 227,271-278 (2000).
Bain, et al. Embryonic stem cells express neuronal properties in vitro. Dev. Biol. 1995; 168:342-357.
Baroukh, et al. MicroRNA-124a regulates Foxa2 expression and intracellular signaling in pancreatic beta-cell lines. J Biol Chem. Jul. 6, 2007;282(27):19575-88. Epub Apr. 26, 2007.
Bernardo, et al. Biphasic induction of Pdxl in mouse and human embryonic stem cells can mimic development of pancreatic beta-cells. Stem Cells. Feb. 2009;27(2):341-51. doi: 10.1634/stemcells.2008-0310.
Bjorklund, et al. Embryonic stem cells develop into functional dopaminergic neurons after transplantation in a Parkinson rat model. Proc Natl Acad Sci U S A. Feb. 19, 2002;99(4):2344-9. Epub Jan. 8, 2002.
Borowiak. The new generation of beta-cells: replication, stem cell differentiation, and the role of small molecules. Rev Diabet Stud. 2010 Summer;7(2):93-104. doi: 10.1900/RDS.2010.7.93. Epub Aug. 10, 2010.
Burlison, et al. Pdx-1 and Ptfl a concurrently determine fate specification of pancreatic multipotent progenitor cells. Dev Biol. Apr. 1, 2008;316(1):74-86. doi: 10.1016/j.ydbio.2008.01.011. Epub Jan. 26, 2008.
Cavaleri, et al. Nanog: a new recruit to the embryonic stem cell orchestra. Cell. 2003; 113:551-552.
Chai, et al. FGF is an Essential Regulator of the Fifth Cell Division in Preimplantation Mouse Embryos, Development Biology, vol. 198, pp. 105-115 (1998).
Chambers, et al. Functional expression cloning of Nanog, a pluripotency sustaining factor in embryonic stem cells. Cell. 2003; 113:643-655.
Chambers, et al. Self-renewal of teratocarcinoma and embryonic stem cells. Oncogene. 2004; 23:7150-7160.
Chen, et al. Expression of leukemia inhibitory factor and its receptor is not altered in the decidua and chorionic villi of human anembryonic pregnancy. Hum Reprod. Jul. 2004;19(7):1647-54. Epub Jun. 4, 2004.
Cheng, et al. Human Adult Marrow Cells Support Prolonged Expansion of Human Embryonic Stem Cells in Culture, Stem Cells, vol. 21 pp. 131-142 (2003).
Chenn, et al. Regulation of cerebral cortical size by control of cell cycle exit in neural precursors. Science. 2002; 297:365-369.
Copp, A.J. Interaction between inner cell mass and trophectoderm of the mouse blastocyst, J. Embryol. Exp. Morph., vol. 51, pp. 109-120 (1979).
International Preliminary Report on Patentability mailed Nov. 23, 2007 in connection with PCT/US2006/006512.
International Search Report mailed Nov. 23, 2007 in connection with PCT/US2006/006512.
Written Opinion mailed Nov. 23, 2007 in connection with PCT/US2006/006512.
Cunliffe, et al. Switching on the notochord. Genes Dev. Jul. 1, 1999;1;13(13):1643-6.
D'Amour, et al. Efficient differentiation of human embryonic stem cells to definitive endoderm. Nat Biotechnol. Dec. 2005;23(12):1534-41. Epub Oct. 28, 2005.
Dunnett, et al. Cell therapy in Parkinson's disease—stop or go? Nat. Rev. Neurosci. 2001; 2:365-369.
Edghill, et al. Hepatocyte nuclear factor-1 beta mutations cause neonatal diabetes and intrauterine growth retardation: support for a critical role of HNF-1beta in human pancreatic development. Diabet Med. Dec. 2006;23(12):1301-6.
Episkopou. SOX2 functions in adult neural stem cells. Trends Neurosci. May 2005;28(5):219-21.
Freed, et al. Transplantation of embryonic dopamine neurons for severe Parkinson's disease. N. Engl. J. Med. 2001; 344:710-719.
Furuyama, et al. Continuous cell supply from a Sox9-expressing progenitor zone in adult liver, exocrine pancreas and intestine. Nat Genet. Jan. 2011;43(1):34-41. doi: 10.1038/ng.722. Epub Nov. 28, 2010.
Gerami-Naini, et al. Trophoblast Differentiation in Embryoid Bodies Derived from Human Embryonic Stem Cells, Endocrinology, vol. 145(4) p. 1517-1524 (2004).
Gotz. Glial cells generate neurons—master control within CNS regions: developmental perspectives on neural stem cells. Neuroscientist. 2003; 9:379-97.
Gradwohl, et al. neurogenin3 is required for the development of the four endocrine cell lineages of the pancreas. Proc Natl Acad Sci U S A. Feb. 15, 2000;97(4):1607-11.
Graphin-Botton, et al. Key events of pancreas formation are triggered in gut endoderm by ectopic expression of pancreatic regulatory genes. Genes Dev. Feb. 15, 2001;15(4):444-54.
Hart, et al. Mixll is required for axial mesendoderm morphogenesis and patterning in the murine embryo. Development. Aug. 2002;129(15):3597-608.
Hochedlinger, et al. Nuclear transplantation, embryonic stem cells, and the potential for cell therapy. N Engl J Med. Jul. 17, 2003;349(3):275-86.
Iancu, et al. Behavioral characterization of a unilateral 6-OHDA-lesion model of Parkinson's disease in mice, Behavioural Brain Research, vol. 162 pp. 1-10 (2005).
International search report and written opinion dated May 3, 2012 for PCT/US2011/060868.
Izzi, et al. Foxhl recruits Gsc to negatively regulate Mixll expression during early mouse development. EMBO J. Jul. 11, 2007;26(13):3132-43. Epub Jun. 14, 2007.

(56) References Cited

OTHER PUBLICATIONS

Kehler, et al. Oct. 4 is required for primordial germ cell survival, European Molecular Biology Organization reports, vol. 5 No. 1 1, pp. 1078-1083 (2004).

Keltz, et al. Modulation of leukemia inhibitory factor gene expression and protein biosynthesis in the human fallopian tube. Am J Obstet Gynecol. Dec. 1996;175(6):1611-9.

Kim, et al. Dopamine neurons derived from embryonic stem cells function in an animal model of Parkinson's disease. Nature. Jul. 4, 2002;418(6893):50-6. Epub Jun. 20, 2002.

Kimura, et al. Conditional loss of PTEN leads to testicular teratoma and enhances embryonic germ cell production. Development. 2003; 130:1691-1700.

Kroon, et al. Pancreatic endoderm derived from human embryonic stem cells generates glucose-responsive insulin-secreting cells in vivo. Nat Biotechnol. Apr. 2008;26(4):443-52. doi: 10.1038/nbt1393. Epub Feb. 20, 2008.

Kunath, et al. Trophoblast Stem Cells, Stem Cell Biology, pp. 267-287, (2001).

Kurie, et al. Retinoic acid stimulates the protein kinase C pathway before activation of its beta-nuclear receptor during human teratocarcinoma differentiation. Biochim Biophys Acta. 1993; 1179(2):203-7.

Lee, et al. Ectopic pregnancy-derived human trophoblastic stem cells regenerate dopaminergic nigrostriatal pathway to treat parkinsonian rats. PLoS One. 2012;7(12):e52491. doi: 10.1371/journal.pone.0052491. Epub Dec. 21, 2012.

Li, et al. Human embryonic stem cells possess immune-privileged properties. Stem Cells. 2004; 22:448-456.

Li, et al. Specification of motoneurons from human embryonic stem cells. Nat Biotechnol. Feb. 2005;23(2):215-21. Epub Jan. 30, 2005.

Liew. Generation of insulin-producing cells from pluripotent stem cells: from the selection of cell sources to the optimization of protocols. Rev Diabet Stud. 2010 Summer;7(2):82-92. doi: 10.1900/RDS.2010.7.82. Epub Aug. 10, 2010.

Lim, et al. Enforced expression of Mixl1 during mouse ES cell differentiation suppresses hematopoietic mesoderm and promotes endoderm formation. Stem Cells. Feb. 2009;27(2):363-74. doi: 10.1634/stemcells.2008-1008.

Lindvall, et al. Stem cell therapy for human neurodegenerative disorders—how to make it work. Nat Med. Jul. 2004;10 Suppl:S42-50.

Lovis, et al. Regulation of the expression of components of the exocytotic machinery of insulin-secreting cells by microRNAs. Biol Chem. Mar. 2008;389(3):305-12. doi: 10.1515/BC.2008.026.

Makeyev, et al. The MicroRNA miR-124 promotes neuronal differentiation by triggering brain-specific alternative pre-mRNA splicing. Mol Cell. Aug. 3, 2007;27(3):435-48.

Marson, et al. Connecting microRNA genes to the core transcriptional regulatory circuitry of embryonic stem cells. Cell. Aug. 8, 2008;134(3):521-33. doi: 10.1016/j.cell.2008.07.020.

Miller. Human gene therapy comes of age. Nature. Jun. 11, 1992;357(6378):455-60.

Mohn, et al. Mouse Mix gene is activated early during differentiation of ES and F9 stem cells and induces endoderm in frog embryos. Dev Dyn. Mar. 2003;226(3):446-59.

Mulligan. The basic science of gene therapy. Science. May 14, 1993;260(5110):926-32.

Myers, et al. Functional characterization of the brain-specific FGF-1 promoter, FGF-1.B. J. Biol. Chem. 1995; 270:8257-8266.

Nichols, et al. Formation of Pluripotent Stem Cells in the Mammalian Embryo Depends on the POU Transcription Factor Oct. 4, Cell, vol. 95, pp. 379-391 (1998).

Niwa, et al. Interaction between Oct. 3/4 and Cdx2 determines trophectoderm differentiation. Cell. Dec. 2, 2005;123(5):917-29.

Office action dated Aug. 18, 2009 for U.S. Appl. No. 11/361,588.

Office action dated Nov. 25, 2008 for U.S. Appl. No. 11/361,588.

Office action dated Dec. 18, 2012 for U.S. Appl. No. 13/415,595.

Offield, et al. PDX-1 is required for pancreatic outgrowth and differentiation of the rostral duodenum. Development. Mar. 1996;122(3):983-95.

Panicker, et al. Stem cells and neurogenesis. Stem Cell Biology. 2001; 399-438.

Pauli, et al. Non-coding RNAs as regulators of embryogenesis. Nat Rev Genet. Feb. 2011;12(2):136-49. doi: 10.1038/nrg2904.

Pereira, et al. Brachyury and related Tbx proteins interact with the Mixl1 homeodomain protein and negatively regulate Mixl1 transcriptional activity. PLoS One. 2011;6(12):e28394. doi: 10.1371/journal.pone.0028394. Epub Dec. 2, 2011.

Pereira, et al. The Mix family of homeobox genes—key regulators of mesendoderm formation during vertebrate development. Dev Biol. Jul. 15, 2012;367(2):163-77. doi: 10.1016/j.ydbio.2012.04.033. Epub May 8, 2012.

Qi, et al. BMP4 supports self-renewal of embryonic stem cells by inhibiting mitogen-activated protein kinase pathways. Proc Natl Acad Sci U S A. Apr. 20, 2004;101(16):6027-32. Epub Apr. 9, 2004.

Qureshi, et al. Anti-DNA antibodies cross-reacting with laminin inhibit trophoblast attachment and migration: implications for recurrent pregnancy loss in SLE patients. Am J Reprod Immunol. Sep. 2000;44(3):136-42.

Rajasethupathy, et al. Characterization of small RNAs in Aplysia reveals a role for miR-124 in constraining synaptic plasticity through CREB. Neuron. Sep. 24, 2009;63(6):803-17. doi: 10.1016/j.neuron.2009.05.029.

Reubinoff, et al. Neural progenitors from human embryonic stem cells. Nat. Biotech. 2001; 19:1134-1140.

Rossant, et al. Effect of culture conditions on diploid to giant-cell transformation in postimplantation mouse trophoblast, J. Embryol. exp. Morph., vol. 62, pp. 217-227 (1981).

Rossant, J. Stem Cells from the Mammalian Blastocyst, Stem Cells, vol. 19, pp. 477-482 (2001).

Schisler, et al. Stimulation of human and rat islet beta-cell proliferation with retention of function by the homeodomain transcription factor Nkx6.1. Mol Cell Biol. May 2008;28(10):3465-76. doi: 10.1128/MCB.01791-07. Epub Mar. 17, 2008.

Schulz, et al. Human embryonic stem cells as models for trophoblast differentiation. Placenta. Mar. 2008;29 Suppl A:S10-6.

Seymour, et al. SOX9 is required for maintenance of the pancreatic progenitor cell pool. Proc Natl Acad Sci U S A. Feb. 6, 2007;104(6):1865-70. Epub Jan. 31, 2007.

Shamblott, et al. Derivation of pluripotent stem cells from cultured human primordial germ cells, Proc. Natl. Acad. Sci. USA, vol. 95, pp. 13726-13731 (1998).

Shamblott, et al. Human embryonic germ cell derivatives express a broad range of developmentally distinct markers and proliferate extensively in vitro, Proc. Natl. Acad. Sci., vol. 98 No. 1, pp. 113-118 (2001).

Shiraki, et al. Guided differentiation of embryonic stem cells into Pdx1-expressing regional-specific definitive endoderm. Stem Cells. Apr. 2008;26(4):874-85. doi: 10.1634/stemcells.2007-0608. Epub Jan. 31, 2008.

Silva, et al. Capturing pluripotency. Cell. Feb. 22, 2008;132(4):532-6. doi: 10.1016/j.cell.2008.02.006.

Singh, et al. Identification of human brain tumour initiating cells. Nature. 2004; 432:396-401.

Smith, et al. Inhibition of pluripotential embryonic stem cell differentiation by purified polypeptides. Nature. 1998; 336:688-690.

Smith, et al. Placental involvement in congenital neuroblastoma. J. Clin. Pathol. 1981; 34:785-789.

Sneddon, et al. Self-renewal of embryonic-stem-cell-derived progenitors by organ-matched mesenchyme. Nature. Nov. 29, 2012;491(7426):765-8. doi: 10.1038/nature11463. Epub Oct. 7, 2012.

Song, et al. Astroglia induce neurogenesis from adult neural stem cells. Nature. 2002; 417:39-44.

Spence, et al. Sox17 regulates organ lineage segregation of ventral foregut progenitor cells. Dev Cell. Jul. 2009;17(1):62-74. doi: 10.1016/j.devcel.2009.05.012.

Tam, et al. Early endoderm development in vertebrates: lineage differentiation and morphogenetic function. Curr Opin Genet Dev. Aug. 2003;13(4):393-400.

(56) References Cited

OTHER PUBLICATIONS

Tam, et al. Sequential allocation and global pattern of movement of the definitive endoderm in the mouse embryo during gastrulation. Development. Jan. 2007;134(2):251-60. Epub Dec. 6, 2006.
Thomson, et al. Embroynic Stem Cell Lines Derived from Human Blastocysts, Science, vol. 282 pp. 1145-1147 (1998).
Tropepe. Direct neural fate specification from embryonic stem cells: a primitive mammalian neural stem cell stage acquired through a default mechanism. Neuron. 2001; 30:65-78.
Tsai, et al. Involvement of replicative polymerases, Tel1p, Mec1p, Cdc13p, and the Ku complex in telomere-telomere recombination. Mol. Cell. Biol. 2002; 22:5679-5687.
Van Brunt. Molecular farming: Transgenic animals as bio-reactors. Biotechnology. 1988; 6(10):1149-1154.
Wagner, et al. Induction of a midbrain dopaminergic phenotype in Nurr1—overexpressing neural stem cells by type 1 astrocytes. Nat. Biotechnol. 1999; 17:653-659.
Wells, et al. Vertebrate endoderm development. Annu Rev Cell Dev Biol. 1999;15:393-410.
Wichterle, et al. Directed differentiation of embryonic stem cells into motor neurons. Cell. 2002; 110:385-397.
Wilcox. Insulin and insulin resistance. Clin Biochem Rev. May 2005;26(2):19-39.
Williams, et al Myeloid leukemia inhibitory factor maintains the developmen- tal potential of embryonic stem cells. Nature. 1998; 336:684-687.
Wu, et al. Suppression of hydroxyl radical formation and protection of nigral neurons by l-deprenyl (selegiline). Ann. N. Y. Acad. Sci. 1996; 786:379-389.
Xi, et al. A poised chromatin platform for TGF-βaccess to master regulators. Cell. Dec. 23, 2011;147(7):1511-24. doi: 10.1016/j.cell.2011.11.032.
Xu, et al. BMP4 initiates human embryonic stem cell differentiation to trophoblast. Nat Biotechnol. Dec. 2002;20(12):1261-4.
Xu, R. In vitro induction of trophoblast from human embryonic stem cells. Methods Mol Med. 2006;121:189-202.
Yan, et al. Retinoic acid promotes differentiation of trophoblast stem cells to a giant cell fate. Dev. Biol. 2001; 235:422-432.
Ying, et al. BMP induction of Id proteins suppresses differentiation and sustains embryonic stem cell self-renewal in collaboration with STAT3. Cell. 2003; 115:281-292.
Yu, et al. Progress towards gene therapy for HIV infection. Gene Ther. Jan. 1994;1(1):13-26. Abstract only.
Adjaye, et al. Primary differentiation in the human blastocyst: comparative molecular portraits of inner cell mass and trophectoderm cells. Stem Cells. Nov.-Dec. 2005;23(10):1514-25. Epub Aug. 4, 2005.
Ameri, et al. FGF2 specifies hESC-derived definitive endoderm into foregut/midgut cell lineages in a concentration-dependent manner. Stem Cells. Jan. 2010;28(1):45-56. doi: 10.1002/stem.249.
Barral, et al. Roles of molecular chaperones in protein misfolding diseases. Seminars in Cell & Developmental Biology. 2004; 15:17-29.
Bavaresco, et al. The role of ecto-5'-nucleotidase/CD73 in glioma cell line proliferation. Mol Cell Biochem. Dec. 2008;319(1-2):61-8. Epub Jul. 18, 2008.
Bi, et al. Pre-activation of retinoid signaling facilitates neuronal differentiation of mesenchymal stem cells. Dev Growth Differ. Jun. 2010;52(5):419-31. doi: 10.1111/j.1440-169X.2010.01182.x.
Boiani, et al. Regulatory networks in embryo-derived pluripotent stem cells. Nature Rev. Mol. Cell Biol. 2005; 6:872-884.
Chen, et al. Promotion of feeder-independent self-renewal of embryonic stem cells by retinol (vitamin A). Stem Cells. Jul. 2008;26(7):1858-64. Epub Apr. 24, 2008.
Chiba, et al. Noggin and basic FGF were implicated in forebrain fate and caudal fate, respectively, of the neural tube-like structures emerging in mouse ES cell culture. Exp Brain Res. May 2005;163(1):86-99. Epub Feb. 10, 2005.
Coutinho, et al. An Evolving Hierarchical Family Classification for Glycosyltransferases. J. Mol. Biol. 2003; 328:307-317.

Gage, et al. Neural stem cells: generating and regenerating the brain. Neuron. Oct. 30, 2013;80(3):588-601. doi: 10.1016/j.neuron.2013.10.037.
Goncalves, et al. Sequential RARbeta and alpha signalling in vivo can induce adult forebrain neural progenitor cells to differentiate into neurons through Shh and FGF signalling pathways. Dev Biol. Feb. 15, 2009;326(2):305-13. doi: 10.1016/j.ydbio.2008.11.018. Epub Dec. 7, 2008.
Goncalves, et al. Timing of the retinoid-signalling pathway determines the expression of neuronal markers in neural progenitor cells. Dev Biol. Feb. 1, 2005;278(1):60-70.
He, et al. Lymphoid enhancer factor 1-mediated Wnt signaling promotes the initiation of trophoblast lineage differentiation in mouse embryonic stem cells. Stem Cells. Apr. 2008;26(4):842-9. Epub Jan. 10, 2008.
Hori, et al. Neural progenitor cells lack immunogenicity and resist destruction as allografts. Stem Cells. 2003;21(4):405-16.
Ilancheran, et al. Human fetal membranes: a source of stem cells for tissue regeneration and repair? Placenta. Jan. 2009;30(1):2-10. Epub Nov. 7, 2008.
Jacobs, et al. Retinoic acid is required early during adult neurogenesis in the dentate gyms. Proc Natl Acad Sci USA. Mar. 7, 2006;103(10):3902-7. Epub Feb. 27, 2006.
Kennea, et al. Neural stem cells. J Pathol. Jul. 2002;197(4):536-50.
Kornblum, et al. Introduction to neural stem cells. Stroke. Feb. 2007;38(2 Suppl): 810-6.
Lindvall, et al. Stem cells for the treatment of neurological disorders. Nature. 2006; 441:1094-1096.
Lu, et al. All-trans retinoic acid promotes neural lineage entry by pluripotent embryonic stem cells via multiple pathways. BMC Cell Biol. 2009; 10:57.
Maden. Retinoic acid in the development, regeneration and maintenance of the nervous system. Nat. Rev. Neuroscience. 2007; 8:755-765.
Martin-Ibanez, et al. Interplay of leukemia inhibitory factor and retinoic acid on neural differentiation of mouse embryonic stem cells. J. Neuron. Res. 2007; 85:2686-2710.
Napoli, et al. Microglial clearance function in health and disease. Neuroscience. Feb. 6, 2009;158(3):1030-8. Epub Jul. 1, 2008.
Niwa. Development. How is pluripotency determined and maintained? Development. Feb. 2007;134(4):635-46. Epub Jan. 10, 2007.
Office action dated Mar. 3, 2014 for U.S. Appl. No. 13/909,469.
Office action dated Jul. 30, 2014 for U.S. Appl. No. 13/296,876.
Office action dated Aug. 4, 2014 for U.S. Appl. No. 13/909,469.
Okano, et al. Neural stem cells: involvement in adult neurogenesis and CNS repair. Phil. Trans. R. Soc. B. 2008; 363:2111-2122. doi:10.1098/rstb.2008.2264.
Parolini, et al. Concise review: isolation and characterization of cells from human term placenta: outcome of the first international Workshop on Placenta Derived Stem Cells. Stem Cells. Feb. 2008;26(2):300-11. Epub Nov. 1, 2007.
Phillips, et al. Cdx2 as a marker of epithelial intestinal differentiation in the esophagus. Am J Surg Pathol. Nov. 2003;27(11):1442-7.
Portmann-Lanz, et al. Placental mesenchymal stem cells as potential autologous graft for pre- and perinatal neuroregeneration. Am J Obstet Gynecol. Mar. 2006;194(3):664-73.
Roy, et al. Functional engraftment of human ES cell-derived dopaminergic neurons enriched by coculture with telomerase-immortalized midbrain astrocytes. Nat Med. Nov. 2006;12(11):1259-68. Epub Oct. 22, 2006.
Schwartz, et al. Differentiation of Neural Lineage Cells from Human Pluripotent Stem Cells. Methods. Jun. 2008; 45(2):142-158. doi:10.1016/j.ymeth.2008.03.007.
Seaberg, et al. Stem and progenitor cells: the premature desertion of rigorous definitions. Trends Neurosci. Mar. 2003;26(3):125-31.
Surani, et al. Genetic and epigenetic regulators of pluripotency. Cell. 2007; 128:747-762.
Swijenburg, et al. Immunosuppressive therapy mitigates immunological rejection of human embryonic stem cell xenografts. Proc Natl Acad Sci U S A. Sep. 2, 2008;105(35):12991-6. Epub Aug. 26, 2008.

(56) References Cited

OTHER PUBLICATIONS

Taupin. Adult neural stem cells: The promise of the future. Neuropsychiatric Disease and Treatment 2007:3(6) 753-760.
Thornson, et al. Embryonic Stem Cell Lines Derived from Human Blastocysts, Science, vol. 282 pp. 1145-1147 (1998).
Torres, et al. Nanog maintains pluripotency of mouse embryonic stem cells by inhibiting NFkappaB and cooperating with Stat3. Nat Cell Biol. Feb. 2008;10(2):194-201. Epub Jan. 27, 2008.
Tsai, et al. The ubiquitin ligase gp78 promotes sarcoma metastasis by targeting KAI1 for degradation. Nat. Med. 2007; 13:1504-1509.
Von Gunten, et al. Sialic acid binding immunoglobulin-like lectins may regulate innate immune responses by modulating the life span of granulocytes. FASEB J. Apr. 2006;20(6):601-5.
Wanggren, et al. Leukaemia inhibitory factor receptor and gp130 in the human Fallopian tube and endometrium before and after mifepristone treatment and in the human preimplantation embryo. Mol Hum Reprod. Jun. 2007 ;13(6):391-7. Epub Apr. 12, 2007.
Yamanaka, et al. Cell and molecular regulation of the mouse blastocyst. Dev Dyn. Sep. 2006;235(9):2301-14.
Yokoyama, et al. Involvement of Two Distinct N-Acetylglucosaminyltransferases and a Dual-Function Deacetylase in Neomycin Biosynthesis. ChemBioChem. 2008; 9:865-869.
Yu, et al. Stem cell sources and therapeutic approaches for central nervous system and neural retinal disorders. Neurosurg Focus. 2008 ; 24(3-4): E11. doi:10.3171/FOC/2008/24/3-4/E10.
Zhang, et al. Induction of neuronal differentiation of adult human olfactory neuroepithelial-derived progenitors. Brain Res. Feb. 16, 2006;1073-1074:109-19. Epub Feb. 7, 2006.
Zhu, et al. Grafted neural stem cells migrate to substantia nigra and improve behavior in Parkinsonian rats. Neurosci Lett. Oct. 25, 2009;462(3):213-8. Epub Jul. 9, 2009.
Office action dated Mar. 11, 2015 for U.S. Appl. No. 13/296,876.
Barany. Genetic disease detection and DNA amplification using cloned thermostable ligase. Proc Natl Acad Sci U S A. Jan. 1, 1991;88(1):189-93.
Co-pending U.S. Appl. No. 14/840,970, filed Aug. 31, 2015.
Co-pending U.S. Appl. No. 14/952,023, filed Nov. 25, 2015.
Guatelli, et al. Isothermal, in vitro amplification of nucleic acids by a multienzyme reaction modeled after retroviral replication. Proc Natl Acad Sci U S A. Mar. 1990;87(5):1874-8.
Guha, et al. Hepatocyte-based gene therapy. J Hepatobiliary Pancreat Surg. 2001;8(1):51-7.
Kwoh, et al. Transcription-based amplification system and detection of amplified human immunodeficiency virus type 1 with a bead-based sandwich hybridization format. Proc Natl Acad Sci U S A. Feb. 1989;86(4):1173-7.
Lizardi, et al. Exponential amplification of recombinant-RNA hybridization probes. Nature Biotechnology 6.10 (1988): 1197-1202.
Office action dated Jan. 8, 2016 for U.S. Appl. No. 13/296,876.

\* cited by examiner

Betatrophin / Insulin / DAPI stain

SEQUENCE LISTING

```
<160> NUMBER OF SEQ ID NOS: 158

<210> SEQ ID NO 1
<211> LENGTH: 22
<212> TYPE: RNA
<213> ORGANISM: Homo sapiens

<400> SEQUENCE: 1
cguguucaca gcggaccuug au                                              22

<210> SEQ ID NO 2
<211> LENGTH: 20
<212> TYPE: RNA
<213> ORGANISM: Homo sapiens

<400> SEQUENCE: 2
uaaggcacgc ggugaaugcc                                                 20

<210> SEQ ID NO 3
```

-continued

```
<211> LENGTH: 85
<212> TYPE: RNA
<213> ORGANISM: Homo sapiens

<400> SEQUENCE: 3
aggccucucu cuccguguuc acagcggacc uugauuuaaa uguccauaca auuaaggcac    60
gcggugaaug ccaagaaugg ggcug                                         85

<210> SEQ ID NO 4
<211> LENGTH: 19
<212> TYPE: RNA
<213> ORGANISM: Aedes aegypti

<400> SEQUENCE: 4
uaaggcacgc ggugaaugc                                                19

<210> SEQ ID NO 5
<211> LENGTH: 21
<212> TYPE: RNA
<213> ORGANISM: Anolis carolinensis

<400> SEQUENCE: 5
uaaggcacgc ggugaaugcc a                                             21

<210> SEQ ID NO 6
<211> LENGTH: 21
<212> TYPE: RNA
<213> ORGANISM: Anolis carolinensis

<400> SEQUENCE: 6
uaaggcacgc ggugaaugcu a                                             21

<210> SEQ ID NO 7
<211> LENGTH: 23
<212> TYPE: RNA
<213> ORGANISM: Anopheles gambiae

<400> SEQUENCE: 7
uaaggcacgc ggugaaugcc aag                                           23

<210> SEQ ID NO 8
<211> LENGTH: 22
<212> TYPE: RNA
<213> ORGANISM: Ateles geoffroyi

<400> SEQUENCE: 8
uuaaggcacg cggugaaugc ca                                            22

<210> SEQ ID NO 9
<211> LENGTH: 23
<212> TYPE: RNA
<213> ORGANISM: Apis mellifera

<400> SEQUENCE: 9
uaaggcacgc ggugaaugcc aag                                           23

<210> SEQ ID NO 10
<211> LENGTH: 21
<212> TYPE: RNA
<213> ORGANISM: Acyrthosiphon pisum

<400> SEQUENCE: 10
uaaggcacgc ggugaaugcc a                                             21
```

<210> SEQ ID NO 11
<211> LENGTH: 22
<212> TYPE: RNA
<213> ORGANISM: Ascaris suum

<400> SEQUENCE: 11
cgccuucacc ggugacuuug gu                                              22

<210> SEQ ID NO 12
<211> LENGTH: 21
<212> TYPE: RNA
<213> ORGANISM: Ascaris suum

<400> SEQUENCE: 12
uaaggcacgc ggugaaugcc a                                               21

<210> SEQ ID NO 13
<211> LENGTH: 22
<212> TYPE: RNA
<213> ORGANISM: Branchiostoma floridae

<400> SEQUENCE: 13
aguguucacg gcgguccuua au                                              22

<210> SEQ ID NO 14
<211> LENGTH: 22
<212> TYPE: RNA
<213> ORGANISM: Branchiostoma floridae

<400> SEQUENCE: 14
uaaggcacgc ggugaaugcc aa                                              22

<210> SEQ ID NO 15
<211> LENGTH: 22
<212> TYPE: RNA
<213> ORGANISM: Brugia malayi

<400> SEQUENCE: 15
uaaggcacgc ggugaaugcc aa                                              22

<210> SEQ ID NO 16
<211> LENGTH: 23
<212> TYPE: RNA
<213> ORGANISM: Bombyx mori

<400> SEQUENCE: 16
uaaggcacgc ggugaaugcc aag                                             23

<210> SEQ ID NO 17
<211> LENGTH: 23
<212> TYPE: RNA
<213> ORGANISM: Bos taurus

<400> SEQUENCE: 17
uaaggcacgc ggugaaugcc aag                                             23

<210> SEQ ID NO 18
<211> LENGTH: 23
<212> TYPE: RNA
<213> ORGANISM: Bos taurus

<400> SEQUENCE: 18
uaaggcacgc ggugaaugcc aag                                            23

<210> SEQ ID NO 19
<211> LENGTH: 21
<212> TYPE: RNA
<213> ORGANISM: Caenorhabditis briggsae

<400> SEQUENCE: 19
uaaggcacgc ggugaaugcc a                                              21

<210> SEQ ID NO 20
<211> LENGTH: 20
<212> TYPE: RNA
<213> ORGANISM: Cyprinus carpio

<400> SEQUENCE: 20
ucaagguccg cugugaacac                                                20

<210> SEQ ID NO 21
<211> LENGTH: 22
<212> TYPE: RNA
<213> ORGANISM: Cyprinus carpio

<400> SEQUENCE: 21
ucaagguccg ccgugaacac gc                                             22

<210> SEQ ID NO 22
<211> LENGTH: 23
<212> TYPE: RNA
<213> ORGANISM: Caenorhabditis elegans

<400> SEQUENCE: 22
gcaugcaccc uagugacuuu agu                                            23

<210> SEQ ID NO 23
<211> LENGTH: 21
<212> TYPE: RNA
<213> ORGANISM: Caenorhabditis elegans

<400> SEQUENCE: 23
uaaggcacgc ggugaaugcc a                                              21

<210> SEQ ID NO 24
<211> LENGTH: 21
<212> TYPE: RNA
<213> ORGANISM: Canis familiaris

<400> SEQUENCE: 24
uaaggcacgc ggugaaugcc a                                              21

<210> SEQ ID NO 25
<211> LENGTH: 21
<212> TYPE: RNA
<213> ORGANISM: Canis familiaris

<400> SEQUENCE: 25
uaaggcacgc ggugaaugcc a                                              21

<210> SEQ ID NO 26
<211> LENGTH: 22
<212> TYPE: RNA
<213> ORGANISM: Cricetulus griseus

<400> SEQUENCE: 26
uaaggcacgc ggugaaugcc aa    22

<210> SEQ ID NO 27
<211> LENGTH: 20
<212> TYPE: RNA
<213> ORGANISM: Ciona intestinalis

<400> SEQUENCE: 27
aguauuuauu guggaccuug    20

<210> SEQ ID NO 28
<211> LENGTH: 22
<212> TYPE: RNA
<213> ORGANISM: Ciona intestinalis

<400> SEQUENCE: 28
uaaggcacgc ggugaaugcc aa    22

<210> SEQ ID NO 29
<211> LENGTH: 20
<212> TYPE: RNA
<213> ORGANISM: Ciona intestinalis

<400> SEQUENCE: 29
cguguuuacu guggaccuug    20

<210> SEQ ID NO 30
<211> LENGTH: 19
<212> TYPE: RNA
<213> ORGANISM: Culex quinquefasciatus

<400> SEQUENCE: 30
uaaggcacgc ggugaaugc    19

<210> SEQ ID NO 31
<211> LENGTH: 20
<212> TYPE: RNA
<213> ORGANISM: Caenorhabditis remanei

<400> SEQUENCE: 31
uaaggcacgc ggugaaugcc    20

<210> SEQ ID NO 32
<211> LENGTH: 22
<212> TYPE: RNA
<213> ORGANISM: Ciona savignyi

<400> SEQUENCE: 32
uaaggcacgc ggugaaugcc aa    22

<210> SEQ ID NO 33
<211> LENGTH: 21
<212> TYPE: RNA
<213> ORGANISM: Capitella teleta

<400> SEQUENCE: 33
uaaggcacgc ggugaaugcc a    21

<210> SEQ ID NO 34
<211> LENGTH: 23
<212> TYPE: RNA
<213> ORGANISM: Drosophila ananassae

```
<400> SEQUENCE: 34
uaaggcacgc ggugaaugcc aag                                          23

<210> SEQ ID NO 35
<211> LENGTH: 23
<212> TYPE: RNA
<213> ORGANISM: Drosophila erecta

<400> SEQUENCE: 35
uaaggcacgc ggugaaugcc aag                                          23

<210> SEQ ID NO 36
<211> LENGTH: 23
<212> TYPE: RNA
<213> ORGANISM: Drosophila grimshawi

<400> SEQUENCE: 36
uaaggcacgc ggugaaugcc aag                                          23

<210> SEQ ID NO 37
<211> LENGTH: 23
<212> TYPE: RNA
<213> ORGANISM: Drosophila melanogaster

<400> SEQUENCE: 37
gguauccacu guaggccuau aug                                          23

<210> SEQ ID NO 38
<211> LENGTH: 23
<212> TYPE: RNA
<213> ORGANISM: Drosophila melanogaster

<400> SEQUENCE: 38
uaaggcacgc ggugaaugcc aag                                          23

<210> SEQ ID NO 39
<211> LENGTH: 23
<212> TYPE: RNA
<213> ORGANISM: Drosophila mojavensis

<400> SEQUENCE: 39
uaaggcacgc ggugaaugcc aag                                          23

<210> SEQ ID NO 40
<211> LENGTH: 23
<212> TYPE: RNA
<213> ORGANISM: Drosophila persimilis

<400> SEQUENCE: 40
uaaggcacgc ggugaaugcc aag                                          23

<210> SEQ ID NO 41
<211> LENGTH: 23
<212> TYPE: RNA
<213> ORGANISM: Drosophila pseudoobscura

<400> SEQUENCE: 41
uaaggcacgc ggugaaugcc aag                                          23

<210> SEQ ID NO 42
<211> LENGTH: 23
<212> TYPE: RNA
<213> ORGANISM: Daphnia pulex
```

```
<400> SEQUENCE: 42
uaaggcacgc ggugaaugcc aag                                              23

<210> SEQ ID NO 43
<211> LENGTH: 22
<212> TYPE: RNA
<213> ORGANISM: Danio rerio

<400> SEQUENCE: 43
uaaggcacgc ggugaaugcc aa                                               22

<210> SEQ ID NO 44
<211> LENGTH: 23
<212> TYPE: RNA
<213> ORGANISM: Drosophila sechellia

<400> SEQUENCE: 44
uaaggcacgc ggugaaugcc aag                                              23

<210> SEQ ID NO 45
<211> LENGTH: 23
<212> TYPE: RNA
<213> ORGANISM: Drosophila simulans

<400> SEQUENCE: 45
uaaggcacgc ggugaaugcc aag                                              23

<210> SEQ ID NO 46
<211> LENGTH: 23
<212> TYPE: RNA
<213> ORGANISM: Drosophila virilis

<400> SEQUENCE: 46
uaaggcacgc ggugaaugcc aag                                              23

<210> SEQ ID NO 47
<211> LENGTH: 23
<212> TYPE: RNA
<213> ORGANISM: Drosophila willistoni

<400> SEQUENCE: 47
uaaggcacgc ggugaaugcc aag                                              23

<210> SEQ ID NO 48
<211> LENGTH: 23
<212> TYPE: RNA
<213> ORGANISM: Drosophila yakuba

<400> SEQUENCE: 48
uaaggcacgc ggugaaugcc aag                                              23

<210> SEQ ID NO 49
<211> LENGTH: 20
<212> TYPE: RNA
<213> ORGANISM: Equus caballus

<400> SEQUENCE: 49
uaaggcacgc ggugaaugcc                                                  20

<210> SEQ ID NO 50
<211> LENGTH: 21
<212> TYPE: RNA
```

```
<213> ORGANISM: Echinococcus granulosus

<400> SEQUENCE: 50
uaaggcacgc ggugaaugcc a                                              21

<210> SEQ ID NO 51
<211> LENGTH: 23
<212> TYPE: RNA
<213> ORGANISM: Echinococcus granulosus

<400> SEQUENCE: 51
guauucuacg cgaugucuug gua                                            23

<210> SEQ ID NO 52
<211> LENGTH: 20
<212> TYPE: RNA
<213> ORGANISM: Echinococcus granulosus

<400> SEQUENCE: 52
uaaggcacgc ggugaauacc                                                20

<210> SEQ ID NO 53
<211> LENGTH: 21
<212> TYPE: RNA
<213> ORGANISM: Echinococcus multilocularis

<400> SEQUENCE: 53
uaaggcacgc ggugaaugcc a                                              21

<210> SEQ ID NO 54
<211> LENGTH: 20
<212> TYPE: RNA
<213> ORGANISM: Echinococcus multilocularis

<400> SEQUENCE: 54
uaaggcacgc ggugaauacc                                                20

<210> SEQ ID NO 55
<211> LENGTH: 22
<212> TYPE: RNA
<213> ORGANISM: Fugu rubripes

<400> SEQUENCE: 55
uaaggcacgc ggugaaugcc aa                                             22

<210> SEQ ID NO 56
<211> LENGTH: 22
<212> TYPE: RNA
<213> ORGANISM: Gallus gallus

<400> SEQUENCE: 56
uuaaggcacg cggugaaugc ca                                             22

<210> SEQ ID NO 57
<211> LENGTH: 22
<212> TYPE: RNA
<213> ORGANISM: Gallus gallus

<400> SEQUENCE: 57
uuaaggcacg cagugaaugc ca                                             22

<210> SEQ ID NO 58
<211> LENGTH: 21
```

```
<212> TYPE: RNA
<213> ORGANISM: Gallus gallus

<400> SEQUENCE: 58
cauucaccgc gugccuuaau u                                              21

<210> SEQ ID NO 59
<211> LENGTH: 22
<212> TYPE: RNA
<213> ORGANISM: Gorilla gorilla

<400> SEQUENCE: 59
uuaaggcacg cggugaaugc ca                                             22

<210> SEQ ID NO 60
<211> LENGTH: 22
<212> TYPE: RNA
<213> ORGANISM: Haemonchus contortus

<400> SEQUENCE: 60
uaaggcacgc ggugaaugcc aa                                             22

<210> SEQ ID NO 61
<211> LENGTH: 22
<212> TYPE: RNA
<213> ORGANISM: Heliconius melpomene

<400> SEQUENCE: 61
uaaggcacgc ggugaaugcc aa                                             22

<210> SEQ ID NO 62
<211> LENGTH: 23
<212> TYPE: RNA
<213> ORGANISM: Ixodes scapularis

<400> SEQUENCE: 62
uaaggcacgc ggugaaugcc aag                                            23

<210> SEQ ID NO 63
<211> LENGTH: 21
<212> TYPE: RNA
<213> ORGANISM: Lottia gigantean

<400> SEQUENCE: 63
uaaggcacgc ggugaaugcc a                                              21

<210> SEQ ID NO 64
<211> LENGTH: 22
<212> TYPE: RNA
<213> ORGANISM: Lagothrix lagotricha

<400> SEQUENCE: 64
uuaaggcacg cggugaaugc ca                                             22

<210> SEQ ID NO 65
<211> LENGTH: 22
<212> TYPE: RNA
<213> ORGANISM: Monodelphis domestica

<400> SEQUENCE: 65
uuaaggcacg cggugaaugc ca                                             22

<210> SEQ ID NO 66
```

```
<211> LENGTH: 22
<212> TYPE: RNA
<213> ORGANISM: Macaca mulatta

<400> SEQUENCE: 66
uuaaggcacg cggugaaugc ca                                              22

<210> SEQ ID NO 67
<211> LENGTH: 22
<212> TYPE: RNA
<213> ORGANISM: Mus musculus

<400> SEQUENCE: 67
cguguucaca gcggaccuug au                                              22

<210> SEQ ID NO 68
<211> LENGTH: 20
<212> TYPE: RNA
<213> ORGANISM: Mus musculus

<400> SEQUENCE: 68
uaaggcacgc ggugaaugcc                                                 20

<210> SEQ ID NO 69
<211> LENGTH: 21
<212> TYPE: RNA
<213> ORGANISM: Manduca sexta

<400> SEQUENCE: 69
uaaggcacgc ggugaaugcc a                                               21

<210> SEQ ID NO 70
<211> LENGTH: 23
<212> TYPE: RNA
<213> ORGANISM: Nasonia vitripennis

<400> SEQUENCE: 70
uaaggcacgc ggugaaugcc aag                                             23

<210> SEQ ID NO 71
<211> LENGTH: 22
<212> TYPE: RNA
<213> ORGANISM: Ornithorhynchus anatinus

<400> SEQUENCE: 71
cguguucaca gcggaccuug au                                              22

<210> SEQ ID NO 72
<211> LENGTH: 21
<212> TYPE: RNA
<213> ORGANISM: Ornithorhynchus anatinus

<400> SEQUENCE: 72
uaaggcacgc ggugaaugcc a                                               21

<210> SEQ ID NO 73
<211> LENGTH: 22
<212> TYPE: RNA
<213> ORGANISM: Oikopleura dioica

<400> SEQUENCE: 73
uaaggcacgc ggugaaugcu aa                                              22
```

```
<210> SEQ ID NO 74
<211> LENGTH: 22
<212> TYPE: RNA
<213> ORGANISM: Oikopleura dioica

<400> SEQUENCE: 74
uaaggcacuc ggugaaugcu aa                                              22

<210> SEQ ID NO 75
<211> LENGTH: 19
<212> TYPE: RNA
<213> ORGANISM: Oryzias latipes

<400> SEQUENCE: 75
cguguucaca gcggaccuu                                                  19

<210> SEQ ID NO 76
<211> LENGTH: 21
<212> TYPE: RNA
<213> ORGANISM: Oryzias latipes

<400> SEQUENCE: 76
uaaggcacgc ggugaaugcc a                                               21

<210> SEQ ID NO 77
<211> LENGTH: 22
<212> TYPE: RNA
<213> ORGANISM: Petromyzon marinus

<400> SEQUENCE: 77
cguguucaca gcggaccuug au                                              22

<210> SEQ ID NO 78
<211> LENGTH: 21
<212> TYPE: RNA
<213> ORGANISM: Petromyzon marinus

<400> SEQUENCE: 78
uaaggcacgc ggugaaugcc a                                               21

<210> SEQ ID NO 79
<211> LENGTH: 22
<212> TYPE: RNA
<213> ORGANISM: Paralichthys olivaceus

<400> SEQUENCE: 79
cguguucaca gcggaccuug au                                              22

<210> SEQ ID NO 80
<211> LENGTH: 22
<212> TYPE: RNA
<213> ORGANISM: Paralichthys olivaceus

<400> SEQUENCE: 80
uaaggcacgc ggugaaugcc aa                                              22

<210> SEQ ID NO 81
<211> LENGTH: 22
<212> TYPE: RNA
<213> ORGANISM: Pan paniscus

<400> SEQUENCE: 81
uuaaggcacg cggugaaugc ca                                              22
```

<210> SEQ ID NO 82
<211> LENGTH: 20
<212> TYPE: RNA
<213> ORGANISM: Pristionchus pacificus

<400> SEQUENCE: 82
uaaggcacgc ggugaaugcc                                               20

<210> SEQ ID NO 83
<211> LENGTH: 20
<212> TYPE: RNA
<213> ORGANISM: Pongo pygmaeus

<400> SEQUENCE: 83
uaaggcacgc ggugaaugcc                                               20

<210> SEQ ID NO 84
<211> LENGTH: 22
<212> TYPE: RNA
<213> ORGANISM: Pongo pygmaeus

<400> SEQUENCE: 84
uuaaggcacg cggugaaugc ca                                            22

<210> SEQ ID NO 85
<211> LENGTH: 22
<212> TYPE: RNA
<213> ORGANISM: Pan troglodytes

<400> SEQUENCE: 85
uuaaggcacg cggugaaugc ca                                            22

<210> SEQ ID NO 86
<211> LENGTH: 22
<212> TYPE: RNA
<213> ORGANISM: Rattus norvegicus

<400> SEQUENCE: 86
cguguucaca gcggaccuug au                                            22

<210> SEQ ID NO 87
<211> LENGTH: 20
<212> TYPE: RNA
<213> ORGANISM: Rattus norvegicus

<400> SEQUENCE: 87
uaaggcacgc ggugaaugcc                                               20

<210> SEQ ID NO 88
<211> LENGTH: 25
<212> TYPE: RNA
<213> ORGANISM: Schistosoma japonicum

<400> SEQUENCE: 88
ccauuuuccg cgauugccuu gauuu                                         25

<210> SEQ ID NO 89
<211> LENGTH: 21
<212> TYPE: RNA
<213> ORGANISM: Schistosoma japonicum

<400> SEQUENCE: 89
uaaggcacgc ggugaauguc a                                             21

<210> SEQ ID NO 90
<211> LENGTH: 22
<212> TYPE: RNA
<213> ORGANISM: Saccoglossus kowalevskii

<400> SEQUENCE: 90
aguguucaca gcgguccuug au                                          22

<210> SEQ ID NO 91
<211> LENGTH: 22
<212> TYPE: RNA
<213> ORGANISM: Saccoglossus kowalevskii

<400> SEQUENCE: 91
uaaggcacgc ggugaaugcc aa                                          22

<210> SEQ ID NO 92
<211> LENGTH: 23
<212> TYPE: RNA
<213> ORGANISM: Schmidtea mediterranea

<400> SEQUENCE: 92
ugcuuuuaac gcggagcuuu agu                                         23

<210> SEQ ID NO 93
<211> LENGTH: 21
<212> TYPE: RNA
<213> ORGANISM: Schmidtea mediterranea

<400> SEQUENCE: 93
uaaggcacgc ggugaaugcu u                                           21

<210> SEQ ID NO 94
<211> LENGTH: 23
<212> TYPE: RNA
<213> ORGANISM: Schmidtea mediterranea

<400> SEQUENCE: 94
ugcauuuaca acgugucuuu agu                                         23

<210> SEQ ID NO 95
<211> LENGTH: 22
<212> TYPE: RNA
<213> ORGANISM: Schmidtea mediterranea

<400> SEQUENCE: 95
uaaggcacgc ggugaaugcu ga                                          22

<210> SEQ ID NO 96
<211> LENGTH: 22
<212> TYPE: RNA
<213> ORGANISM: Schmidtea mediterranea

<400> SEQUENCE: 96
gcgcucaccu cgugaccuuu gu                                          22

<210> SEQ ID NO 97
<211> LENGTH: 21
<212> TYPE: RNA
<213> ORGANISM: Schmidtea mediterranea

<400> SEQUENCE: 97
uaaggcacgc ggugaaugcc a                                                21

<210> SEQ ID NO 98
<211> LENGTH: 23
<212> TYPE: RNA
<213> ORGANISM: Schmidtea mediterranea

<400> SEQUENCE: 98
gcauuaaccc uguugucuua gau                                              23

<210> SEQ ID NO 99
<211> LENGTH: 21
<212> TYPE: RNA
<213> ORGANISM: Schmidtea mediterranea

<400> SEQUENCE: 99
gccauucuca guuggagucu u                                                21

<210> SEQ ID NO 100
<211> LENGTH: 21
<212> TYPE: RNA
<213> ORGANISM: Schmidtea mediterranea

<400> SEQUENCE: 100
uaaggcacgc ugugaaugcc a                                                21

<210> SEQ ID NO 101
<211> LENGTH: 21
<212> TYPE: RNA
<213> ORGANISM: Strongylocentrotus purpuratus

<400> SEQUENCE: 101
uaaggcacgc ggugaaugcc a                                                21

<210> SEQ ID NO 102
<211> LENGTH: 21
<212> TYPE: RNA
<213> ORGANISM: Sus scrofa

<400> SEQUENCE: 102
uaaggcacgc ggugaaugcc a                                                21

<210> SEQ ID NO 103
<211> LENGTH: 21
<212> TYPE: RNA
<213> ORGANISM: Sus scrofa

<400> SEQUENCE: 103
uaaggcacgc ggugaaugcc a                                                21

<210> SEQ ID NO 104
<211> LENGTH: 22
<212> TYPE: RNA
<213> ORGANISM: Tribolium castaneu

<400> SEQUENCE: 104
aguguucacu guuggccugu au                                               22

<210> SEQ ID NO 105
<211> LENGTH: 23
<212> TYPE: RNA
<213> ORGANISM: Tribolium castaneu

<400> SEQUENCE: 105
uaaggcacgc ggugaaugcc aag                                                    23

<210> SEQ ID NO 106
<211> LENGTH: 21
<212> TYPE: RNA
<213> ORGANISM: Taeniopygia guttata

<400> SEQUENCE: 106
cguguucaca gcggaccuug a                                                      21

<210> SEQ ID NO 107
<211> LENGTH: 21
<212> TYPE: RNA
<213> ORGANISM: Taeniopygia guttata

<400> SEQUENCE: 107
uaaggcacgc ggugaaugcc a                                                      21

<210> SEQ ID NO 108
<211> LENGTH: 22
<212> TYPE: RNA
<213> ORGANISM: Tetraodon nigroviridis

<400> SEQUENCE: 108
uaaggcacgc ggugaaugcc aa                                                     22

<210> SEQ ID NO 109
<211> LENGTH: 22
<212> TYPE: RNA
<213> ORGANISM: Tetranychus urticae

<400> SEQUENCE: 109
cguguucacu guguaugucu ug                                                     22

<210> SEQ ID NO 110
<211> LENGTH: 21
<212> TYPE: RNA
<213> ORGANISM: Tetranychus urticae

<400> SEQUENCE: 110
uaaggcacgc ggugaaugcc a                                                      21

<210> SEQ ID NO 111
<211> LENGTH: 22
<212> TYPE: RNA
<213> ORGANISM: Tetranychus urticae

<400> SEQUENCE: 111
guguucacug uuugccuuca ug                                                     22

<210> SEQ ID NO 112
<211> LENGTH: 22
<212> TYPE: RNA
<213> ORGANISM: Xenoturbella bocki

<400> SEQUENCE: 112
uaaggcacgc ggugaaugcc aa                                                     22

<210> SEQ ID NO 113
<211> LENGTH: 22
<212> TYPE: RNA
<213> ORGANISM: Xenopus tropicalis

```
<400> SEQUENCE: 113
uuaaggcacg cggugaaugc ca                                              22

<210> SEQ ID NO 114
<211> LENGTH: 21
<212> TYPE: RNA
<213> ORGANISM: Schmidtea mediterranea

<400> SEQUENCE: 114
uaaggcacgc gguaaguggg u                                               21

<210> SEQ ID NO 115
<211> LENGTH: 23
<212> TYPE: RNA
<213> ORGANISM: Schmidtea mediterranea

<400> SEQUENCE: 115
aacauuuaca agcgagccuu aau                                             23

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gtacttcata ccatgccgat t                                               21

<210> SEQ ID NO 117
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
ccgggtactt cataccatgc cgattctcga gaatcggcat ggtatgaagt acttttttg      58

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
cagattgtct tgcaacttca g                                               21

<210> SEQ ID NO 119
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ccggcagatt gtcttgcaac ttcagctcga gctgaagttg caagacaatc tgttttttg     58

<210> SEQ ID NO 120
<211> LENGTH: 21
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
taccatacag agaacattgg a                                              21

<210> SEQ ID NO 121
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
ccggtaccat acagagaaca ttggactcga gtccaatgtt ctctgtatgg tatttttg     58

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
acatctccct ccccagactc                                                20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
tgctctgtgc tcagaagtgg                                                20

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
ctgtcggctg agggtttcca t                                              21

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gagtctgggg agggagatgt                                                20

<210> SEQ ID NO 126
<211> LENGTH: 20
<212> TYPE: DNA

<213> ORGANISM: Artificial Sequence
<220> FEATURE:
<223> OTHER INFORMATION: Description of Artificial Sequence: Synthetic primer

<400> SEQUENCE: 126
tctgcggctc tttggtttca					20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 127
tctgccttca gcacaagagg					20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 128
gcggctcttt ggtttcaagg					20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 129
ctgccttcag cacaagagga					20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 130
cccgcagttc tcaaggacac					20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 131
agaagggagc caggcaagtc					20

<210> SEQ ID NO 132
<211> LENGTH: 23
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 132
ttgtagattg ctctctctcc tcc                                            23

<210> SEQ ID NO 133
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
gtgaagcctt ggctagggg                                                 19

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
cccatcattg attcctggat                                                20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
ttgggaggct gagatttgtc                                                20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gtcagccctc cctgactgat                                                20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
catgtggatt tccagcctgc                                                20

<210> SEQ ID NO 138
<211> LENGTH: 29
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 138
aaattataag ctgtttgggt tgttggtct                                      29

<210> SEQ ID NO 139
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
aaacaattgc ccccataatt tctgactgc                                      29

<210> SEQ ID NO 140
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
aaattataac tcccaaagtg ctgggatta                                      29

<210> SEQ ID NO 141
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
aaacaattgc tgcactgttc acaggagga                                      29

<210> SEQ ID NO 142
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
aaattataac agttgtccca gtgctgcta                                      29

<210> SEQ ID NO 143
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
aaacaattga tgacttgccc aaaggtcac                                      29

<210> SEQ ID NO 144
<211> LENGTH: 29
<212> TYPE: DNA
<213> ORGANISM: Artificial Sequence
<220> FEATURE:
<223> OTHER INFORMATION: Description of Artificial Sequence: Synthetic
```

```
                                                  -continued
      primer

<400> SEQUENCE: 144
aaattataac ccacaactgg ggtaaaaga                                           29

<210> SEQ ID NO 145
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
aaacaattgc tgtggaaggg gcaaagata                                           29

<210> SEQ ID NO 146
<211> LENGTH: 109
<212> TYPE: RNA
<213> ORGANISM: Homo sapiens

<400> SEQUENCE: 146
aucaagauua gaggcucugc ucuccguguu cacagcggac cuugauuuaa ugucauacaa         60
uuaaggcacg cggugaaugc caagagcgga gccuacggcu gcacuugaa                    109

<210> SEQ ID NO 147
<211> LENGTH: 87
<212> TYPE: RNA
<213> ORGANISM: Homo sapiens

<400> SEQUENCE: 147
ugagggcccc ucugcguguu cacagcggac cuugauuuaa ugucuauaca auuaaggcac         60
gcggugaaug ccaagagagg cgccucc                                            87

<210> SEQ ID NO 148
<211> LENGTH: 11
<212> TYPE: DNA
<213> ORGANISM: Unknown
<220> FEATURE:
<223> OTHER INFORMATION: Description of Unknown: CREB1-binding site 1
      oligonucleotide

<400> SEQUENCE: 148
acgccgtcat t                                                             11

<210> SEQ ID NO 149
<211> LENGTH: 12
<212> TYPE: DNA
<213> ORGANISM: Unknown
<220> FEATURE:
<223> OTHER INFORMATION: Description of Unknown: CREB1-binding site 2
      oligonucleotide

<400> SEQUENCE: 149
ggtgacgtca gc                                                            12

<210> SEQ ID NO 150
<211> LENGTH: 12
<212> TYPE: DNA
<213> ORGANISM: Unknown
<220> FEATURE:
<223> OTHER INFORMATION: Description of Unknown: CREB1-binding site
      oligonucleotide

<400> SEQUENCE: 150
```

-continued

```
ggtgacgtca cc                                                   12

<210> SEQ ID NO 151
<211> LENGTH: 17
<212> TYPE: RNA
<213> ORGANISM: Homo sapiens

<400> SEQUENCE: 151 guuguccag ugccuuu                                               17

<210> SEQ ID NO 152
<211> LENGTH: 16
<212> TYPE: RNA
<213> ORGANISM: Homo sapiens

<400> SEQUENCE: 152
auccagaauu gccuua                                               16

<210> SEQ ID NO 153
<211> LENGTH: 17
<212> TYPE: RNA
<213> ORGANISM: Homo sapiens

<400> SEQUENCE: 153
gggaguauuu gaacaca                                              17

<210> SEQ ID NO 154
<211> LENGTH: 17
<212> TYPE: RNA
<213> ORGANISM: Homo sapiens

<400> SEQUENCE: 154
cguguucaca gcggacc                                              17

<210> SEQ ID NO 155
<211> LENGTH: 15
<212> TYPE: RNA
<213> ORGANISM: Homo sapiens

<400> SEQUENCE: 155
guuuggagug ccuuc                                                15

<210> SEQ ID NO 156
<211> LENGTH: 15
<212> TYPE: RNA
<213> ORGANISM: Homo sapiens

<400> SEQUENCE: 156
uaaggcacgc gguga                                                15

<210> SEQ ID NO 157
<211> LENGTH: 16
<212> TYPE: DNA
<213> ORGANISM: Unknown
<220> FEATURE:
<223> OTHER INFORMATION: Description of Unknown: Foxa2
      oligonucleotide

<400> SEQUENCE: 157
cctgtttgtt ttagtt                                               16

<210> SEQ ID NO 158
<211> LENGTH: 8
```

```
<212> TYPE: DNA
<213> ORGANISM: Unknown
<220> FEATURE:
<223> OTHER INFORMATION: Description of Unknown: Cis-regulatory
      element (CRE) oligonucleotide

<400> SEQUENCE: 158 tgacgtca                                                              8
```

METHODS OF DIFFERENTIATING STEM CELLS BY MODULATING MIR-124

CROSS-REFERENCE

This application claims the benefit of U.S. Provisional Application No. 61/732,162 filed Nov. 30, 2012 and U.S. Provisional Application No. 61/877,156 filed Sep. 12, 2013, both of which are incorporated herein by reference.

SEQUENCE LISTING

The instant application contains a Sequence Listing which has been submitted electronically in ASCII format and is hereby incorporated by reference in its entirety. Said ASCII copy, created on Nov. 25, 2013, is named 44980-703.201_SL.txt and is 26,917 bytes in size.

BACKGROUND

During gastrulation, epiblast cells give rise to primitive streak mesendoderm followed by three germ layers including definitive endoderm (DE). DE differentiates into primitive endoderm wherefrom the ventral and dorsal pancreatic buds develop into pancreas. Advanced human embryonic stem (hES) cell research has ignited a vision to generate glucose-sensing and insulin-secreting β-cells via DE specification for the treatment of type 1 diabetes. However, current hES cell approaches are time consuming and complex.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

BRIEF SUMMARY OF THE INVENTION

The inventive embodiments provided in this Brief Summary of the Invention are meant to be illustrative only and to provide an overview of selective embodiments disclosed herein. The Brief Summary of the Invention, being illustrative and selective, does not limit the scope of any claim, does not provide the entire scope of inventive embodiments disclosed or contemplated herein, and should not be construed as limiting or constraining the scope of this disclosure or any claimed inventive embodiment.

In one of many aspects, provided herein is a method of differentiating a mammalian trophoblast stem cell comprising modulating miR-124 to induce differentiation of the mammalian trophoblast stem cell to a differentiated cell. In one instance, the mammalian trophoblast stem cell is a human trophoblast stem (hTS) cell. In one instance, the mammalian trophoblast stem cell herein is from a rodent (e.g., mouse, rat, guinea pig, hamster, or squirrel), rabbit, cow, sheep, pig, dog, cat, monkey, ape (e.g., chimpanzee, gorilla, or orangutan), or human. In one instance, the differentiated cell is a progenitor cell, e.g., a pancreatic progenitor cell. In one instance, the differentiated cell is a pluripotent stem cell. In one instance, the differentiated cell is an endodermal, mesodermal, or ectodermal progenitor cell. In one instance, the differentiated cell is a definitive endoderm progenitor cell. In one instance, the differentiated cell is a pancreatic endoderm progenitor cell. In one instance, the differentiated cell is a multipotent progenitor cell. In one instance, the differentiated cell is an oligopotent progenitor cell. In one instance, the differentiated cell is a monopotent, bipotent, or tripotent progenitor cell. In one instance, the differentiated cell is an endocrine, exocrine, or duct progenitor cell, e.g., an endocrine progenitor cell. In one instance, the differentiated cell is a beta-cell. In one instance, the differentiated cell is an insulin-producing cell. One or more differentiated cells can be used in any method disclosed herein. In some embodiments, the modulating activates miR-124. In one instance, the modulating activates miR-124 spatiotemporarily, e.g., between about 1 hour to about 8 hours, at a definitive endoderm stage. In one instance, the modulating elevates miR-124 expression. In one instance, the modulating deactivates miR-124. In one instance, the modulating decreases miR-124 expression. In one instance, the modulating comprises contacting the mammalian trophoblast stem cell with one or more agents, e.g., proteins or steroid hormones. In one instance, the one or more agents comprise a growth factor, e.g., a fibroblast growth factor (FGF). In one instance, the FGF is FGF1, FGF2, FGF3, FGF4, FGF5, FGF6, FGF7, FGF8, FGF9, or FGF10. In one instance, the one or more agents comprise FGF2 (basic fibroblast growth factor, bFGF). In one instance, the concentration of bFGF herein is no more than about 100 ng/mL, e.g., from about 1 to about 100 ng/mL. In one instance, the concentration of bFGF herein is from about: 1-10, 10-20, 20-30, 30-40, 40-50, 50-60, 50-70, 80-90, or 90-100 ng/mL. In one instance, the concentration of bFGF herein is about: 1, 2, 3, 4, 5, 6, 7, 8, 9, 10, 11, 12, 13, 14, 15, 16, 17, 18, 19, 20, 25, 30, 35, 40, 45, 50, 60, 70, 80, or 90 ng/mL. In one instance, the one or more agents further comprise an antioxidant or reducing agent, e.g., 2-mercaptoethanol. In one instance, the concentration of 2-mercaptoethanol is no more than about 10 mmol/L, e.g., from about 0.1 to about 10 mmol/L. In one instance, the concentration of 2-mercaptoethanol is from about: 0.1-1, 1-2, 2-3, 3-4, 4-5, 5-6, 6-7, 7-8, 8-9, or 9-10 mmol/L. In one instance, the concentration of 2-mercaptoethanol is about: 0.2, 0.5, 1, 1.5, 2, 3, 4, 5, 6, 7, 8, or 9 mmol/L. In one instance, the one or more agents further comprise a vitamin. e.g., nicotinamide. In one instance, the concentration of nicotinamide is no more than about 100 mmol/L, e.g., from about 1 to about 100 mmol/L. In one instance, the concentration of nicotinamide is from about: 1-10, 10-20, 20-30, 30-40, 40-50, 50-60, 50-70, 80-90, or 90-100 mmol/L. In one instance, the concentration of nicotinamide is about: 2, 4, 6, 8, 10, 12, 14, 16, 18, 20, 30, 40, 50, 60, 70, 80, or 90 mmol/L. In one instance, the modulating comprises contacting the mammalian trophoblast stem cell with bFGF, 2-mercaptoethanol, and nicotinamide. In one instance, the one or more agents regulate activity or expression level of cAMP Responsive Element Binding Protein 1 (CREB1). In one instance, the one or more agents regulate CREB1 phosphorylation. In one instance, the one or more agents comprise a vitamin metabolite, e.g., retinoic acid. In one instance, the one or more agents comprise a CREB1-binding protein. In one instance, the one or more agents regulate one or more factors comprising mixl1, Cdx2, Oct4, Sox17, Foxa2, or GSK3β. In one instance, the one or more agents comprise an exogenous miR-124 precursor or an exogenous anti-miR-124. In one instance, the mammalian trophoblast stem cell is transfected with the exogenous miR-124 precursor or the exogenous anti-miR-124. In one instance, cis-regulatory element (CRE) of TGACGTCA (SEQ ID NO: 158) of promoters of the miR-124 is modulated. In one instance, the miR-124 is miR-124a, miR-124b, miR-124c, miR-124d, or miR-124e. In one instance, the miR-124 is miR-124a, e.g., *homo sapiens* miR-124a (hsa-miR-124a). In one instance, the hsa-miR-124 is hsa-miR-124-5p (SEQ ID NO:1: CGU-GUUCACAGCGGACCUUGAU) or a fragment thereof. In one instance, the hsa-miR-124 is hsa-miR-124-3p (SEQ ID NO:2: UAAGGCACGCGGUGAAUGCC) or a fragment thereof. In one instance, the miR-124 comprises a sequence selected from Table 1 and Table 2 or a fragment thereof. In one instance, the mammalian trophoblast stem cell differentiates into the differentiated cell within one day after the start of the modulating.

In one aspect, provided herein is one or more differentiated cells isolated from one or more methods herein. In one instance, the isolated differentiated cell is a human cell. In one instance, the isolated differentiated cell has a normal karyotype. In one instance, the isolated differentiated cell has one or more immune-privileged characteristics, e.g., low or absence of CD33 expression and/or CD133 expression. One or more isolated differentiated cells disclosed herein can be used in any method disclosed herein.

In another aspect, provided herein is an isolated progenitor cell that expresses one or more transcription factors comprising Foxa2, Pdx1, Ngn3, Ptf1a, Nkx6.1, or any combination thereof. In one instance, the isolated progenitor cell is an induced pluripotent stem cell. In one instance, the isolated progenitor cell is derived from a mammalian trophoblast stem cell, e.g., an hTS cell. In one instance, the isolated progenitor cell is a pancreatic progenitor cell. In one instance, the isolated progenitor cell is an endodermal, mesodermal, or ectodermal progenitor cell. In one instance, the isolated progenitor cell is a definitive endoderm progenitor cell. In one instance, the isolated progenitor cell is a pancreatic endoderm progenitor cell. In one instance, the isolated progenitor cell is a multipotent progenitor cell. In one instance, the isolated progenitor cell is an oligopotent progenitor cell. In one instance, the isolated progenitor cell is a monopotent, bipotent, or tripotent progenitor cell. In one instance, the isolated progenitor cell is an endocrine, exocrine, or duct progenitor cell, e.g., an endocrine progenitor cell. In one instance, the isolated progenitor cell is a beta-cell. In one instance, the isolated progenitor cell is an insulin-producing cell. In one instance, the isolated progenitor cell is from rodents (e.g, mice, rats, guinea pigs, hamsters, squirrels), rabbits, cows, sheep, pigs, dogs, cats, monkeys, apes (e.g., chimpanzees, gorillas, orangutans), or humans. In one instance, the isolated progenitor cell is a human cell. In one instance, the isolated progenitor cell has a normal karyotype. In one instance, the isolated progenitor cell has one or more immune-privileged characteristics, e.g., low or absence of CD33 expression and/or CD133 expression. An isolated progenitor cell disclosed herein can be used in any method disclosed herein.

In another aspect, provided herein is an isolated progenitor cell that expresses betatrophin, betatrophin mRNA, C-peptide, or insulin, wherein the isolated progenitor cell is differentiated from a mammalian trophoblast stem cell. In one instance, the isolated progenitor cell is from rodents (e.g, mice, rats, guinea pigs, hamsters, squirrels), rabbits, cows, sheep, pigs, dogs, cats, monkeys, apes (e.g., chimpanzees, gorillas, orangutans), or humans. In one instance, the isolated progenitor cell is a pancreatic progenitor cell. In one instance, the isolated progenitor cell is a human cell. In one instance, the isolated progenitor cell has a normal karyotype. In one instance, the isolated progenitor cell has one or more immune-privileged characteristics, e.g., low or absence of CD33 expression and/or CD133 expression. One or more isolated progenitor cells disclosed herein can be used in any method disclosed herein.

In one instance, an isolated progenitor cell herein is an insulin-producing cell. One or more isolated progenitor cells herein can be used in any method disclosed herein.

In one instance, a differentiated cell herein is an insulin-producing cell. One or more differentiated cells herein can be used in any method disclosed herein.

In one aspect, provided herein is a method of screening a substance for use in treatment or prevention of a disease comprising: a) contacting at least one isolated progenitor cell herein with the substance; and b) detecting a change in the level of at least one transcript or protein in the isolated progenitor cell. In one instance, the level of at least one transcript or protein in the isolated progenitor cell decreases as compared to a corresponding isolated progenitor cell not contacted with the substance. In one instance, the level of at least one transcript or protein in the isolated progenitor cell increases as compared to a corresponding isolated progenitor cell not contacted with the substance. In one instance, the disease is an insulin disorder. In one instance, the disease is diabetes, e.g., Type 1 diabetes or Type 2 diabetes.

In one aspect, provided herein is a method of screening a substance for cellular toxicity or modulation of a cell, the method comprising: a) contacting at least one isolated progenitor cell herein with the substance; b) determining a phenotypic and/or metabolic change in the isolated progenitor cell that result from contact with the substance; and c) correlating the change with cellular toxicity or modulation. In one instance, the cell is an insulin-producing cell. In one instance, the substance is a drug. In one instance, the substance is a chemical. In one instance, the substance is an antibody or fragment thereof. In one instance, the substance is added to the culture medium. In one instance, the method comprises determining the effect of the substance on growth of the isolated progenitor cell. In one instance, the method comprises determining whether the substance affects expression of a marker or receptor by the isolated progenitor cell. In some embodiments, the isolated progenitor cell is a pancreatic progenitor cell.

In one aspect, provided herein is a method of treating or preventing a disease in a mammal in need thereof comprising administering an isolated progenitor cell herein to the mammal in need thereof. In one instance, the isolated progenitor cell is immune privileged. In one instance, the isolated progenitor cell has low levels of CD33 expression and/or CD133 expression. In one instance, the administering comprises injecting, implanting, or surgical operation. In one instance, the disease is an insulin disorder. In one instance, the disease is diabetes, e.g., Type 1 diabetes or Type 2 diabetes. In one instance, the mammal in need thereof is a mouse, rat, pig, dog, monkey, orangutan, ape, or human. In one instance, the mammal in need thereof has one or more symptoms associated with diabetes, e.g., polyuria (frequent urination), polydipsia (increased thirst), polyphagia (increased hunger), weight loss, blurred vision, itchiness, peripheral neuropathy, recurrent vaginal infections, fatigue, slow healing of wounds or sores, and any combination thereof. In some embodiments, the isolated progenitor cell is a pancreatic progenitor cell.

In one aspect, provided herein is a method of producing insulin, comprising contacting a mammalian trophoblast stem cell with one or more agents to activate miR-124, thereby producing an isolated progenitor cell that secretes insulin in response to glucose stimulation. In another aspect, provided herein is a method of producing betatrophin protein and/or betatrophin mRNA, comprising contacting a mammalian trophoblast stem cell with one or more agents to activate miR-124, thereby producing a pancreatic progenitor cell that produces betatrophin protein and/or betatrophin mRNA. In one instance, the betatrophin protein or betatrophin mRNA is produced during about 12-28 hours after induction, e.g., about: 12-16, 16-20, 20-24, or 24-28 hours after induction. In one instance, the isolated progenitor cell is a pancreatic progenitor cell. In one instance, the isolated progenitor cell produces C-peptide and/or insulin. In some embodiments, the mammalian trophoblast stem cell is an hTS cell. In some embodiments, a mammalian trophoblast stem cell herein is from a rodent, rabbit, cow, sheep, pig, dog, cat, monkey, or ape. In some embodiments, a rodent herein is a mouse, rat, guinea pig, hamster, or squirrel. In some embodiments, an ape herein is chimpanzee, gorilla, or orangutan. In some embodiments, the miR-124 is activated spatiotemporarily at a definitive endoderm stage, e.g., between about 1 hour to about 8 hours at the definitive endoderm stage. In some embodiments, expression of the miR-124 is elevated. In some embodiments, the one or more agents comprise a protein or steroid hormone, e.g., a growth factor. In some embodiments, the growth factor is a fibroblast growth factor (FGF), e.g., FGF1, FGF2 (bFGF), FGF3, FGF4, FGF5, FGF6, FGF7, FGF8, FGF9, or FGF10. In some embodiments, the one or more agents comprise bFGF (basic fibroblast growth factor). In some embodiments, the bFGF is no more than about 100 ng/mL, e.g., from about 1 to about 100 ng/mL. In some embodiments, the concentration of bFGF used herein is from about: 1-10, 10-20, 20-30, 30-40, 40-50, 50-60, 50-70, 80-90, or 90-100 ng/mL. In some embodiments, the concentration of bFGF used herein is about: 1, 2, 3, 4, 5, 6, 7, 8, 9, 10, 11, 12, 13, 14, 15, 16, 17, 18, 19, 20, 25, 30, 35, 40, 45, 50, 60, 70, 80, or 90 ng/mL. In some embodiments, the bFGF is about 10 ng/mL. In some embodiments, the one or more agents further comprise an antioxidant or reducing agent (e.g., 2-mercaptoethanol). In some embodiments, the one or more agents further comprise a vitamin (e.g., nicotinamide). In some embodiments, the mammalian trophoblast stem cell is contacted with bFGF, 2-mercaptoethanol, and nicotinamide. In some embodiments, the concentration of 2-mercaptoethanol is no more than about 10 mmol/L, e.g., from about 0.1 to about 10 mmol/L. In some embodiments, the concentration of 2-mercaptoethanol is from about: 0.1-1, 1-2, 2-3, 3-4, 4-5, 5-6, 6-7, 7-8, 8-9, or 9-10 mmol/L. In some embodiments, the concentration of 2-mercaptoethanol is about: 0.2, 0.5, 1, 1.5, 2, 3, 4, 5, 6, 7, 8, or 9 mmol/L. In some embodiments, the 2-mercaptoethanol is about 1 mmol/L. In some embodiments, the concentration of nicotinamide is no more than about 100 mmol/L, e.g., from about 1 to about 100 mmol/L. In some embodiments, the concentration of nicotinamide is from about: 1-10, 10-20, 20-30, 30-40, 40-50, 50-60, 50-70, 80-90, or 90-100 mmol/L. In some embodiments, the concentration of nicotinamide is about: 2, 4, 6, 8, 10, 12, 14, 16, 18, 20, 30, 40, 50, 60, 70, 80, or 90 mmol/L. In some embodiments, the nicotinamide is about 10 mmol/L. In some embodiments, the mammalian trophoblast stem cell is contacted with one or more agents to regulate activity or expression level of CAMP Responsive Element Binding protein 1 (CREB1), e.g., CREB1 phosphorylation. In some embodiments, the one or more agents comprise a vitamin metabolite, e.g., retinoic acid. In some embodiments, the one or more agents comprise a CREB1-binding protein. In some embodiments, the one or more agents regulate one or more factors selected from the group consisting of mixl1, Cdx2, Oct4, Sox17, Foxa2, and GSK3β. In some embodiments, the miR-124 herein is miR-124a, miR-124b, miR-124c, miR-124d, or miR-124e, e.g., miR-124a. In some embodiments, the miR-124a is homo sapiens miR-124a (hsa-miR-124a), e.g., hsa-miR-124-5p (SEQ ID NO:1: CGUGUUCACA-GCGGACCUUGAU) or hsa-miR-124-3p (SEQ ID NO:2: UAAGGCACGCGGUGAAUGCC) or a fragment thereof. In some embodiments, the miR-124 comprises a sequence selected from Table 1 and Table 2, or a fragment thereof.

BRIEF DESCRIPTION OF THE DRAWINGS

FIG. 1A shows a time-course profile of pancreatic development-related transcription factors during hTS cell differentiation to pancreatic progenitors. Data representing mean±SD, n=3 independent experiments, *p<0.05 (t test). FIG. 1B shows changes of Mixl1 intensity during DE formation. FIG. 1C shows the segregation of mesendoderm into two cell populations: one expressing Pdx1$^+$Mixl1$^+$ for mesoderm and another expressing Pdx1$^+$Mixl1$^-$ for endoderm.

FIG. 2A shows transition of unique pluripotency transcription factors at each stage-specific cell stage. Data representing mean±SD, n=3 independent experiments, *p<0.05 (t test). FIG. 2B shows immunofluorescence images of Mixl1, Cdx2, and Oct4 during the transition of DE. FIG. 2C shows immunofluorescence images of Oct4 with the representative markers of DE stage.

FIGS. 3A-3M are a set of graphs illustrating biogenesis and multifaceted functions of miR-124a. FIG. 3A is a mechanistic illustration for regulation of DE formation and betatrophin activation. FIG. 3B shows a correlation between miR-124a and p-CREB1 expression observed over time and that active PI3K/Akt/CREB1 signaling pathway targeted different sites of miR-124a. FIG. 3C shows a parallel expression of p-CREB1 and miR-124a by qPCR assay and promoter regions of miR-124-2 containing CREB1-binding site 1 (acgccgtcatt, SEQ ID NO: 148) and site 2 (ggtgacgtcagc, SEQ ID NO:149) and of miR-124-3 containing a CREB1-binding site (ggtgacgtcacc, SEQ ID NO:150) quantified from CREB1 ChIP with qPCR. FIGS. 3D-3F show construction of plasmids for luciferase reporter assays: FIG. 3D shows pGL4.51-Luc reporter constructs for Smad4 3'UTR containing consensus-binding sites Smad4 (1) (5'-guuuguc-cagugccuuu-3', SEQ ID NO:151) and Smad4 (2) (5'-aucca-gaauugccuua-3', SEQ ID NO:152) targeting miR-124a (SEQ ID NO:2 presented in the 3 to 5 direction); FIG. 3E shows pGL4.51-Luc reporter constructs for Cdx2 3'UTR (5'-ggga-guauuugaacaca-3', SEQ ID NO:153) targeting hsa-miR-124a (5'-cguguucacagcggacc-3', SEQ ID NO:154, a fragment of SEQ ID NO:1); and FIG. 3F shows pGL4.51-Luc reporter constructs for GSK3β 3'UTR (5'-guuuggagugc-cuuc-3', SEQ ID NO:155) targeting miR-124a (5'-uaaggcacgcgguga-3 SEQ ID NO:156, a fragment of SEQ ID NO:2). Data representing mean±SD, n=5, *p<0.05 (t test). Cells transfected with non-specific shRNA were used as positive control. Empty vector was used as negative control. FIG. 3G shows effects of pre-transfection of miR124a or anti-miR-124a on the expressions of Smad4, Mixl1, Cdx2, GSK3β, and Oct4 after induction. FIG. 3H shows that Oct4 targeted gene Sox17 to produce Sox17 at 4 hr (arrow). Input: positive control, IgG: negative control. FIG. 3I shows that β-catenin targeted gene Foxa2 (cctgtttgttttagtt, SEQ ID NO:157) to apparently produce Foxa2 (arrow) in ChIP assays (4 hr). Input: positive control, IgG: negative control.

FIGS. 3J-M show synthesis and regulation of betatrophin: FIG. 3J shows that Foxa2 targeted the gene C19orf80 to produce betatrophin (arrow) by ChIP assay; and FIG. 3K shows from a qPCR analysis a transient elevation of betatrophin mRNA at 16 hr (normalized to glyceraldehyde-3-phosphate dehydrogenase). FIG. 3L is a set of Western blotting data showing a parallel correlation among betatrophin, C-peptide, and insulin. Data representing mean±SD. n=3, *p<0.05 (t test). FIG. 3M shows immunofluorescent coexpression of betatrophin and insulin by 24 hr induction.

FIGS. 4A-4C show functional glucose stimulation test in vitro. FIG. 4A shows that the cells were responsible to high glucose concentration (15 mM, gray column) to yield immunoreactive insulin by ELISA assay. FIG. 4B is a set of representative excerpts of image showing morphological changes and a positive DTZ staining recorded by a computer-microscopy-video system (Olympus, IX-81, DP30, MIU-IBC-IF-2). FIG. 4C shows that high glucose (25 mM) stimulation yielded C-peptide with 7.6 ng/hr/$10^6$ cells (represented in the upper line) and insulin with 393.8 µIU/hr/$10^6$ cells (represented in the lower line), respectively, by radioimmunoassays. Data measured by area under curve and representing mean±SD, n=5. *p<0.05 (t test). FIG. 4D is a set of ultrastructural micrographs of the grape-like cell mass after high glucose stimulation. White arrow in the middle image: desmosome junction. The bottom arrow: β-insulin granules (β-G). The two upper arrows: α-glucagon granules (α-G). N: nucleus. Im-G: immature granules. M: mitochondria. RER: rough endoplasmic reticulum. Bar scale: 1 µm. FIG. 4E shows immunofluorescence staining of pancreatic progenitor markers at 24 hr after bFGF induction in hTS cells. Control staining not shown.

DETAILED DESCRIPTION

Figure 1A:
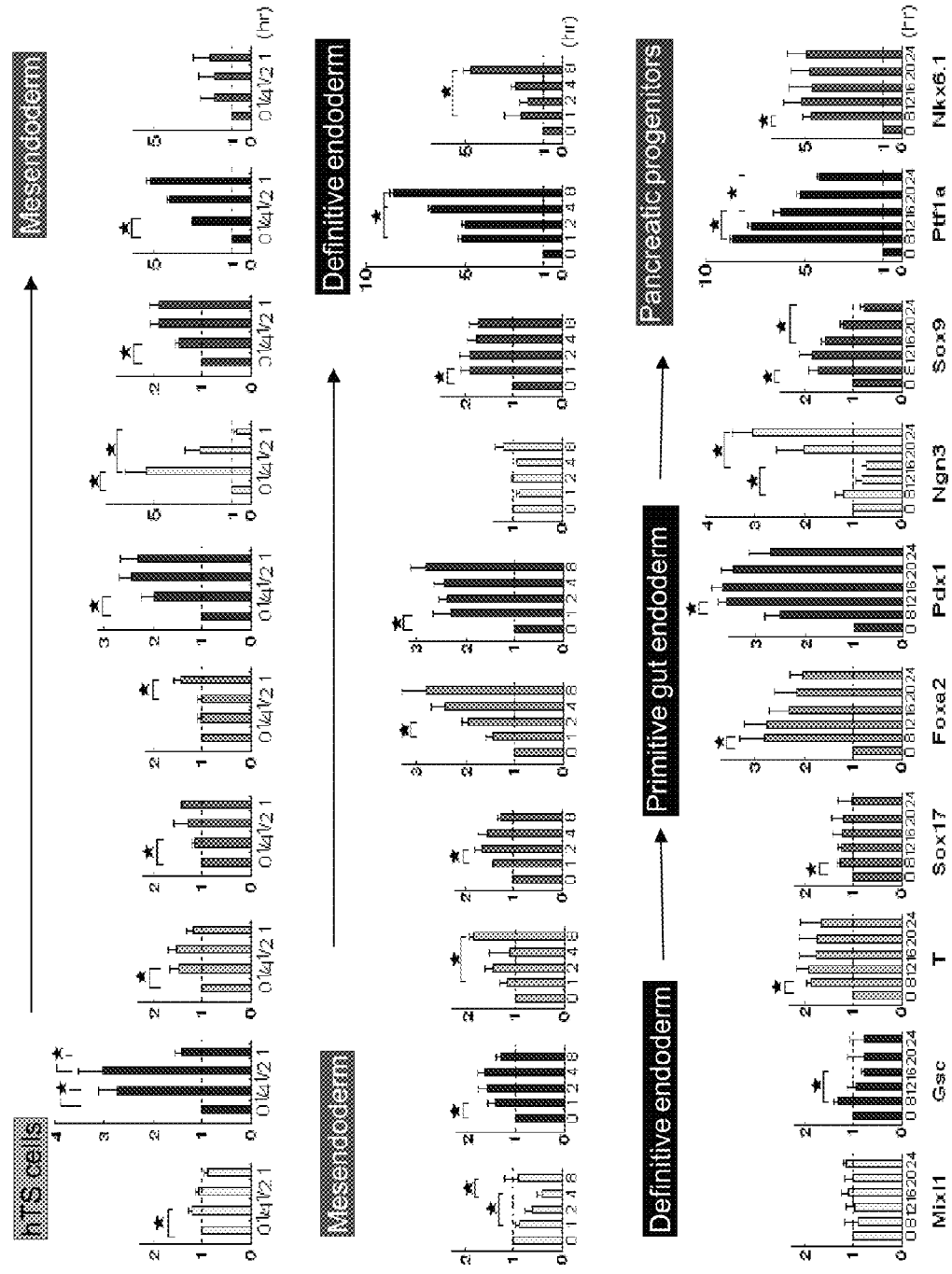
FIGS. 1A-1C are a set of graphs illustrating the path from hTS cells to pancreatic progenitors.

The details of one or more inventive embodiments are set forth in the accompanying drawings, the claims, and the description herein. Other features, objects, and advantages of the inventive embodiments disclosed and contemplated herein can be combined with any other embodiment unless explicitly excluded.

The terms "modulate" and "modulation" refer to induce or induction of, either directly or indirectly, an increase or a decrease, a stimulation, inhibition, interference, or blockage in cell activity for example cell growth or differentiation, e.g., inducing or induction of a mammalian trophoblast stem cell to become a differentiated cell for example a pancreatic progenitor.

The term "agent" refers to a compound, e.g., a biological molecule or a chemical, for use in cell growth and differentiation, e.g., differentiation of a mammalian trophoblast stem cell. Examples of the agents include but are not limited to growth factors (e.g., fibroblast growth factors (FGF)), antioxidants/reducing agents (e.g., 2-mercaptoethanol), vitamins (e.g., nicotinamide) and their metabolites (e.g., retinoic acid), nucleic acids (e.g., RNA or DNA for example microRNA), hormones, peptides, and proteins (e.g., CREB1-binding protein). Examples of the growth factors can include FGF1, FGF2 (bFGF), FGF3, FGF4, FGF5, FGF6, FGF7, FGF8, FGF9, and FGF10. More examples of the antioxidants can include 2-mercaptoethanol (2-ME), dithiothreitol (DTT), and tris(2-carboxyethyl)phosphine (TCEP). Examples of the vitamins can include vitamin A, vitamin B1, B2, B3, B5, B6, B7, B9, or B12, vitamin C, vitamin D, vitamin E, and vitamin K. In some embodiments, an agent herein regulates activity or expression level of CAMP Responsive Element Binding protein 1 (CREB1), for example CREB1 phosphorylation. In some embodiments, an agent herein activates miR124. In some embodiments, an agent herein regulates one or more transcription factors, for example mix1, Cdx2, Oct4, Sox17, Foxa2, or GSK3β.

The term "drug" is intended to include compounds having utility for therapeutic and/or diagnostic and/or prophylactic purposes, e.g., therapeutic, diagnostic or prophylactic compounds. Therapeutic compounds include, e.g., antibiotics, antivirals, antifungals, anti-angiogenics, analgesics, anesthetics, anti-inflammatory agents including steroidal and non-steroidal anti-inflammatories (NSAIDs), corticosteroids, antihistamines, mydriatics, antineoplastics, immunosuppressive agents, anti-allergic agents, metalloproteinase inhibitors, tissue inhibitors of metalloproteinases (TIMPs), inhibitors or antagonists or intraceptors, receptor antagonists, RNA aptamers, antibodies or fragments thereof, hydroxamic acids and macrocyclic anti-succinate hydroxamate derivatives, nucleic acids, plasmids, siRNAs, vaccines, DNA binding (minor groove) compounds, hormones, vitamins, proteins, peptides, polypeptides and peptide-like therapeutic agents. Diagnostic compounds include, e.g., dyes, contrast agents, fluorescent agents, radioisotopes (e.g., P-32, Tc-99, F-18, I-131) and the like that are useful in the diagnosis of diseases, conditions, syndromes or symptoms thereof. A therapeutic compound administered in advance of the detection of a disease, condition, syndrome or symptom is a prophylactic compound.

As used herein unless otherwise indicated, open terms such as "contain," "containing," "include," "including," and the like mean comprising.

Some embodiments herein contemplate numerical ranges. When a numerical range is provided, the range includes the range endpoints. Numerical ranges include all values and subranges therein as if explicitly written out.

As used herein, the term "about" means±15%. For example, the term "about 10" includes 8.5 to 11.5.

As used herein, the article "a" or "an" means one or more unless explicitly stated otherwise.

A "vector" refers to a recombinant DNA or RNA construct, such as a plasmid, a phage, recombinant virus, or other vector that, upon introduction into an appropriate host cell, results in a modification of a cell described herein. Appropriate expression vectors are well known to those with ordinary skill in the art and include those that are replicable in eukaryotic and/or prokaryotic cells and those that remain episomal or those that integrate into the host cell genome.

Construction of vectors can be achieved using techniques described in, for example, as described in Sambrook et al., 1989. In some embodiments, isolated plasmids or DNA fragments are cleaved, tailored, and religated in the form desired to generate the plasmids. If desired, analysis to confirm correct sequences in the constructed plasmids is performed using any suitable method. Suitable methods for constructing expression vectors, preparing in vitro transcripts, introducing DNA into host cells, and performing analyses for assessing gene expression and function are known. Gene presence, amplification, and/or expression are measured in a sample directly, for example, by conventional Southern blotting, Northern blotting to quantitate the transcription of mRNA, dot blotting (DNA or RNA analysis), or in situ hybridization, using an appropriately labeled probe which can be based on a sequence provided herein.

As used herein, terms such as "transfection", "transformation", and the like are intended to indicate the transfer of nucleic acid to a cell or organism in functional form. Such terms include various means of transferring nucleic acids to cells, including transfection with CaP04, electroporation, viral transduction, lipofection, delivery using liposomes, and/or other delivery vehicles.

Cells can be sorted by affinity techniques or by cell sorting (such as fluorescence-activated cell sorting) where they are labeled with a suitable label, such as a fluorophore conjugated to or part of, for example, an antisense nucleic acid molecule or an immunoglobulin, or an intrinsically fluorescent protein, such as green fluorescent protein (GFP) or variants thereof. As used herein, "sorting" refers to the at least partial physical separation of a first cell type from a second.

The terms "treating," "treatment," and the like can refer to obtaining a desired pharmacologic and/or physiologic effect, e.g., a partial or complete cure for a disorder and/or reverses an adverse effect attributable to the disorder and/or stabilizes the disorder and/or delays progression of the disorder and/or causes regression of the disorder.

Administration (e.g., transplantation) of stem cells to the area in need of treatment can be achieved by, for example and not by way of limitation, local infusion during surgery, by injection, by means of a catheter, or by means of an implant, said implant being of a porous, non-porous, or gelatinous material, including membranes, such as silastic membranes, or fibers.

"Transplanting" a composition into a mammal can refer to introducing the composition into the body of the mammal. The composition being introduced is the "transplant", and the mammal is the "recipient". The transplant and the recipient can be syngeneic, allogeneic or xenogeneic. Further, the transplantation can be an autologous transplantation.

An "effective amount" can be an amount of a therapeutic agent sufficient to achieve the intended purpose. For example, an effective amount of a factor to increase the number of hTS cells is an amount sufficient, in vivo or in vitro, as the case can be, to result in an increase in stem cell number. An effective amount of a composition to treat or ameliorate a neurodegenerative disease or condition is an amount of the composition sufficient to reduce or remove the symptoms of the neurodegenerative disease or condition. The effective amount of a given therapeutic agent will vary with factors such as the nature of the agent, the route of administration, the size and species of the animal to receive the therapeutic agent, and the purpose of the administration.

2-Mercaptoethanol (also β-mercaptoethanol, BME, 2BME, 2-ME or β-met) is the chemical compound with the formula $HOCH_2CH_2SH$.

Nicotinamide, also known as niacinamide and nicotinic acid amide, is the amide of nicotinic acid (vitamin $B_3$/niacin) and has the formula $C_6H_6N_2O$.

In some embodiments, a mammalian trophoblast stem cell herein is from a rodent (e.g., mouse, rat, guinea pig, hamster, or squirrel), rabbit, cow, sheep, pig, dog, cat, monkey, ape (e.g., chimpanzee, gorilla, or orangutan), or human.

In some embodiments, a mammal herein is a rodent (e.g., mouse, rat, guinea pig, hamster, or squirrel), rabbit, cow, sheep, pig, dog, cat, monkey, ape (e.g., chimpanzee, gorilla, or orangutan), or human.

In some embodiments, in embryogenesis, pancreatic development requires a key derivation of definitive endoderm (DE) for further differentiation. MicroRNAs (miRs) operate at many levels, controlling the timing of cellular transitions throughout the differentiation processes. One of the many aspects of the inventions is to use FGF (e.g., bFGF) for differentiating mammalian trophoblast stem cells into pancreatic progenitors via DE specification driven by miR-124. Another aspect of the inventions is to promote betatrophin for cell proliferation during pancreatic differentiation via modulation of miR-124. Another aspect of the inventions is to provide insulin-secreting pancreatic progenitors differentiated from the mammalian trophoblast stem cells.

In some embodiments, in mammalian trophoblast stem cells, FGF (e.g., bFGF) efficiently induces the differentiation towards insulin-secreting pancreatic progenitors via definitive endoderm (DE) formation in one day.

In some embodiments, FGF (e.g., bFGF) activates spatiotemporal elevation of microRNA (miR)-124 via FGFR1/PI3K/Akt/CREB1 pathway to perform two functions: 1) to inhibit Smad4 and consequently repress Mixl1 for DE formation and 2) to inhibit Cdx2 and, in turn, reciprocally activate Oct4 via autoregulatory feedback loop for DE regulation. Subsequently, DE differentiates into multipotential pancreatic progenitors through the transition of primitive gut tube. Each stage-specific cellular process is mainly regulated by a unique pluripotency transcription factor during differentiation.

In some embodiments, the mammalian trophoblast stem cell-derived pancreatic progenitors are glucose-sensitive, secreting immunoreactive C-peptide and insulin in vitro and/or in vivo.

In some embodiments, the FGF (e.g., bFGF) induction efficiently promotes activation of miRNA-124a which directs pancreatic progenitor differentiation in mammalian trophoblast stem cells.

In some embodiments, the mammalian trophoblast stem cells herein are renewable stem cell source for cell-based therapy in patients with diabetes mellitus and for drug toxicity screening.

In some embodiments, FGF (e.g., bFGF) enables to efficiently differentiate mammalian trophoblast stem cells (e.g., hTS cells) into pancreatic progenitors, providing evidence as renewable source of stem cells in the generation of insulin-secreting pancreatic progenitors for cell-based therapy in type1 DM patients.

In some embodiments, mammalian trophoblast stem cells offer the main advantages for pancreatic disease-associated drug screening because: 1) They are easy to produce enough number needed to assess in multi-well plates; 2) Cell genotype and phenotype are stable; 3) The pancreatic differentiation and proliferation are characterized and elucidated by the specification of DE; 4) The conditions by single inducer and simple medium facilitate the evaluation in toxicity screening; and 5) Very short time, e.g., one-day, to accomplish insulin-secreting beta-cell differentiation meets the requirement economically.

In one instance, treatment of the mammalian trophoblast stem cells with 10 ng/ml fibroblast growth factor (e.g., bFGF) yields approximately 10% insulin-producing cells in population, expressing pancreatic progenitor associated markers and components of islet of Langerhans. During cellular processes, miRNA-124 efficiently suppresses Cdx2 and Smad4 and its downstream effector Mixl1, directing the formation of DE and differentiating towards pancreatic progenitors. The cells are capable of glucose-stimulated insulin secretion.

In some embodiments, FGF (e.g., bFGF) activates PI3K/Akt pathway via RTK to phosphorylate CREB1. CREB1-p transiently targets promoter of miR-124. In one instance, miR-124 functions in two ways: a) to repress Smad4 and Mixl1 for DE formation; and b) to repress Cdx2 and, in turn, to activate Oct4 for DE regulation. In one instance, FGF (e.g., bFGF) induces cellular processes mediating mesendoderm, DE, and primitive gut tube to form functional pancreatic progenitor in mammalian trophoblast stem cells in one-day.

In some embodiments, a mammalian trophoblast stem cell herein is a human trophoblast stem cell (hTS cell).

miR-124a is also known as miR-124a, mir-124a, microRNA-124a, miRNA-124a, miR-124, mir-124, microRNA-124, or miRNA-124.

For miR-124, coding sequences of interest include, but are not limited to, sequences that encode precursors of miR-124, e.g., where examples of such coding sequences are reported in the miRBase database, hosted and maintained in the Faculty of Life Sciences at the University of Manchester with funding from the BBSRC. A given vector may include a single coding sequence or multiple repeats of the coding sequence, as desired.

The precursors of miR-124 can also be found in the miRBase database, e.g.,

```
>hsa-mir-124-1 MI0000443
                                (SEQ ID NO: 3)
AGGCCUCUCUCUCCGUGUUCACAGCGGACCUUGAUUUAAAUGUCCAUAC

AAUUAAGGCACGCGGUGAAUGCCAAGAAUGGGGCUG

>hsa-mir-124-2 MI0000444
                                (SEQ ID NO: 146)
AUCAAGAUUAGAGGCUCUGCUCUCCGUGUUCACAGCGGACCUUGAUUUA

AUGUCAUACAAUUAAGGCACGCGGUGAAUGCCAAGAGCGGAGCCUACGG

CUGCACUUGAA

>hsa-mir-124-3 MI0000445
                                (SEQ ID NO: 147)
UGAGGGCCCCUCUGCGUGUUCACAGCGGACCUUGAUUUAAUGUCUAUAC

AAUUAAGGCACGCGGUGAAUGCCAAGAGAGGCGCCUCC
```

The nucleic acid sequence of an miR-124 herein can include a segment or a full length of the nucleic acid sequence of any miR-124 family member, e.g., of those in the present Drawings, Table 1, and Table 2, e.g., as identified in flies (MI0000373), nematode worms (MI0000302), mouse (MI0000150), and human (MI0000443), or of those found in the miRBase: the microRNA database by the University of Manchester, UK. In some embodiments, an anti-miR-124 can have a sequence of any compliment to the sequence of miR-124, e.g., miRZIP124. In some embodiments, the anti-miR-124 is prepared using the miRZip™ lentiviral-based microRNA knockdown method, e.g., produced by System Biosciences.

TABLE 1

Examples of miR-124 family numbers

| Name | Accession | Sequence | SEQ ID NO |
|---|---|---|---|
| >hsa-miR-124-5p | MIMAT0004591 | CGUGUUCACAGCGGACCUUGAU | SEQ ID NO: 1 |
| >hsa-miR-124-3p | MIMAT0000422 | UAAGGCACGCGGUGAAUGCC | SEQ ID NO: 2 |
| >aae-miR-124 | MIMAT0014282 | UAAGGCACGCGGUGAAUGC | SEQ ID NO: 4 |
| >aca-miR-124a | MIMAT0021725 | UAAGGCACGCGGUGAAUGCCA | SEQ ID NO: 5 |
| >aca-miR-124b | MIMAT0021726 | UAAGGCACGCGGUGAAUGCUA | SEQ ID NO: 6 |
| >aga-miR-124 | MIMAT0001499 | UAAGGCACGCGGUGAAUGCCAAG | SEQ ID NO: 7 |
| >age-miR-124a | MIMAT0002466 | UUAAGGCACGCGGUGAAUGCCA | SEQ ID NO: 8 |
| >ame-miR-124 | MIMAT0001473 | UAAGGCACGCGGUGAAUGCCAAG | SEQ ID NO: 9 |
| >api-miR-124 | MIMAT0014712 | UAAGGCACGCGGUGAAUGCCA | SEQ ID NO: 10 |
| >asu-miR-124-5p | MIMAT0021495 | CGCCUUCACCGGUGACUUUGGU | SEQ ID NO: 11 |
| >asu-miR-124-3p | MIMAT0021496 | UAAGGCACGCGGUGAAUGCCA | SEQ ID NO: 12 |
| >bfl-miR-124-5p | MIMAT0019146 | AGUGUUCACGGCGGUCCUUAAU | SEQ ID NO: 13 |
| >bfl-miR-124-3p | MIMAT0009482 | UAAGGCACGCGGUGAAUGCCAA | SEQ ID NO: 14 |
| >bma-miR-124 | MIMAT0014116 | UAAGGCACGCGGUGAAUGCCAA | SEQ ID NO: 15 |
| >bmo-miR-124 | MIMAT0004198 | UAAGGCACGCGGUGAAUGCCAAG | SEQ ID NO: 16 |
| >bta-miR-124a | MIMAT0003811 | UAAGGCACGCGGUGAAUGCCAAG | SEQ ID NO: 17 |
| >bta-miR-124b | MIMAT0013774 | UAAGGCACGCGGUGAAUGCCAAG | SEQ ID NO: 18 |
| >cbr-miR-124 | MIMAT0000494 | UAAGGCACGCGGUGAAUGCCA | SEQ ID NO: 19 |
| >ccr-miR-124a | MIMAT0026331 | UCAAGGUCCGCUGUGAACAC | SEQ ID NO: 20 |
| >ccr-miR-124b | MIMAT0026334 | UCAAGGUCCGCCGUGAACACGC | SEQ ID NO: 21 |
| cel-miR-124-5p | MIMAT0015111 | GCAUGCACCCUAGUGACUUUAGU | SEQ ID NO: 22 |
| >cel-miR-124-3p | MIMAT0000282 | UAAGGCACGCGGUGAAUGCCA | SEQ ID NO: 23 |
| >cfa-miR-124 | MIMAT0006657 | UAAGGCACGCGGUGAAUGCCA | SEQ ID NO: 24 |
| >cfa-miR-124 | MIMAT0006657 | UAAGGCACGCGGUGAAUGCCA | SEQ ID NO: 25 |
| >cgr-miR-124 | MIMAT0023740 | UAAGGCACGCGGUGAAUGCCAA | SEQ ID NO: 26 |
| >cin-miR-124-1-5p | MIMAT0015256 | AGUAUUUAUUGUGGACCUUG | SEQ ID NO: 27 |
| >cin-miR-124-3p | MIMAT0006100 | UAAGGCACGCGGUGAAUGCCAA | SEQ ID NO: 28 |
| >cin-miR-124-2-5p | MIMAT0015257 | CGUGUUUACUGUGGACCUUG | SEQ ID NO: 29 |
| >cqu-miR-124 | MIMAT0014360 | UAAGGCACGCGGUGAAUGC | SEQ ID NO: 30 |
| >crm-miR-124 | MIMAT0011541 | UAAGGCACGCGGUGAAUGCC | SEQ ID NO: 31 |
| >csa-miR-124 | MIMAT0006126 | UAAGGCACGCGGUGAAUGCCAA | SEQ ID NO: 32 |
| >cte-miR-124 | MIMAT0009555 | UAAGGCACGCGGUGAAUGCCA | SEQ ID NO: 33 |
| >dan-miR-124 | MIMAT0008431 | UAAGGCACGCGGUGAAUGCCAAG | SEQ ID NO: 34 |
| >der-miR-124 | MIMAT0008547 | UAAGGCACGCGGUGAAUGCCAAG | SEQ ID NO: 35 |
| >dgr-miR-124 | MIMAT0008615 | UAAGGCACGCGGUGAAUGCCAAG | SEQ ID NO: 36 |
| >dme-miR-124-5p | MIMAT0020813 | GGUAUCCACUGUAGGCCUAUAUG | SEQ ID NO: 37 |

TABLE 1 -continued

Examples of miR-124 family numbers

| Name | Accession | Sequence | SEQ ID NO |
|---|---|---|---|
| >dme-miR-124-3p | MIMAT0000351 | UAAGGCACGCGGUGAAUGCCAAG | SEQ ID NO: 38 |
| >dmo-miR-124 | MIMAT0008688 | UAAGGCACGCGGUGAAUGCCAAG | SEQ ID NO: 39 |
| >dpe-miR-124 | MIMAT0008731 | UAAGGCACGCGGUGAAUGCCAAG | SEQ ID NO: 40 |
| >dps-miR-124 | MIMAT0001229 | UAAGGCACGCGGUGAAUGCCAAG | SEQ ID NO: 41 |
| >dpu-miR-124 | MIMAT0012639 | UAAGGCACGCGGUGAAUGCCAAG | SEQ ID NO: 42 |
| >dre-miR-124 | MIMAT0001819 | UAAGGCACGCGGUGAAUGCCAA | SEQ ID NO: 43 |
| >dse-miR-124 | MIMAT0008839 | UAAGGCACGCGGUGAAUGCCAAG | SEQ ID NO: 44 |
| >dsi-miR-124 | MIMAT0008847 | UAAGGCACGCGGUGAAUGCCAAG | SEQ ID NO: 45 |
| >dvi-miR-124 | MIMAT0008939 | UAAGGCACGCGGUGAAUGCCAAG | SEQ ID NO: 46 |
| >dwi-miR-124 | MIMAT0009027 | UAAGGCACGCGGUGAAUGCCAAG | SEQ ID NO: 47 |
| >dya-miR-124 | MIMAT0009105 | UAAGGCACGCGGUGAAUGCCAAG | SEQ ID NO: 48 |
| >eca-miR-124 | MIMAT0012906 | UAAGGCACGCGGUGAAUGCC | SEQ ID NO: 49 |
| >egr-miR-124a | MIMAT0020240 | UAAGGCACGCGGUGAAUGCCA | SEQ ID NO: 50 |
| >egr-miR-124b-5p | MIMAT0020241 | GUAUUCUACGCGAUGUCUUGGUA | SEQ ID NO: 51 |
| >egr-miR-124b-3p | MIMAT0020242 | UAAGGCACGCGGUGAAUACC | SEQ ID NO: 52 |
| >emu-miR-124a | MIMAT0020266 | UAAGGCACGCGGUGAAUGCCA | SEQ ID NO: 53 |
| >emu-miR-124b | MIMAT0020267 | UAAGGCACGCGGUGAAUACC | SEQ ID NO: 54 |
| >fru-miR-124 | MIMAT0002896 | UAAGGCACGCGGUGAAUGCCAA | SEQ ID NO: 55 |
| >gga-miR-124a | MIMAT0001128 | UUAAGGCACGCGGUGAAUGCCA | SEQ ID NO: 56 |
| >gga-miR-124b | MIMAT0001174 | UUAAGGCACGCAGUGAAUGCCA | SEQ ID NO: 57 |
| >gga-miR-124c-5p | MIMAT0025599 | CAUUCACCGCGUGCCUUAAUU | SEQ ID NO: 58 |
| >ggo-miR-124a | MIMAT0002465 | UUAAGGCACGCGGUGAAUGCCA | SEQ ID NO: 59 |
| >hco-miR-124 | MIMAT0023338 | UAAGGCACGCGGUGAAUGCCAA | SEQ ID NO: 60 |
| >hme-miR-124 | MIMAT0024937 | UAAGGCACGCGGUGAAUGCCAA | SEQ ID NO: 61 |
| >isc-miR-124 | MIMAT0012685 | UAAGGCACGCGGUGAAUGCCAAG | SEQ ID NO: 62 |
| >lgi-miR-124 | MIMAT0009578 | UAAGGCACGCGGUGAAUGCCA | SEQ ID NO: 63 |
| >lla-miR-124a | MIMAT0002471 | UUAAGGCACGCGGUGAAUGCCA | SEQ ID NO: 64 |
| >mdo-miR-124a | MIMAT0004102 | UUAAGGCACGCGGUGAAUGCCA | SEQ ID NO: 65 |
| >mml-miR-124a | MIMAT0002470 | UUAAGGCACGCGGUGAAUGCCA | SEQ ID NO: 66 |
| >mmu-miR-124-5p | MIMAT0004527 | CGUGUUCACAGCGGACCUUGAU | SEQ ID NO: 67 |
| >mmu-miR-124-3p | MIMAT0000134 | UAAGGCACGCGGUGAAUGCC | SEQ ID NO: 68 |
| >mse-miR-124 | MIMAT0024474 | UAAGGCACGCGGUGAAUGCCA | SEQ ID NO: 69 |
| >nvi-miR-124 | MIMAT0015688 | UAAGGCACGCGGUGAAUGCCAAG | SEQ ID NO: 70 |
| >oan-miR-124-5p | MIMAT0007113 | CGUGUUCACAGCGGACCUUGAU | SEQ ID NO: 71 |
| >oan-miR-124-3p | MIMAT0007114 | UAAGGCACGCGGUGAAUGCCA | SEQ ID NO: 72 |
| >odi-miR-124a | MIMAT0006082 | UAAGGCACGCGGUGAAUGCUAA | SEQ ID NO: 73 |
| >odi-miR-124b | MIMAT0006083 | UAAGGCACUCGGUGAAUGCUAA | SEQ ID NO: 74 |
| >ola-miR-124-5p | MIMAT0022689 | CGUGUUCACAGCGGACCUU | SEQ ID NO: 75 |

TABLE 1 -continued

Examples of miR-124 family numbers

| Name | Accession | Sequence | SEQ ID NO |
|---|---|---|---|
| >ola-miR-124-3p | MIMAT0022573 | UAAGGCACGCGGUGAAUGCCA | SEQ ID NO: 76 |
| >pma-miR-124-5p | MIMAT0019444 | CGUGUUCACAGCGGACCUUGAU | SEQ ID NO: 77 |
| >pma-miR-124-3p | MIMAT0019445 | UAAGGCACGCGGUGAAUGCCA | SEQ ID NO: 78 |
| >pol-miR-124-5p | MIMAT0025430 | CGUGUUCACAGCGGACCUUGAU | SEQ ID NO: 79 |
| >pol-miR-124-3p | MIMAT0025431 | UAAGGCACGCGGUGAAUGCCAA | SEQ ID NO: 80 |
| >ppa-miR-124a | MIMAT0002467 | UUAAGGCACGCGGUGAAUGCCA | SEQ ID NO: 81 |
| >ppc-miR-124 | MIMAT0011645 | UAAGGCACGCGGUGAAUGCC | SEQ ID NO: 82 |
| >ppy-miR-124 | MIMAT0015747 | UAAGGCACGCGGUGAAUGCC | SEQ ID NO: 83 |
| >ppy-miR-124a | MIMAT0002468 | UUAAGGCACGCGGUGAAUGCCA | SEQ ID NO: 84 |
| >ptr-miR-124a | MIMAT0002469 | UUAAGGCACGCGGUGAAUGCCA | SEQ ID NO: 85 |
| >rno-miR-124-5p | MIMAT0004728 | CGUGUUCACAGCGGACCUUGAU | SEQ ID NO: 86 |
| >rno-miR-124-3p | MIMAT0000828 | UAAGGCACGCGGUGAAUGCC | SEQ ID NO: 87 |
| >sja-miR-124-5p | MIMAT0016262 | CCAUUUCCGCGAUUGCCUUGAUUU | SEQ ID NO: 88 |
| >sja-miR-124-3p | MIMAT0016263 | UAAGGCACGCGGUGAAUGUCA | SEQ ID NO: 89 |
| >sko-miR-124-5p | MIMAT0009624 | AGUGUUCACAGCGGUCCUUGAU | SEQ ID NO: 90 |
| >sko-miR-124-3p | MIMAT0009625 | UAAGGCACGCGGUGAAUGCCAA | SEQ ID NO: 91 |
| >sme-miR-124a-5p | MIMAT0012112 | UGCUUUUAACGCGGAGCUUUAGU | SEQ ID NO: 92 |
| >sme-miR-124a-3p | MIMAT0003992 | UAAGGCACGCGGUGAAUGCUU | SEQ ID NO: 93 |
| >sme-miR-124b-5p | MIMAT0012113 | UGCAUUUACAACGUGUCUUUAGU | SEQ ID NO: 94 |
| >sme-miR-124b-3p | MIMAT0003993 | UAAGGCACGCGGUGAAUGCUGA | SEQ ID NO: 95 |
| >sme-miR-124c-1-5p | MIMAT0003994 | GCGCUCACCUCGUGACCUUUGU | SEQ ID NO: 96 |
| >sme-miR-124c-3p | MIMAT0003995 | UAAGGCACGCGGUGAAUGCCA | SEQ ID NO: 97 |
| >sme-miR-124c-2-5p | MIMAT0013778 | GCAUUAACCCUGUUGUCUUAGAU | SEQ ID NO: 98 |
| >sme-miR-124e-5p | MIMAT0012138 | GCCAUUCUCAGUUGGAGUCUU | SEQ ID NO: 99 |
| >sme-miR-124e-3p | MIMAT0011239 | UAAGGCACGCUGUGAAUGCCA | SEQ ID NO: 100 |
| >spu-miR-124 | MIMAT0009666 | UAAGGCACGCGGUGAAUGCCA | SEQ ID NO: 101 |
| >ssc-miR-124a | MIMAT0002156 | UAAGGCACGCGGUGAAUGCCA | SEQ ID NO: 102 |
| >ssc-miR-124a | MIMAT0002156 | UAAGGCACGCGGUGAAUGCCA | SEQ ID NO: 103 |
| >tca-miR-124-5p | MIMAT0019114 | AGUGUUCACUGUUGGCCUGUAU | SEQ ID NO: 104 |
| >tca-miR-124-3p | MIMAT0008370 | UAAGGCACGCGGUGAAUGCCAAG | SEQ ID NO: 105 |
| >tgu-miR-124-5p | MIMAT0014630 | CGUGUUCACAGCGGACCUUGA | SEQ ID NO: 106 |
| >tgu-miR-124-3p | MIMAT0014507 | UAAGGCACGCGGUGAAUGCCA | SEQ ID NO: 107 |
| >tni-miR-124 | MIMAT0002897 | UAAGGCACGCGGUGAAUGCCAA | SEQ ID NO: 108 |
| >tur-miR-124-1-5p | MIMAT0023088 | CGUGUUCACUGUGUAUGUCUUG | SEQ ID NO: 109 |
| >tur-miR-124-3p | MIMAT0023089 | UAAGGCACGCGGUGAAUGCCA | SEQ ID NO: 110 |
| >tur-miR-124-2-5p | MIMAT0026457 | GUGUUCACUGUUUGCCUUCAUG | SEQ ID NO: 111 |
| >xbo-miR-124 | MIMAT0020120 | UAAGGCACGCGGUGAAUGCCAA | SEQ ID NO: 112 |
| >xtr-miR-124 | MIMAT0003683 | UUAAGGCACGCGGUGAAUGCCA | SEQ ID NO: 113 |

TABLE 1 -continued

Examples of miR-124 family numbers

| Name | Accession | Sequence | SEQ ID NO |
|---|---|---|---|
| sme-miR-124d-3p | MIMAT0011238 | UAAGGCACGCGGUAAGUGGGU | SEQ ID NO: 114 |
| sme-miR-124d-5p | MIMAT0012137 | AACAUUUACAAGCGAGCCUUAAU | SEQ ID NO: 115 |

Note:
The sequence names in Table 1 are denoted according to standard nomenclature rules, e.g., as -5p or -3p.

TABLE 2

Examples of miR-124a family numbers

| Name | Accession | Sequence |
|---|---|---|
| hsa-miR-124-5p | MIMAT0004591 | CGUGUUCACAGCGGACCUUGAU (SEQ ID NO: 1) |
| hsa-miR-124-3p | MIMAT0000422 | UAAGGCACGCGGUGAAUGCC (SEQ ID NO: 2) |
| aca-miR-124a | MIMAT0021725 | UAAGGCACGCGGUGAAUGCCA (SEQ ID NO: 5) |
| age-miR-124a | MIMAT0002466 | UUAAGGCACGCGGUGAAUGCCA (SEQ ID NO: 8) |
| bta-miR-124a | MIMAT0003811 | UAAGGCACGCGGUGAAUGCCAAG (SEQ ID NO: 17) |
| ccr-miR-124a | MIMAT0026331 | UCAAGGUCCGCUGUGAACAC (SEQ ID NO: 20) |
| egr-miR-124a | MIMAT0020240 | UAAGGCACGCGGUGAAUGCCA (SEQ ID NO: 50) |
| emu-miR-124a | MIMAT0020266 | UAAGGCACGCGGUGAAUGCCA (SEQ ID NO: 53) |
| gga-miR-124a | MIMAT0001128 | UUAAGGCACGCGGUGAAUGCCA (SEQ ID NO: 56) |
| ggo-miR-124a | MIMAT0002465 | UUAAGGCACGCGGUGAAUGCCA (SEQ ID NO: 59) |
| lla-miR-124a | MIMAT0002471 | UUAAGGCACGCGGUGAAUGCCA (SEQ ID NO: 64) |
| mdo-miR-124a | MIMAT0004102 | UUAAGGCACGCGGUGAAUGCCA (SEQ ID NO: 65) |
| mml-miR-124a | MIMAT0002470 | UUAAGGCACGCGGUGAAUGCCA (SEQ ID NO: 66) |
| mmu-miR-124-3p | MIMAT0000134 | UAAGGCACGCGGUGAAUGCC (SEQ ID NO: 68) |
| mmu-miR-124-5p | MIMAT0004527 | CGUGUUCACAGCGGACCUUGAU (SEQ ID NO: 67) |
| odi-miR-124a | MIMAT0006082 | UAAGGCACGCGGUGAAUGCUAA (SEQ ID NO: 73) |
| ppa-miR-124a | MIMAT0002467 | UUAAGGCACGCGGUGAAUGCCA (SEQ ID NO: 81) |
| ppy-miR-124a | MIMAT0002468 | UUAAGGCACGCGGUGAAUGCCA (SEQ ID NO: 84) |
| ptr-miR-124a | MIMAT0002469 | UUAAGGCACGCGGUGAAUGCCA (SEQ ID NO: 85) |
| rno-miR-124-3p | MIMAT0000828 | UAAGGCACGCGGUGAAUGCC (SEQ ID NO: 87) |
| rno-miR-124-5p | MIMAT0004728 | CGUGUUCACAGCGGACCUUGAU (SEQ ID NO: 86) |
| sme-miR-124a-3p | MIMAT0003992 | UAAGGCACGCGGUGAAUGCUU (SEQ ID NO: 93) |
| sme-miR-124a-5p | MIMAT0012112 | UGCUUUUAACGCGGAGCUUUAGU (SEQ ID NO: 92) |
| ssc-miR-124a | MIMAT0002156 | UAAGGCACGCGGUGAAUGCCA (SEQ ID NO: 103) |

Note:
The sequence names in Table 2 are denoted according to standard nomenclature rules, e.g., as -5p or -3p.

TABLE 3

Promoter sequences of Smad4 shRNA

| Name | Target Sequence | Hairpin Sequence |
|---|---|---|
| TRCN0000040032 | GTACTTCATACCA TGCCGATT (SEQ ID NO: 116) | 5'-CCGG-GTACTTCATACCATGCCGATT-CTCGAG-AATC GGCATGGTATGAAGTAC-TTTTTG-3' (SEQ ID NO: 117) |
| TRCN0000010323 | CAGATTGTCTTGC AACTTCAG (SEQ ID NO: 118) | 5'-CCGG-CAGATTGTCTTGCAACTTCAG-CTCGAG-CTG AAGTTGCAAGACAATCTG-TTTTTG-3' (SEQ ID NO: 119) |
| TRCN0000010321 | TACCATACAGAG AACATTGGA (SEQ ID NO: 120) | 5'-CCGG-TACCATACAGAGAACATTGGA-CTCGAG-TCC AATGTTCTCTGTATGGTA-TTTTTG-3' (SEQ ID NO: 121) |

Mammalian Trophoblast Stem Cells

In some embodiments, a mammalian trophoblast stem cell herein is from rodents (e.g, mice, rats, guinea pigs, hamsters, squirrels), rabbits, cows, sheep, pigs, dogs, cats, monkeys, apes (e.g., chimpanzees, gorillas, orangutans), or humans. In one instance, a mammalian trophoblast stem cell herein is not from primates, e.g., monkeys, apes, humans. In another instance, a mammalian trophoblast stem cell herein is from primates, e.g., monkeys, apes, humans. In another instance, a mammalian trophoblast stem cell herein is human or humanized.

A mammalian trophoblast stem cell herein can be induced for differentiating into one or more kinds of differentiated cells. In one instance, the differentiated cell is a progenitor cell, e.g., a pancreatic progenitor cell. In one instance, the differentiated cell is a pluripotent stem cell. In one instance, the differentiated cell is an endodermal, mesodermal, or ectodermal progenitor cell. In one instance, the differentiated cell is a definitive endoderm progenitor cell. In one instance, the differentiated cell is a pancreatic endoderm progenitor cell. In one instance, the differentiated cell is a multipotent progenitor cell. In one instance, the differentiated cell is an oligopotent progenitor cell. In one instance, the differentiated cell is a monopotent, bipotent, or tripotent progenitor cell. In one instance, the differentiated cell is an endocrine, exocrine, or duct progenitor cell, e.g., an endocrine progenitor cell. In one instance, the differentiated cell is a beta-cell. In one instance, the differentiated cell is an insulin-producing cell. One or more differentiated cells can be used in any method disclosed herein.

In one aspect, provided herein are one or more differentiated cells isolated from one or more methods herein. In one instance, the isolated differentiated cell is a human cell. In one instance, the isolated differentiated cell has a normal karyotype. In one instance, the isolated differentiated cell has one or more immune-privileged characteristics, e.g., low or absence of CD33 expression and/or CD133 expression. One or more isolated differentiated cells disclosed herein can be used in any method disclosed herein.

In another aspect, provided herein is an isolated progenitor cell that expresses one or more transcription factors comprising Foxa2, Pdx1, Ngn3, Ptf1a, Nkx6.1, or any combination thereof. In one instance, the isolated progenitor cell expresses two, three, or four transcription factors of Foxa2, Pdx1, Ngn3, Ptf1a, Nkx6.1. In one instance, the isolated progenitor cell expresses Foxa2, Pdx1, Ngn3, Ptf1a, and Nkx6.1. In one instance, the isolated progenitor cell is an induced pluripotent stem cell. In one instance, the isolated progenitor cell is derived from a mammalian trophoblast stem cell, e.g., an hTS cell. In one instance, the isolated progenitor cell is a pancreatic progenitor cell. In one instance, the isolated progenitor cell is an endodermal, mesodermal, or ectodermal progenitor cell. In one instance, the isolated progenitor cell is a definitive endoderm progenitor cell. In one instance, the isolated progenitor cell is a pancreatic endoderm progenitor cell. In one instance, the isolated progenitor cell is a multipotent progenitor cell. In one instance, the isolated progenitor cell is an oligopotent progenitor cell. In one instance, the isolated progenitor cell is a monopotent, bipotent, or tripotent progenitor cell. In one instance, the isolated progenitor cell is an endocrine, exocrine, or duct progenitor cell, e.g., an endocrine progenitor cell. In one instance, the isolated progenitor cell is a beta-cell. In one instance, the isolated progenitor cell is an insulin-producing cell. In one instance, the isolated progenitor cell is from rodents (e.g, mice, rats, guinea pigs, hamsters, squirrels), rabbits, cows, sheep, pigs, dogs, cats, monkeys, apes (e.g., chimpanzees, gorillas, orangutans), or humans. In one instance, the isolated progenitor cell is a human cell. In one instance, the isolated progenitor cell has a normal karyotype. In one instance, the isolated progenitor cell has one or more immune-privileged characteristics, e.g., low or absence of CD33 expression and/or CD133 expression. An isolated progenitor cell disclosed herein can be used in any method disclosed herein.

In another aspect, provided herein is an isolated progenitor cell that expresses betatrophin, betatrophin mRNA, C-peptide, and insulin, wherein the isolated progenitor cell is differentiated from a mammalian trophoblast stem cell. In one instance, the isolated progenitor cell is from rodents (e.g, mice, rats, guinea pigs, hamsters, squirrels), rabbits, cows, sheep, pigs, dogs, cats, monkeys, apes (e.g., chimpanzees, gorillas, orangutans), or humans. In one instance, the isolated progenitor cell is a pancreatic progenitor cell. In one instance, the isolated progenitor cell is a human cell. In one instance, the isolated progenitor cell has a normal karyotype. In one instance, the isolated progenitor cell has one or more immune-privileged characteristics, e.g., low or absence of CD33 expression and/or CD133 expression. One or more isolated progenitor cells disclosed herein can be used in any method disclosed herein.

In one instance, an isolated progenitor cell herein is an insulin-producing cell. One or more isolated progenitor cells herein can be used in any method disclosed herein.

In one instance, a differentiated cell herein is an insulin-producing cell. One or more differentiated cells herein can be used in any method disclosed herein.

Human Trophoblast Stem Cells

Human fallopian tubes are the site of fertilization and the common site of ectopic pregnancies in women, where several biological events take place such as the distinction between inner cell mass (ICM) and trophectoderm and the switch from totipotency to pluripotency with the major epigenetic changes. These observations provide support for fallopian tubes as a niche reservoir for harvesting blastocyst-associated stem cells at the preimplantation stage. Ectopic pregnancy accounts for 1 to 2% of all pregnancies in industrialized countries and are much higher in developing countries. Given the shortage in availability of human embryonic stem cells (hES cells) and fetal brain tissue, described herein is the use of human trophoblast stem cells (hTS cells) derived from ectopic pregnancy as a substitution for scarcely available hES cells for generation of progenitor cells.

In some embodiments, the hTS cells derived from ectopic pregnancies do not involve the destruction of a human embryo. In another instance, the hTS cells derived from ectopic pregnancies do not involve the destruction of a viable human embryo. In another instance, the hTS cells are derived from trophoblast tissue associated with non-viable ectopic pregnancies. In another instance, the ectopic pregnancy cannot be saved. In another instance, the ectopic pregnancy would not lead to a viable human embryo. In another instance, the ectopic pregnancy threatens the life of the mother. In another instance, the ectopic pregnancy is tubal, abdominal, ovarian or cervical.

In some embodiments, during blastocyst development, ICM contact per se or its derived diffusible 'inducer' triggers a high rate of cell proliferation in the polar trophectoderm, leading to cell movement toward the mural region throughout the blastocyst stage and can continue even after the distinction of the trophectoderm from the ICM. The mural trophectoderm cells overlaying the ICM are able to retain a 'cell memory' of ICM. Normally, at the beginning of implantation the mural cells opposite the ICM cease division because of the mechanical constraints from the uterine endometrium. However, no such constraints exist in the fallopian tubes, resulting in the continuing division of polar trophectoderm cells to form extraembryonic ectoderm (ExE) in the stagnated blastocyst of an ectopic pregnancy. In some embodiments, the ExE-derived TS cells exist for at least a 4-day window in a proliferation state, depending on the interplay of ICM-secreted fibroblast growth factor 4 (FGF4) and its receptor fibroblast growth factor receptor 2 (Fgfr2). In another instance, the ExE-derived TS cells exist for at least a 1-day, at least a 2-day, at least a 3-day, at least a 4-day, at least a 5-day, at least a 6-day, at least a 7-day, at least a 8-day, at least a 9-day, at least a 10-day, at least a 11-day, at least a 12-day, at least a 13-day, at least a 14-day, at least a 15-day, at least a 16-day, at least a 17-day, at least a 18-day, at least a 19-day, at least a 20-day window in a proliferation state. Until clinical intervention occurs, these cellular processes can yield an indefinite number of hTS cells in the preimplantation embryos; such cells retaining cell memory from ICM, reflected by the expression of ICM-related genes.

One aspect provided herein describes the distinction between hTS cells and placenta derived mesenchymal stem (PDMS) cells, using the Affymetrix™ platform to interrogate the GeneChip Human Genome U133 plus 2.0 GeneChip for a global gene comparison between hTS cells and PDMS cells. In some embodiments, the hTS cells exhibited about 10%, about 15%, about 20%, about 25%, about 30%, about 35%, about 40%, about 45%, about 50%, about 55%, about 60%, about 65% about 70%, or about 75% less gene expression than that in PDMS cells. In another instance, the hTS cells exhibited total 2,140 genes (fold change>2-fold) which is about 40% less than that in PDMS cells (3,730 genes). In some embodiments, the gene intensity distribution of hTS cells displayed a homogenous pattern distinct from that in PDMS cells. In another instance, the hTS cells represent a distinct group of cytotrophoblasts at a stage of pre-implantation, whereby they possess molecular portraits of inner cell mass (ICM) and/or trophectoderm. In another instance, the hTS cells exhibit characteristics of pluripotency and self-renewal similar to that of hES cells.

Methods of Obtaining and Isolating Mammalian Trophoblast Stem Cells

In some embodiments, a mammalian trophoblast stem cell herein (e.g., an hTS cell) can be isolated from umbilical cord, amniotic fluid, amniotic membrane, the Wharton's jelly, the chorionic villi, placenta, or ectopic pregnancy.

In one instance, a mammalian trophoblast stem cell herein (e.g., an hTS cell) can be isolated from amniocentesis biopsies or from amniotic fluid. In one instance, amniocentesis can be a procedure used to obtain a small sample of the amniotic fluid that surrounds the fetus during pregnancy. In one instance, an amniocentesis can be offered to women between the 15th and 20th weeks of pregnancy who are at increased risk for chromosome abnormalities, e.g., women who are over 35 years of age at delivery, or those who have had an abnormal maternal serum (blood) screening test indicating an increased risk for a chromosomal abnormality or neural tube defect. In one instance, a needle, e.g., a long, thin, hollow needle, can be used with ultrasound guide through your abdomen, into the uterus and the amniotic sac. A predetermined amount of amniotic fluid, e.g. one ounce, can be drawn into a syringe.

In another instance, a mammalian trophoblast stem cell herein (e.g., an hTS cell) can be obtained from blastomere biopsy during preimplantation genetic diagnosis (PGD), e.g., in conjunction with reproductive therapies such as in vitro fertilization (IVF). In one instance, the cells herein can be produced by methods for biopsy of a blastocyst, wherein the remainder of the blastocyst is implanted and results in a pregnancy and later in a live birth, e.g., the zona pellucida is removed from the blastocyst and then the blastocyst is biopsied.

In another instance, a mammalian trophoblast stem cell herein (e.g., an hTS cell) can be obtained from prenatal chorionic villus sampling (CVS). In one instance, CVS can be a prenatal test that involves taking a sample of tissue from the placenta to test for chromosomal abnormalities and certain other genetic problems. In one instance, CVS can be performed between the 10th and 12th weeks of pregnancy. In one instance, the CVS procedure is transcervical, e.g., a catheter is inserted through the cervix into the placenta to obtain the tissue sample. In one instance, the CVS procedure is transabdominal, e.g., a needle is inserted through the abdomen and uterus into the placenta to obtain the tissue sample.

In one instance, a mammalian trophoblast stem cell herein (e.g., an hTS cell) can be obtained from placental biopsies after full-term pregnancies. In one instance, a mammalian trophoblast stem cell herein (e.g., an hTS cell) herein can be isolated from a placenta after a vaginal delivery or a cesarean section delivery.

In some embodiments, a mammalian trophoblast stem cell herein (e.g., an hTS cell) can be isolated from first trimester chorionic villous sampling (e.g., $8^{+3}$ to $12^{+0}$ weeks gestational age) or term placenta from caesarean section deliveries. The chorionic tissue can be separated from the amnion, minced, and/or enzymatically digested (e.g., with 0.05% trypsin EDTA, e.g., for 20 min). Cells are subsequently centrifuged (e.g., at 1500 rpm, e.g., for 5 min), counted, and/or replated (e.g., 104 cells per cm$^2$) in a medium (e.g., Dulbecco's modified Eagle's medium+10% fetal bovine serum). In one instance, isolated cells can be plastic adherent. In one instance, the cells can be used at passage 4-8.

In one instance, a mammalian trophoblast stem cell herein (e.g., an hTS cell) can be isolated from term (e.g., 38-40 weeks' gestation) placentas according to the following procedure. Umbilical cord blood is allowed to drain from the placentas, which are then dissected carefully. The harvested pieces of tissue are washed several times (e.g., in phosphate-buffered saline) and then minced (e.g., mechanically) and enzymatically digested (e.g., with 0.25% trypsin-EDTA). The homogenate is subsequently pelleted by centrifugation and suspended in complete medium (e.g., Dulbecco's modified Eagle's medium supplemented by 10% fetal bovine serum, 100 U/ml penicillin, and/or 100 g/ml streptomycin). Cell cultures are maintained at a suitable condition, e.g., 37° C. with a water-saturated atmosphere and 5% $CO_2$. Medium is replaced periodically, e.g., one to two times every week. When cells are reach a desired level of confluence, e.g., more than 80% confluence, they are recovered, e.g., with 0.25% trypsin/EDTA, and replated at a dilution, e.g., of 1:3.

In another instance, a mammalian trophoblast stem cell herein (e.g., an hTS cell) can be isolated from human placentas following delivery according to a procedure as follows. The chorion is separated from the amnion by peeling them apart. The decidual tissue are scrapped (e.g., mechanically) and washed (e.g., in Dulbecco's phosphate-buffered salin) before being cut into small pieces (e.g., –2×2 cm). The chorion are chopped into small pieces and subjected in to an enzyme (e.g., 0.5% trypsin-EDTA, e.g., for 5 min), followed by digestion with collagenase I (e.g., at 0.3% in 37° C. incubator for 20 to 30 min). The mobilized cells are then collected and passed through a cell strainer (e.g., 100 μm). The filtered cells are collected by centrifugation (e.g., at 2,500 rpm, e.g., for 5 min). The cells are resuspended in a medium (e.g., α-modified minimum essential medium supplemented with 10% fetal bovine serum and/or 1% penicillin-streptomycin), and cultured in a container, e.g., T25 flasks, at a suitable condition (e.g., at 37° C. and/or 5% $CO_2$). The media is changed periodically, e.g., every 3 days, until the chorionic MSCs reached a desired level of confluency, e.g., 70% confluency.

In another instance, provided herein is also a method for obtaining mammalian trophoblast stem cells (e.g., hTS cells) comprising (a) obtaining am embryo at a fallopian tube of ectopic pregnancy (e.g., 4-6, 5-7, or 6-8 weeks of gestation); and (b) obtaining the stem cells from the villous trophoblast of the embryo. In some embodiments, an embryo can be obtained from an unruptured ectopic pregnancy. In some embodiments, the unruptured ectopic pregnancy can be in the stage less than 6 weeks postfertilization. The villous trophoblast can comprise cytotrophoblastic layer.

In another instance, embryonic chorionic villi can be obtained from the fallopian tubes of un-ruptured pre-implantation embryos in women with ectopic pregnancy (e.g., gestational age: 5-7 weeks). Tiny villous tissues can be well-minced in a suitable medium (e.g., serum-free α-MEM) and identified under microscopy followed by trypsinization (e.g., with 0.025% trypsin/EDTA) for a period of time (e.g., 15 min) and by adding a medium (e.g., α-MEM containing 10% FBS) to halt the reaction. Adherent cells can be obtained and cultured in a suitable condition, e.g., in conditioned α-MEM, 10% FBS, and 1% penicillin-streptomycin at 37° C. in 5% $CO_2$). After two passages, the level of hCG can become undetectable measured by a commercial kit (e.g., Dako, Carpinteria, Calif.).

Methods of Differentiation of Mammalian Trophoblast Stem Cells

In one of many aspects, provided herein is a method of differentiating a mammalian trophoblast stem cell comprising modulating miR-124 to induce differentiation of the mammalian trophoblast stem cell to a differentiated cell. In one instance, the mammalian trophoblast stem cell is a human trophoblast stem (hTS) cell. In one instance, the differentiated cell is a pluripotent stem cell. In one instance, the differentiated cell is a progenitor cell, e.g., a pancreatic progenitor cell. In one instance, the differentiated cell is an endodermal, mesodermal, or ectodermal progenitor cell, e.g., a definitive endoderm progenitor cell. In one instance, the differentiated cell is a pancreatic endoderm progenitor cell. In one instance, the differentiated cell is a multipotent progenitor cell. In one instance, the differentiated cell is an oligopotent progenitor cell. In one instance, the differentiated cell is a monopotent, bipotent, or tripotent progenitor cell. In one instance, the differentiated cell is an endocrine, exocrine, or duct progenitor cell, e.g., an endocrine progenitor cell. In one instance, the differentiated cell is a beta-cell. In one instance, the differentiated cell is an insulin-producing cell. One or more differentiated cells can be used in any method disclosed herein.

In some embodiments, a mammalian trophoblast stem cell herein is from rodents (e.g, mice, rats, guinea pigs, hamsters, squirrels), rabbits, cows, sheep, pigs, dogs, cats, monkeys, apes (e.g., chimpanzees, gorillas, orangutans), or humans.

In some embodiments, the modulating activates miR-124. In one instance, the modulating activates miR-124 spatiotemporarily, e.g., between about 1 hour to about 8 hours, at a definitive endoderm stage. In one instance, the modulating elevates miR-124 expression. In one instance, the modulating deactivates miR-124. In one instance, the modulating decreases miR-124 expression. In one instance, the modulating comprises contacting the mammalian trophoblast stem cell with one or more agents, e.g., proteins or steroid hormones. In one instance, the one or more agents comprise a growth factor, e.g., a fibroblast growth factor (FGF). In one instance, the FGF is one or more of FGF1, FGF2, FGF3, FGF4, FGF5, FGF6, FGF7, FGF8, FGF9, or FGF10. In one instance, the one or more agents comprise FGF2 (basic fibroblast growth factor, bFGF). In one instance, the modulating comprises contacting the mammalian trophoblast stem cell with no more than about 200 ng/mL of FGF (e.g., bFGF), e.g., from 100 to 200 ng/mL. In one instance, the modulating comprises contacting the mammalian trophoblast stem cell with no more than about 100 ng/mL of FGF (e.g., bFGF), e.g., from about 0.1 to 1 ng/mL; or from about 1 to about 100 ng/mL of FGF (e.g., bFGF). In one instance, the concentration of FGF (e.g., bFGF) used herein is from about: 0.1-1, 1-10, 10-20, 20-30, 30-40, 40-50, 50-60, 50-70, 80-90, or 90-100 ng/mL. In one instance, the concentration of FGF (e.g., bFGF) used herein is about: 0.1, 0.2, 0.4, 0.6, 0.8, 1, 2, 3, 4, 5, 6, 7, 8, 9, 10, 11, 12, 13, 14, 15, 16, 17, 18, 19, 20, 25, 30, 35, 40, 45, 50, 60, 70, 80, or 90 ng/mL. In one instance, the one or more agents further comprise an antioxidant or reducing agent (e.g., 2-mercaptoethanol). In one instance, the one or more agents further comprise a vitamin (e.g., nicotinamide). In one instance, the modulating comprises contacting the mammalian trophoblast stem cell with FGF (e.g., bFGF), 2-mercaptoethanol, and nicotinamide. In one instance, the concentration of antioxidant/reducing agent (e.g., 2-mercaptoethanol) is no more than about 10 mmol/L, e.g., from about 0.1 to about 10 mmol/L. In one instance, the concentration of antioxidant/reducing agent (e.g., 2-mercaptoethanol) is from about: 0.1-1, 1-2, 2-3, 3-4, 4-5, 5-6, 6-7, 7-8, 8-9, or 9-10 mmol/L. In one instance, the concentration of antioxidant/reducing agent (e.g., 2-mercaptoethanol) is about: 0.2, 0.5, 1, 1.5, 2, 3, 4, 5, 6, 7, 8, or 9 mmol/L. In one instance, the concentration of antioxidant/reducing agent (e.g., 2-mercaptoethanol) is about 1 mmol/L. In one instance, the concentration of vitamin (e.g., nicotinamide) is no more than about 100 mmol/L, e.g., from about 1 to about 100 mmol/L. In one instance, the concentration of vitamin (e.g., nicotinamide) is from about: 1-10, 10-20, 20-30, 30-40, 40-50, 50-60, 50-70, 80-90, or 90-100 mmol/L. In one instance, the concentration of vitamin (e.g., nicotinamide) is about: 2, 4, 6, 8, 10, 12, 14, 16, 18, 20, 30, 40, 50, 60, 70, 80, or 90 mmol/L. In one instance, the concentration of vitamin (e.g., nicotinamide) is about 10 mmol/L.

In one instance, the modulating comprises contacting the mammalian trophoblast stem cell with one or more agents to regulate activity or expression level of cAMP Responsive Element Binding Protein 1 (CREB1). In one instance, the one or more agents regulate CREB1 phosphorylation. In one instance, the one or more agents comprise a vitamin metabolite, e.g., retinoic acid. In one instance, the one or more agents comprise a CREB1-binding protein. In one instance, the one or more agents regulate one or more factors comprising mixl1, Cdx2, Oct4, Sox17, Foxa2, or GSK3β.

In one instance, the one or more agents comprise an exogenous miR-124 precursor or an exogenous anti-miR-124. In one instance, the mammalian trophoblast stem cell is transfected with the exogenous miR-124 precursor or the exogenous anti-miR-124. In one instance, cis-regulatory element (CRE) of TGACGTCA (SEQ ID NO: 158) of promoters of the miR-124 is modulated.

In some embodiments, the miR-124 is miR-124a, miR-124b, miR-124c, miR-124d, or miR-124e. In one instance, the miR-124 is miR-124a, e.g., *homo sapiens* miR-124a (hsa-miR-124a). In one instance, the miR-124a is hsa-miR-124-5p (SEQ ID NO:1: CGUGUUCACAGCGGAC-CUUGAU) or a fragment thereof. In one instance, the miR-124a is hsa-miR-124-3p (SEQ ID NO:2: UAAGGCACGCGGUGAAUGCC) or a fragment thereof. In one instance, the miR-124 comprises a sequence selected from Table 1, Table 2, and the Drawings, or a fragment thereof.

In one instance, the mammalian trophoblast stem cell differentiates into the differentiated cell within one day after the start of the modulating.

In some embodiments, induction of differentiation of mammalian trophoblast stem cells comprises culturing an undifferentiated mammalian trophoblast stem cell in a medium comprising a growth factor (e.g., bFGF) under conditions (e.g., 12, 24, 48, 76, or 96 hours) sufficient to induce the differentiation. The medium can further comprise serum (e.g., FBS), carbohydrates (e.g., glucose), antioxidants/reducing agents (e.g., β-mercaptonethanol), and/or vitamins (e.g., nicotinamide). Yield of the differentiated cells is measured, e.g., insulin$^+$/Ngn3$^+$ cells or insulin$^+$/glucagon$^+$ cells as indicators for pancreatic progenitors. In one instance, FBS and insulin levels are positively correlated during FGF (e.g., bFGF) induction, e.g., as indicated by Western blot analysis.

In some embodiments, upon cell induction (e.g, by bFGF), a time-course analysis, e.g, for 4, 8, 16, 24, 32, 40, or 48 hours, can be conducted to monitor levels of transcription factors identifying the cascading stages of cell differentiation development. In some embodiments, declining Mixl1 and high levels of T and Gsc may imply an transition from the mammalian trophoblast stem cells to mesendoderm. In some embodiments, dominant pluripotency transcription factors at each stage of differentiation include Cdx2 for mesendoderm, Oct4 or Nanog for DE, Cdx2 or Nanog for primitive gut endoderm, or Sox2 for pancreatic progenitors. In some embodiments, FGF (e.g., bFGF) induces multifaceted functions of miR-124a via upregulation of Oct4, Sox17, or Foxa2, but downregulation of Smad4 or Mixl1 at the DE stage.

In some embodiments, during cell differentiation, levels of proteins or hormones characteristic to the target differentiated cells are also measured with a time-course analysis, e.g., for 4, 8, 16, 24, 32, 40, or 48 hours. For example, betatrophin, C-peptide, and insulin are measured, e.g., with qPCR analysis, for pancreatic progenitor production.

In some embodiments, a growth factor is used herein to induce differentiation of a mammalian trophoblast stem cell. In one instance, the growth factor is FGF (e.g., bFGF), bone morphogenetic protein (BMP), or vascular endothelial growth factor (VEGF). In some embodiments, an effective amount of a growth factor is no more than about 100 ng/ml, e.g., about: 1, 2, 5, 10, 15, 20, 25, 30, 35, 40, 45, 50, 60, 70, 80, 90, or 100 ng/mL. In one instance, the mammalian trophoblast stem cell is an hTS cell.

In some embodiments, a culture medium herein to differentiate a mammalian trophoblast stem cell can further comprise an effective amount of a second agent that works synergistically with a first agent to induce differentiation into a mesendoderm direction. In some embodiments, the first and second agents are different growth factors. In some embodiments, the first agent is added to the culture medium before the second agent. In some embodiments, the second agent is added to the culture medium before the first agent. In one instance, the first agent is FGF (e.g., bFGF). In some embodiments, the second agent is BMP, e.g., BMP2, BMP7, or BMP4, added before or after the first agent. In some embodiments, an effective amount of a BMP is no more than about 100 ng/ml, e.g., about: 1, 2, 5, 10, 15, 20, 25, 30, 35, 40, 45, 50, 60, 70, 80, 90, or 100 ng/mL. In one instance, the mammalian trophoblast stem cell is an hTS cell.

In some embodiments, a culture medium herein to differentiate a mammalian (e.g., human) trophoblast stem cell can comprise feeder cells. Feeder cells are cells of one type that are co-cultured with cells of another type, to provide an environment in which the cells of the second type can grow.

In some embodiments, a culture medium used herein is free or essentially free of feeder cells.

In some embodiments, a GSK-3 inhibitor is used to induce differentiation of a mammalian (e.g., human) trophoblast stem cell.

Pharmaceutical Compositions and Administration

In some embodiments, provided herein is a composition comprising differentiated cells herein. In one instance, the composition further comprises a buffer solution or a pharmaceutical acceptable carrier, which is provided to maintain the bioactivities of the mammalian trophoblast stem cell (e.g., hTS cell). For example but not limiting, the buffer solution is saline, PBS (Phosphate buffered saline), or FBS (Fetal Bovine Serum) buffer.

In some embodiments, the composition herein further comprises a therapeutic compound. For example but not limiting, the therapeutic compound is a chemical or antibody or fragment thereof.

In some embodiments, the compositions herein can be administered by injection, transplantation or surgical operation.

In some embodiments, the patient is a mammal. In some embodiments, the mammal herein is a rodent (e.g., mouse, rat, guinea pig, hamster, or squirrel), rabbit, cow, sheep, pig, dog, cat, monkey, ape (e.g., chimpanzee, gorilla, or orangutan), or human. In one instance, the patient is human.

In some embodiments, provided herein is a composition for treating or preventing diabetes comprising a mammalian trophoblast stem cell (e.g., hTS cell) or the differentiated cell as described above. In one instance, the mammalian trophoblast stem cell (e.g., hTS cell) is obtained from embryo of ectopic pregnancy. The diabetes is Type1 diabetes, Type 2 diabetes, or latent autoimmune diabetes in adults (LADA).

In some embodiments, provided herein is a composition for treating or preventing a nervous system disease comprising a mammalian trophoblast stem cell (e.g., hTS cell) or the differentiated cell. In one instance, a mammalian trophoblast stem cell herein is obtained from an embryo of ectopic pregnancy. The nervous system disease is neurodegenerative disease. Neurodegenerative diseases can refer to any condition characterized by the progressive loss of neurons, due to cell death, in the central nervous system of a subject. In one instance, the neurodegenerative disease is Parkinson's disease, Huntington's disease, Alzheimer's disease, amyotrophic lateral sclerosis (ALS), multiple system atrophy, Lewy body dementia, peripheral sensory neuropathies or spinal cord injuries. In one instance, the disease neurodegenerative disease is Parkinson's disease.

Modes of administration of an isolated stem cell preparation described herein include, but are not limited to, systemic intravenous injection and injection directly to the intended site of activity. The preparation can be administered by any convenient route, for example, by infusion or bolus injection, and can be administered together with other biologically active agents. In one instance, administration is systemic localized administration.

In some embodiments, a stem cell preparation or composition is formulated as a pharmaceutical composition adapted for intravenous administration to mammal, including human beings. In one instance, a composition for intravenous administration is a solution in sterile isotonic aqueous buffer. Where necessary, the composition also includes a local anesthetic to ameliorate any pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients are mixed prior to administration.

In some embodiments, suitable pharmaceutical compositions comprise a therapeutically effective amount of the progenitor stem cells and a pharmaceutically acceptable carrier or excipient. Such a carrier includes, but is not limited to, saline, buffered saline, dextrose, water, and combinations thereof.

In some embodiments, the isolated stem cells are delivered to a targeted site (e.g., the pancreas, the brain, the spinal cord or any other site of nerve injury and/or degeneration) by a delivery system suitable for targeting cells to a particular tissue. For example, the cells are encapsulated in a delivery vehicle that allows for the slow release of the cell(s) at the targeted site. The delivery vehicle is modified such that it is specifically targeted to a particular tissue. The surface of the targeted delivery system is modified in a variety of ways. In the case of a liposomal-targeted delivery system, lipid groups are incorporated into the lipid bi-layer of the liposome in order to maintain the targeting ligand in stable association with the liposomal bi-layer.

In another example, a colloidal dispersion system is used. Colloidal dispersion systems include macromolecule complexes, nanocapsules, microspheres, beads, and lipid-based systems, including oil-in-water emulsions, micelles, mixed micelles, and liposomes.

In some embodiments, the administration of stem cells described herein is optionally tailored to an individual, by: (1) increasing or decreasing the amount cells injected; (2) varying the number of injections; (3) varying the method of delivery of the cells; or (4) varying the source of cells, e.g., by genetically engineering cells, or from in vitro cell culture.

In some embodiments, the stem cell preparation is used in an amount effective to promote engraftment of cells in the recipient. At the physician's discretion, the administration is adjusted to meet optimal efficacy and pharmacological dosing.

Methods of Screening

Provided herein are methods of screening a compound for use in treatment or prevention of a disease. In one instance, the method comprises contacting an isolated mammalian trophoblast stem cell or a differentiated cell thereof with said compound. In another instance, the method further comprises detecting a change in the activity of at least one gene, transcript or protein in the mammalian trophoblast stem cell or the differentiated cell. In another instance, the method further comprises detecting a change in the level of at least one transcript or protein in the mammalian trophoblast stem cell or the differentiated cell. In another instance, the method comprises detecting a change in the activity of at least one gene, transcript or protein in the mammalian trophoblast stem cell or the differentiated cell. In some embodiments, the disease is associated with insulin disorder, e.g., diabetes. In some embodiments, the mammalian trophoblast stem cell is an hTS cell. In some embodiments, the differentiated cell is a pancreatic progenitor cell. In some embodiments, the differentiated cell is an insulin-producing cell.

One instance provided herein describes a method of screening a compound for ability to modulate changes in a cell. In another instance, the method comprises contacting an isolated mammalian trophoblast stem cell (e.g., hTS cell) with the compound and detecting an induction of growth and differentiation of the mammalian trophoblast stem cell. In one instance, the method comprises contacting a differentiated cell (e.g., progenitor cell) herein with the compound and detecting changes in cell proliferation or cell function. In some embodiments, the isolated progenitor cell is a pancreatic progenitor cell. In some embodiments, the isolated progenitor cell is an insulin-producing cell.

In some embodiments, provided herein is a method of screening a compound for its ability to modulate pancreatic cell function (e.g., beta-cell function), comprising combining the compound with a pancreatic progenitor cell or differentiated cell herein, determining any phenotypic or metabolic changes in the cell, and correlating the change with an ability of the compound to modulate secretion of insulin, glucagon, or betatrophin.

Also provided herein is a method of screening a compound for cellular toxicity of the cell, the method comprising contacting a differentiated cell herein with the compound. In another instance, the method further comprises determining any phenotypic or metabolic changes in the cell that result from contact with the compound, and correlating the change with cellular toxicity or any other change in cell function or biochemistry. In another instance, screening of therapeutic compounds, toxins, or potential modulators of differentiation is facilitated. These substances (e.g., therapeutic compounds, toxins, or potential modulators) can be added to the culture medium.

Also provided herein is a method of screening proliferation factors, differentiation factors, and therapeutic compounds. In one instance, mammalian trophoblast stem cell is used to screen for factors (such as small molecule drugs, peptides, polynucleotides, and the like) or conditions (such as culture conditions or manipulation) that affect the characteristics of the mammalian trophoblast stem cell or differentiated cell in culture. In one instance, this system has the advantage of not being complicated by a secondary effect caused by perturbation of the feeder cells by the test compound. In another instance, growth affecting substances are tested. In another instance, the conditioned medium is withdrawn from the culture and a simpler medium is substituted. In another instance, different wells are then treated with different cocktails of soluble factors that are candidates for replacing the components of the conditioned medium. Efficacy of each mixture is determined if the treated cells are maintained and proliferate in a satisfactory manner, optimally as well as in conditioned medium. Potential differentiation factors or conditions can be tested by treating the cell according to the test protocol, and then determining whether the treated cell develops functional or phenotypic characteristics of a differentiated cell of a particular lineage. In some embodiments, the mammalian trophoblast stem cell is an hTS cell.

In some embodiments, a mammalian trophoblast stem cell (e.g., hTS cell) herein is used to screen potential modulators of cellular differentiation. In one instance, the cellular differentiation is pancreatic differentiation. For example, in one assay for screening modulators of cellular differentiation, the mammalian trophoblast stem cell can be cultured under serum free, low density conditions in the presence or absence of LIF, in the present of the modulator, and in the present or absence of RA, as the situation requires, and the effect on differentiation can be detected. In another instance, the screening methods described herein can be used to study conditions associated with cellular development and screen for potential therapeutic or corrective drugs or modulators of the condition. For example, in one instance, the development of the normal mammalian trophoblast stem cell is compared with the development with cells having the condition. In some embodiments, the mammalian trophoblast stem cell is an hTS cell.

In some embodiments, gene and protein expression can be compared between different cell populations obtained from mammalian trophoblast stem cells (e.g., hTS cells), and used to identify and characterize factors upregulated or downregulated in the course of differentiation, and produce nucleotide copies of the affected genes.

In some embodiments, feeder-free mammalian trophoblast stem cell cultures can also be used for the testing of pharmaceutical compounds in drug research. Assessment of the activity of candidate pharmaceutical compounds generally involves combining the differentiated cells herein with the candidate compound, determining any resulting change, and then correlating the effect of the compound with the observed change. In another instance, the screening is done, for example, either because the compound is designed to have a pharmacological effect on certain cell types, or because a compound designed to have effects elsewhere have unintended side effects. In another instance, two or more drugs are be tested in combination (by combining with the cells either simultaneously or sequentially), to detect possible drug-drug interaction effects. In another instance, compounds are screened initially for potential toxicity. In another instance, cytotoxicity is be determined by the effect on cell viability, survival, morphology, on the expression or release of certain markers, receptors or enzymes, on DNA synthesis or repair. In some embodiments, the mammalian trophoblast stem cell is an hTS cell.

Treatment of Diseases

In one aspect, provided herein is a method of treating or preventing a disease in a mammal in need thereof comprising administering a cell (e.g., an isolated progenitor cell) herein to the mammal in need thereof. In one instance, the cell is immune privileged. In one instance, the cell has low levels of CD33 expression and/or CD133 expression. In one instance, the administering comprises injecting, implanting, or surgical operation. In one instance, the disease is an insulin disorder. In one instance, the disease is diabetes, e.g., Type 1 diabetes or Type 2 diabetes. In one instance, the mammal in need thereof is a rodent, rabbit, cow, sheep, pig, dog, cat, monkey, or ape. In some embodiments, a rodent herein is a mouse, rat, guinea pig, hamster, or squirrel. In some embodiments, an ape herein is chimpanzee, gorilla, or orangutan. In one instance, the mammal in need thereof has one or more symptoms associated with diabetes, e.g., polyuria (frequent urination), polydipsia (increased thirst), polyphagia (increased hunger), weight loss, blurred vision, itchiness, peripheral neuropathy, recurrent vaginal infections, fatigue, slow healing of wounds or sores, and any combination thereof.

In one aspect, provided herein is a method for treating or preventing a disease or a condition comprising administering to a subject in need thereof an effective amount of an isolated mammalian trophoblast stem cell or the differentiated cell prepared using the subject method disclosed herein. In one instance, the disease is an immunodeficient disease, a nervous system disease, a hemopoietic disease, a cancer, or diabetes.

In some embodiments, provided herein is a method for generating insulin-secreting cells to treat diabetic patients, e.g., with isolated mammalian trophoblast stem cells or differentiated cells herein.

In some embodiments, diabetes herein can refer to any metabolic defects in the production and utilization of carbohydrates (e.g., glucose) or any insulin disorder.

In some embodiments, the diabetic patients suffer Type 1 diabetes, Type 2 diabetes, gestational diabetes, or Latent autoimmune diabetes of adults (LADA). In Type 1 diabetes, or insulin-dependent diabetes mellitus (IDDM), patients produce little or no insulin, the hormone which regulates glucose utilization. In Type 2 diabetes, or noninsulin dependent diabetes mellitus (NIDDM), patients often have plasma insulin levels that are the same or even elevated compared to nondiabetic subjects, but have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance. Gestational diabetes (or gestational diabetes mellitus, GDM) can be a condition in which women without previously diagnosed diabetes exhibit high blood glucose levels during pregnancy. Latent autoimmune diabetes of adults (LADA) can be a condition in which type 1 diabetes develops in adults.

In some embodiments, the cells, compositions, and methods herein can be used in the treatment or prevention of diabetes (e.g., diabetes mellitus, diabetic nephropathy, diabetic neuropathy, diabetic angiopathy and microangiopathy), hyperglycemia, obesity, a lipid disorder (e.g., dyslipidemia, hyperlipidemia, hypertriglyceridemia, hypercholesterolemia, low HDL, high LDL, metabolic syndrome (dyslipidaemia), systemic and pulmonary hypertonia, cardiovascular diseases (e.g., cardiac fibroses after myocardial infarction, cardiac hypertrophy and cardiac insufficiency, arteriosclerosis), kidney diseases (e.g., glomerulosclerosis, nephrosclerosis, nephritis, nephropathy, electrolyte excretion disorder), and/or fibroses and inflammatory processes (e.g., liver cirrhosis, pulmonary fibrosis, fibrosing pancreatitis, rheumatism and arthroses, Crohn's disease, chronic bronchitis, radiation fibrosis, sclerodermatitis, cystic fibrosis, scarring, Alzheimer's disease). The cells, compositions, and methods herein can also inhibit the growth of cancer, tumor cells and tumor metastases and are therefore suitable for tumor therapy.

In some embodiments, the cells, compositions, and methods herein can be used for the treatment of the insulin resistance syndrome in a subject having type 2 diabetes mellitus or impaired glucose tolerance or having a family history of diabetes and at least one of the following conditions: dyslipidemia, hypertension, hyperuricemia, a procoagulant state, atherosclerosis, and truncal obesity.

In some embodiments, the cells, compositions, and methods herein can be used in treating or preventing one or more diabetes-related disorders including metabolic syndrome (Syndrome X, or elevated blood glucose, hypertension, obesity, dyslipidemia), hyperglycemia, hyperinsulinemia, impaired glucose tolerance, impaired fasting glucose, insulin resistance, obesity, atherosclerotic disease, cardiovascular disease, cerebrovascular disease, peripheral vessel disease, lupus, polycystic ovary syndrome, carcinogenesis, diabetic neuropathy, diabetic nephropathy, diabetic retinopathy, diabetic macular edema, and hyperplasia.

In some embodiments, the cells, compositions, and methods herein can be used in treating or preventing one or more diseases, disorders and conditions including (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component.

In some embodiments, the cells, compositions, and methods herein can be used, e.g., in combination with antihyperlipidemic agents to treat or prevent cardiovascular disease (CVD). Examples of antihyperlipidemic agents include statin compounds which are cholesterol synthesis inhibitors (e.g., cerivastatin, pravastatin, simvastatin, lovastatin, atorvastatin, fluvastatin, itavastatin or their salts, etc.), squalene synthase inhibitors or fibrate compounds (e.g., bezafibrate, clofibrate, simfibrate, clinofibrate) having a triglyceride lowering action and the like.

In some embodiments, the cells, compositions, and methods herein can be used, e.g., in combination with hypotensive agents to treat or prevent abnormal vascular growth and renal sodium retention caused by high insulin levels and thereby alleviates hypertension. Examples of hypotensive agents include angiotensin converting enzyme inhibitors (e.g., captopril, enalapril, delapril), angiotensin II antagonists (e.g., candesartan cilexetil, losartan, eprosartan, valsantan, termisartan, irbesartan, tasosartan), calcium antagonists (e.g., manidipine, nifedipine, nicardipine, amlodipine, efonidipine), and clonidine.

In some embodiments, the cells, compositions, and methods herein can be used, e.g., in combination with antiobesity agents. Examples of antiobesity agents include antiobesity drugs acting on the central nervous system (e.g., dexfenfluramine, fenfluramine, phentermine, sibutramine, anfepramon, dexamphetamine, mazindol, phenylpropanolamine, clobenzorex), pancreatic lipase inhibitors (e.g. orlistat), beta-3 agonists (e.g., CL-3 16243, SR-5861 1-A, UL-TG-307, SB-226552, AJ-9677, BMS-196085, AZ-40140), anorectic peptides (e.g., leptin, CNTF (Ciliary Neurotrophic Factor) and cholecystokinin agonists (e.g. lintitript, FPL-1 5849).

In some embodiments, provided herein is a method for treating a neurodegenerative disease comprising administering a patient with an effective amount of trophoblast stem cells or their differentiated cell. The mammalian trophoblast stem cell is obtained from trophoblastic villi at fallopian tube of ectopic pregnancy. In one instance, the neurodegenerative disease is Parkinson's disease, Huntington's disease, Alzheimer's disease or chemical-induced neuron damage.

In some embodiments, provided herein is a method to treat a disorder, wherein the method comprises transplanting to a patient in need thereof a pure population of neurons or a complex of specific neural stem cell populations generated by a method herein. In one instance, the patient is diagnosed with a neurological disease. In another instance, the patient is diagnosed with a neuropsychiatric disorder. In another instance, the patient is diagnosed with a neurodegenerative disorder. In another instance, the pure population of neurons comprises dopaminergic neurons.

In one instance, the disease is a neurological disease. In another instance, the disease is a neurodegenerative disease or disorder. Non-limiting examples of neurological disorders include Parkinson's disease, Alzheimer's disease, Huntington's disease, Amyotrophic lateral sclerosis, Friedreich's ataxia, Lewy body disease, spinal muscular atrophy, multiple system atrophy, dementia, schizophrenia, paralysis, multiple sclerosis, spinal cord injuries, brain injuries (e.g., stroke), cranial nerve disorders, peripheral sensory neuropathies, epilepsy, prion disorders, Creutzfeldt-Jakob disease, Alper's disease, cerebellar/spinocerebellar degeneration, Batten disease, corticobasal degeneration, Bell's palsy, Guillain-Barre Syndrome, Pick's disease, and autism.

In some embodiments, the methods described herein can be used to ameliorate or improve a symptom of a neurological disease or disorder. Non-limiting examples of symptoms associated with neurological disease or disorder include tremor, gait disorder, maldispositional gait, dementia, excessive swelling (edema), muscle weakness, atrophy in the lower extremity, movement disorder (chorea), muscle rigidity, a slowing of physical movement (bradykinesia), loss of physical movement (akinesia), forgetfulness, cognitive (intellectual) impairment, loss of recognition (agnosia), impaired functions such as decision-making and planning, hemifacial paralysis, sensory deficits, numbness, tingling, painful paresthesias in the extremities, weakness, cranial nerve palsies, difficulty with speech, eye movements, visual field defects, blindness, hemorrhage, exudates, proximal muscle wasting, dyskinesia, abnormality of tonus in limb muscles, decrease in myotony, incoordination, wrong indication in finger-finger test or finger-nose test, dysmetria, Holmes-Stewart phenomenon, incomplete or complete systemic paralysis, optic neuritis, multiple vision, ocular motor disturbance such as nystagmus, spastic paralysis, painful tonic seizure, Lhermitte syndrome, ataxia, mogilalia, vesicorectal disturbance, orthostatic hypotension, decrease in motor function, bed wetting, poor verbalization, poor sleep patterns, sleep disturbance, appetite disturbance, change in weight, psychomotor agitation or retardation, decreased energy, feelings of worthlessness or excessive or inappropriate guilt, difficulty thinking or concentrating, recurrent thoughts of death or suicidal ideation or attempts, fearfulness, anxiety, irritability, brooding or obsessive rumination, excessive concern with physical health, panic attacks, and phobias.

In some embodiments, the methods herein can be used in treating or preventing cancer, wherein the cancer is carcinoma. Further, the carcinoma is adenocarcinoma or choriocarcinoma. In one instance, the choriocarcinoma is syncytioma malignum.

Production of Insulin, C-Peptide, Betatrophin Protein, and Betatrophin mRNA

In one aspect, provided herein is a method of producing insulin, comprising contacting a mammalian trophoblast stem cell with one or more agents to activate miR-124, thereby producing a progenitor cell that secretes insulin in response to glucose stimulation. In another aspect, provided herein is a method of producing betatrophin protein and/or betatrophin mRNA, comprising contacting a mammalian trophoblast stem cell with one or more agents to activate miR-124, thereby producing a pancreatic progenitor cell that produces betatrophin protein and/or betatrophin mRNA. In one instance, the betatrophin protein or betatrophin mRNA is produced during about 12-28 hours after induction, e.g., about: 12-16, 16-20, 20-24, or 24-28 hours after induction. In one instance, the progenitor cell is a pancreatic progenitor cell. In one instance, the progenitor cell produces C-peptide and/or insulin.

In some embodiments, the mammalian trophoblast stem cell is an hTS cell. In some embodiments, a mammalian trophoblast stem cell herein is from a rodent (e.g., mouse, rat, guinea pig, hamster, or squirrel), rabbit, cow, sheep, pig, dog, cat, monkey, or ape (e.g., chimpanzee, gorilla, or orangutan).

In some embodiments, the miR-124 is activated spatiotemporarily at a definitive endoderm stage, e.g., between about 1 hour to about 8 hours at the definitive endoderm stage. In some embodiments, expression of the miR-124 is elevated. In some embodiments, the one or more agents comprise a protein or steroid hormone, e.g., a growth factor. In some embodiments, the one or more agents comprise a FGF, e.g., FGF1, FGF2 (bFGF), FGF3, FGF4, FGF5, FGF6, FGF7, FGF8, FGF9, or FGF10. In some embodiments, the FGF (e.g., bFGF) is no more than about 200 ng/mL, e.g., from 100-200 ng/mL. In some embodiments, the FGF (e.g., bFGF) is no more than about 100 ng/mL, e.g., from about 0.1 to 1 ng/mL; or from about 1 to about 100 ng/mL. In some embodiments, the concentration of FGF (e.g., bFGF) used herein is from about: 0.1-1, 1-10, 10-20, 20-30, 30-40, 40-50, 50-60, 50-70, 80-90, or 90-100 ng/mL. In some embodiments, the concentration of FGF (e.g., bFGF) used herein is about: 0.1, 0.2, 0.4, 0.6, 0.8, 1, 2, 3, 4, 5, 6, 7, 8, 9, 10, 11, 12, 13, 14, 15, 16, 17, 18, 19, 20, 25, 30, 35, 40, 45, 50, 60, 70, 80, or 90 ng/mL. In some embodiments, the FGF (e.g., bFGF) is about 10 ng/mL. In some embodiments, the one or more agents further comprise an antioxidant or reducing agent (e.g., 2-mercaptoethanol). In some embodiments, the one or more agents further a vitamin (e.g., nicotinamide). In some embodiments, the mammalian trophoblast stem cell is contacted with FGF (e.g., bFGF), 2-mercaptoethanol, and nicotinamide. In some embodiments, the concentration of the antioxidant or reducing agent (e.g., 2-mercaptoethanol) is no more than about 10 mmol/L, e.g., from about 0.1 to about 10 mmol/L. In some embodiments, the concentration of the antioxidant or reducing agent (e.g., 2-mercaptoethanol) is from about: 0.1-1, 1-2, 2-3, 3-4, 4-5, 5-6, 6-7, 7-8, 8-9, or 9-10 mmol/L. In some embodiments, the concentration of the antioxidant or reducing agent (e.g., 2-mercaptoethanol) is about: 0.2, 0.5, 1, 1.5, 2, 3, 4, 5, 6, 7, 8, or 9 mmol/L. In some embodiments, the concentration of the antioxidant or reducing agent (e.g., 2-mercaptoethanol) is about 1 mmol/L. In some embodiments, the concentration of the vitamin (e.g., nicotinamide) is no more than about 100 mmol/L, e.g., from about 1 to about 100 mmol/L. In some embodiments, the concentration of vitamin (e.g., nicotinamide) is from about: 1-10, 10-20, 20-30, 30-40, 40-50, 50-60, 50-70, 80-90, or 90-100 mmol/L. In some embodiments, the concentration of vitamin (e.g., nicotinamide) is about: 2, 4, 6, 8, 10, 12, 14, 16, 18, 20, 30, 40, 50, 60, 70, 80, or 90 mmol/L. In some embodiments, the concentration of vitamin (e.g., nicotinamide) is about 10 mmol/L.

In some embodiments, the mammalian trophoblast stem cell is contacted with one or more agents to regulate activity or expression level of cAMP Responsive Element Binding protein 1 (CREB1), e.g., CREB1 phosphorylation. In some embodiments, the one or more agents comprise a vitamin metabolite, e.g., retinoic acid. In some embodiments, the one or more agents comprise a CREB1-binding protein. In some embodiments, the one or more agents regulate one or more factors selected from the group consisting of mixl1, Cdx2, Oct4, Sox17, Foxa2, and GSK3β.

In some embodiments, the miR-124 herein is miR-124a, miR-124b, miR-124c, miR-124d, or miR-124e, e.g., miR-124a. In some embodiments, the miR-124a is *homo sapiens* miR-124a (hsa-miR-124a), e.g., hsa-miR-124-5p (SEQ ID NO:1: CGUGUUCACAGCGGACCUUGAU) or hsa-miR-124-3p (SEQ ID NO:2: UAAGGCACGCGGUGAAUGCC) or a fragment thereof. In some embodiments, the miR-124 comprises a sequence selected from Table 1, Table 2, and the Drawings, or a fragment thereof.

Regenerative Medicine Research and Therapies

In some embodiments, a mammalian trophoblast stem cell (e.g., an hTS cell) or a differentiated cell thereof herein can be used in growth and/or generation of an organ and/or tissue. In one instance, the mammalian trophoblast stem cell can be used in generating an organ or a tissue or a construct thereof without a scaffold or on a scaffold (e.g., a scaffold of a natural tissue, or a scaffold made of a bio-degradable material). In one instance, a material in the bio-scaffold herein can be a hydrogel, e.g., Collagen Type I, Collagen/Fibrin, Fibrin, Extracel™ Hydrogel, Extracel™ UV, Tyramine substituted hyaluronic acid (TS-NaHy)-Corgel™, Methylcellulose-Hyaluronan (MC-HA), Chitosan, Chitosan/Collagen, Alginate, Alginate/Gelatin, Polyethylene Glycol Diacrylate (PEGDA), or any combination thereof). In one instance, the mammalian trophoblast stem cell herein can be used in generating an organ and/or tissue with a 3D cell bioprinting technique. The 3D cell bioprinting techniques include those disclosed in U.S. Patent Application Publication Nos. 20130017564, 2012/0190078, 2012/0116568, 2011/0250688, 2011/0136162, and 2009/0263849. In one instance, the 3D cell bioprinting technique can maintain high cell viability and/or pluripotency, and/or produce spheroids of uniform size. In one instance, the mammalian trophoblast stem cell herein can be used to generate pancreatic tissues. In one instance, the mammalian trophoblast stem cell herein can be used to generate a functional pancreas. In some embodiments, the mammalian trophoblast stem cell is an hTS cell.

EXAMPLES

The Examples below are non-limiting and merely representative of various aspects and features of the present inventions.

Example 1

Isolation of hTS Cells

This experiment was approved by the Institutional Review Board on Human Subjects Research and Ethics Committees, Kaohsiung Medical University Hospital. The ectopic pregnancy-derived hTS cells were obtained from donors with informed consent. Embryonic chorionic villi were obtained from the fallopian tubes of un-ruptured pre-implantation embryos in women with ectopic pregnancy (gestational age: 5-7 weeks) approved by the Institutional Review Board on Human Subjects Research and Ethics Committees. Tiny villous tissues were well-minced in serum-free α-MEM (Sigma-Aldrich, St. Louis, Mo.) and identified under microscopy followed by trypsinization with 0.025% trypsin/EDTA (Sigma-Aldrich) for 15 min and by adding α-MEM containing 10% FBS to halt the reaction. Adherent cells were obtained and cultured in conditioned α-MEM, 10% FBS, and 1% penicillin-streptomycin at 37° C. in 5% $CO_2$. After two passages, the level of hCG became undetectable measured by a commercial kit (Dako, Carpinteria, Calif.).

Example 2

Figure 5:
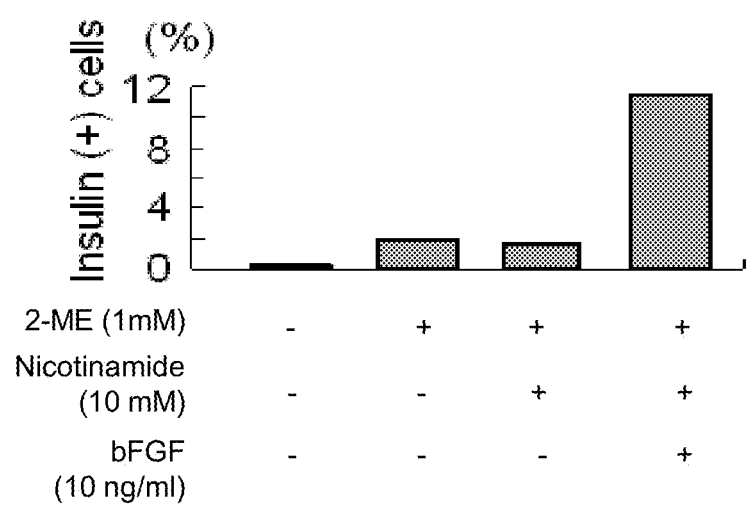
FIG. 5 is a bar chart showing induction efficacy of insulin-expressing cells from hTS cells by various combination of factors, including bFGF, 2-mercaptoethanol (2-ME), and nicotinamide, measured by immnofluoresence assay.
Figure 6A:
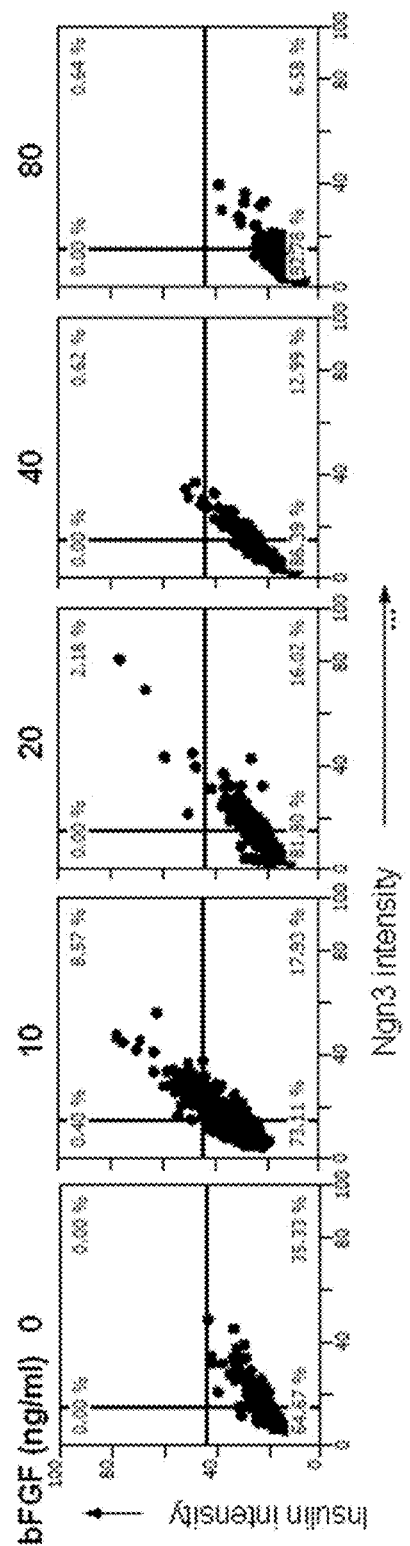
FIG. 6A is a set of TissueQuest analysis images showing dose-effect of bFGF on the production of insulin-expressing cells from hTS cells by co-expression of insulin and Ngn3.
Figure 6B:
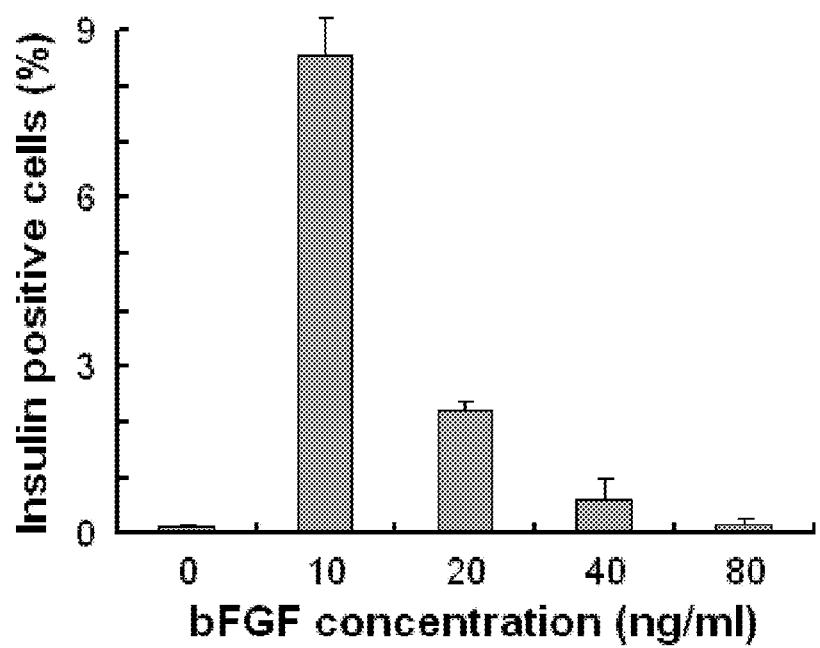
FIG. 6B is a bar chart representing means±SD in triplicate determinations of the data in FIG. 6A.
Figure 7:
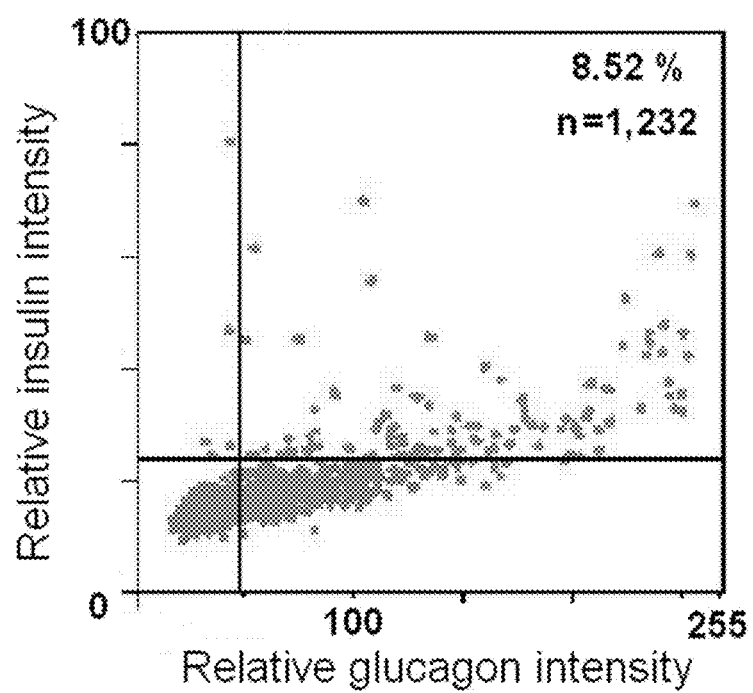
FIG. 7 is a TissueQuest analysis image showing that bFGF (10 ng/ml) achieved similar percentage of insulin-expressing cells by co-expression of insulin and glucagon.

In Vitro Differentiation of hTS Cells into Pancreatic Progenitors by Modulating miR-124a Combination of α-MEM medium containing 5.5 mM glucose, 1 mmol/L β-mercaptonethanol (ME), 10 mmol/L nicotinamide, 20% FBS, and 10 ng/ml bFGF generated 11.2% of maximal immunoreactive insulin-positive compared to the other combinations expressing 2.1% and 1.9% of insulin-positive cells in the population (FIG. 5). bFGF induction used a variety of levels of bFGF (i.e., 10, 20, 40, and 80 ng/ml) and FBS (i.e., serum-free, 1%, 5%, 10%, and 20%). The result showed that the different doses of bFGF yielded 8.6%, 2.2%, and 0.6% of insulin$^+$/Ngn3$^+$ cells, respectively, (FIG. 6). A similar result was achieved by using immunoreactive insulin$^+$/glucagon$^+$ cells (8.5%) as indicators (FIG. 7). Total cell counts for insulin$^+$/glucagon$^+$-expressing cells=1,232 cells. Total cell counts for insulin$^+$ Ngn3$^+$-expressing cells=502 cells (bFGF 10 ng/ml), 712 cells (bFGF 20 ng/ml), 485 cells (bFGF 40 ng/ml), and 571 cells (80 ng/ml). Western blot analysis indicated a positive correlation of FBS and insulin levels during bFGF induction.

Figure 8:
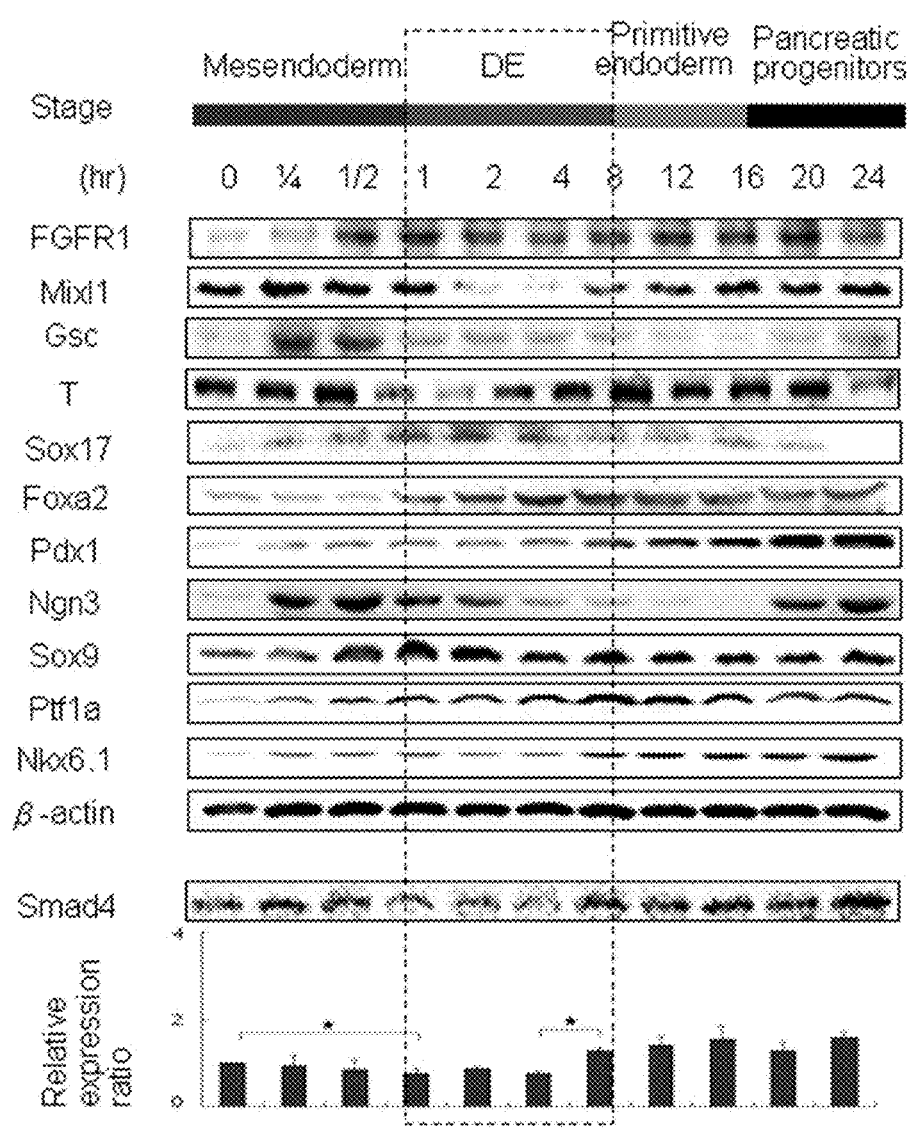
FIG. 8 is a set of images from a representative immuno-blotting assay illustrating the dynamic pattern in level of transcription factors during different cell process over time. The dash box indicates DE state. β-actin was used as control. Data represent as mean±S.D. n=3, *p<0.05.

Upon bFGF induction, a time-course analysis revealed a dynamic profile of transcription factors identifying the cascading stages of pancreatic development (FIG. 1A and FIG. 8). At the beginning of induction, Mix-like 1 homeobox protein (Mixl1), a mesendoderm-related protein, elevated at 15 min after induction. In combination with elevated Brachyury (T) or Goosecoid (Gsc), evidence suggested a stage of migrating nascent mesendoderm. Mixl1 declined at 1 hr while T and Gsc maintained at high levels, implying an early transition from hTS cells to mesendoderm.

Figure 1B:
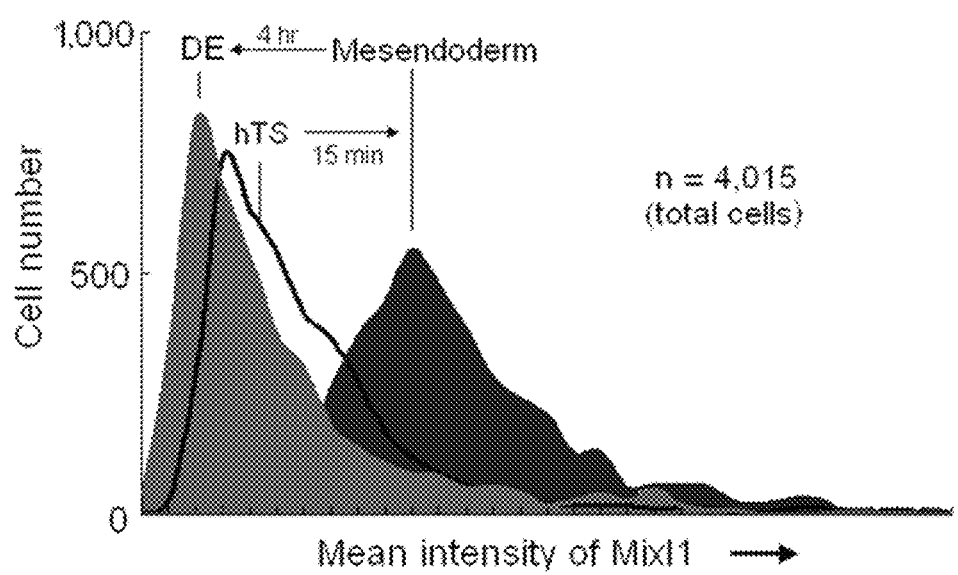
Figure 1C:
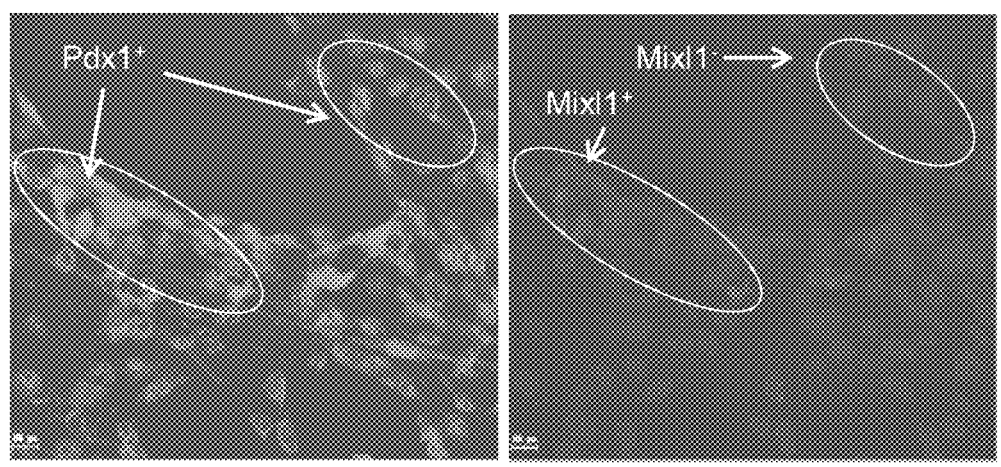

At 1-8 hr, Mixl1 levels dropped to a nadir at 4 hr and returned to original level at 8 hr. This result may cause cells in the endoderm to remain stationary during gastrulation. Changes in Mixl1 intensity at 1-4 hr (FIG. 1B) led to the segregation of mesendoderm into two cell populations: one expressing Pdx1$^+$Mixl1$^+$ for mesoderm and another expressing Pdx1$^+$ Mixl1$^-$ for endoderm (FIG. 1C). Mixl1 mRNA expression is confined to the mesoderm; but is absent from endoderm. Upregulation of SRY homeobox 17 (Sox17), forkhead box protein A2 (Foxa2), and pancreatic and duodenal homeobox 1 (Pdx1) marked the growth of pancreatic buds. Sox17 is required to initiate segregation into a Pdx1$^+$ ventral pancreas and a Sox17$^+$ biliary primordium, but not the liver. Co-expression of Foxa2 and Pdx1 enhanced differentiation into different pancreatic cell subtypes. Overexpression of Pdx1 determines pancreatic specification, but does not induce insulin production even in late stages of differentiation.

At 8-16 hr, SRY homeobox 9 (Sox9) and Pdx1, markers of foregut pancreatic endoderm, were elevated. Sox9 maintains multipotent pancreatic progenitors. While genetic ablation of Pdx1 results in the defects of pancreas, caudal stomach, and duodenum during gut organogenesis. Evidence suggested differentiation to foregut pancreatic endoderm stage.

At 16-24 hr, levels of neurogenin 3 (Ngn3) and Nkx6 homeobox 1 (Nkx6.1) sustained at high levels, but levels of T, Sox17, Foxa2, Pdx1, Sox9, and Ptf1a gradually declined, navigating cell differentiation towards the pancreatic progenitors. Pdx1 regulates Ngn3 for endodermal cells to turn into endocrine cells to form islets via expression of glucagon and somatostatin in the mesenchyme. Elevation of Nkx6.1 increases β-cell proliferation. Together, these results indicated that bFGF induced hTS cell differentiation via DE formation and primitive gut endoderm towards pancreatic progenitors in 24 hr.

Figure 2A:
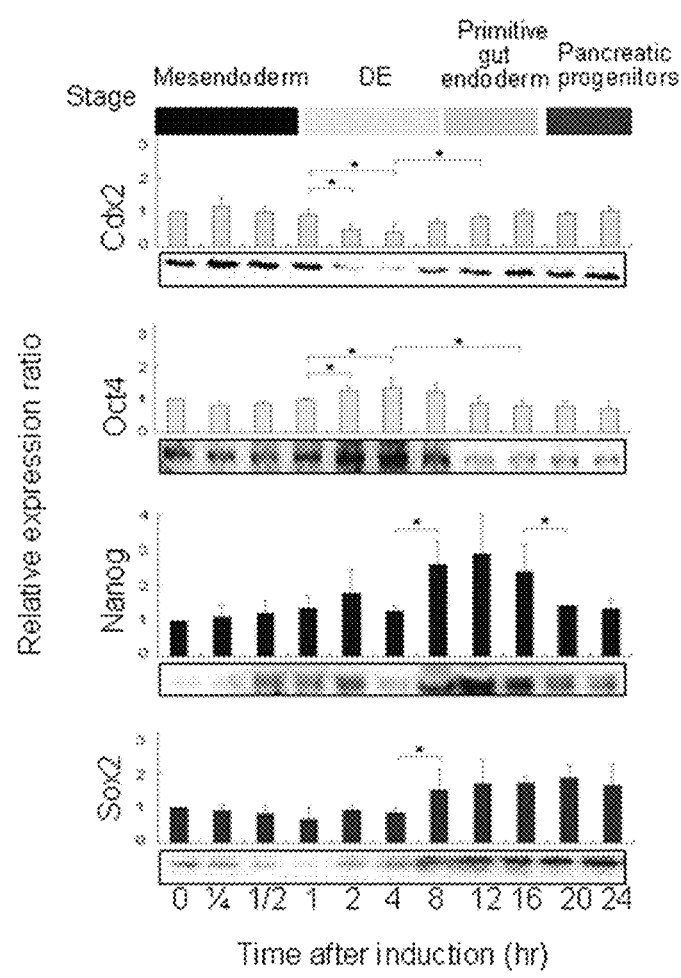
FIGS. 2A-2C are a set of graphs showing the dynamic profile of pluripotency transcription factors in pancreatic differentiation.
Figure 2B:
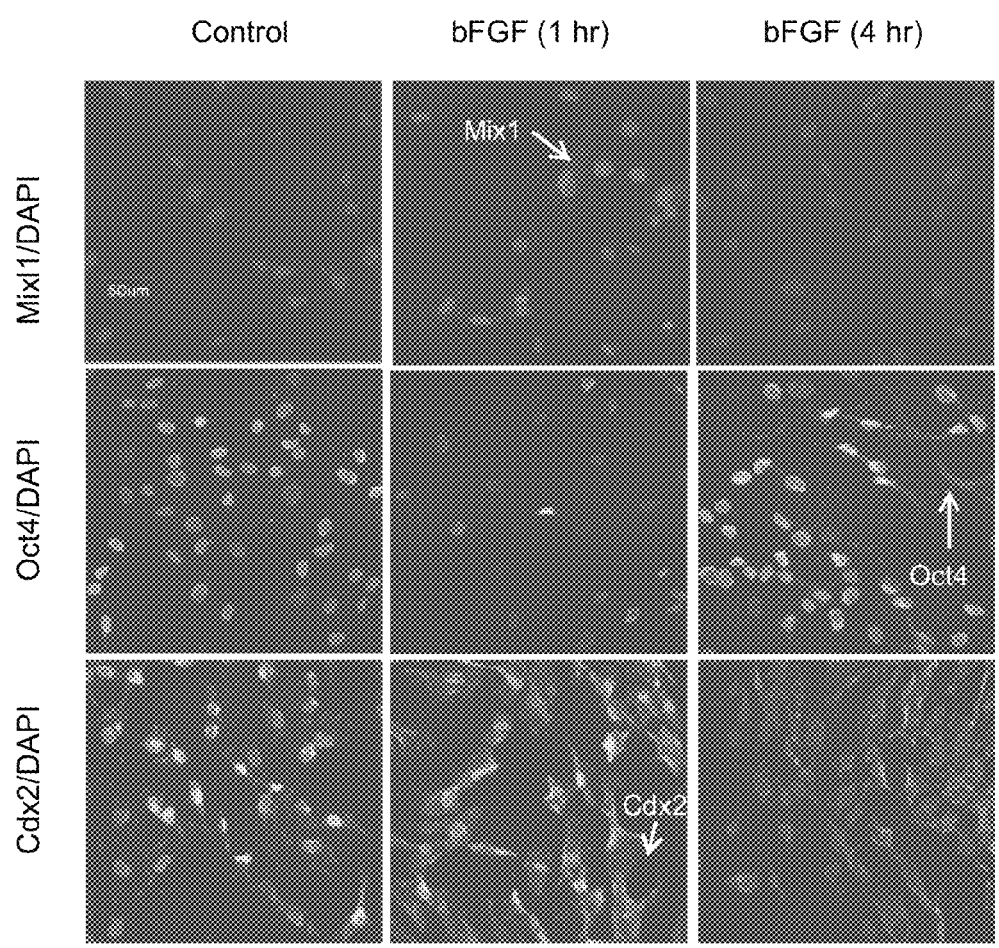
Figure 2C:
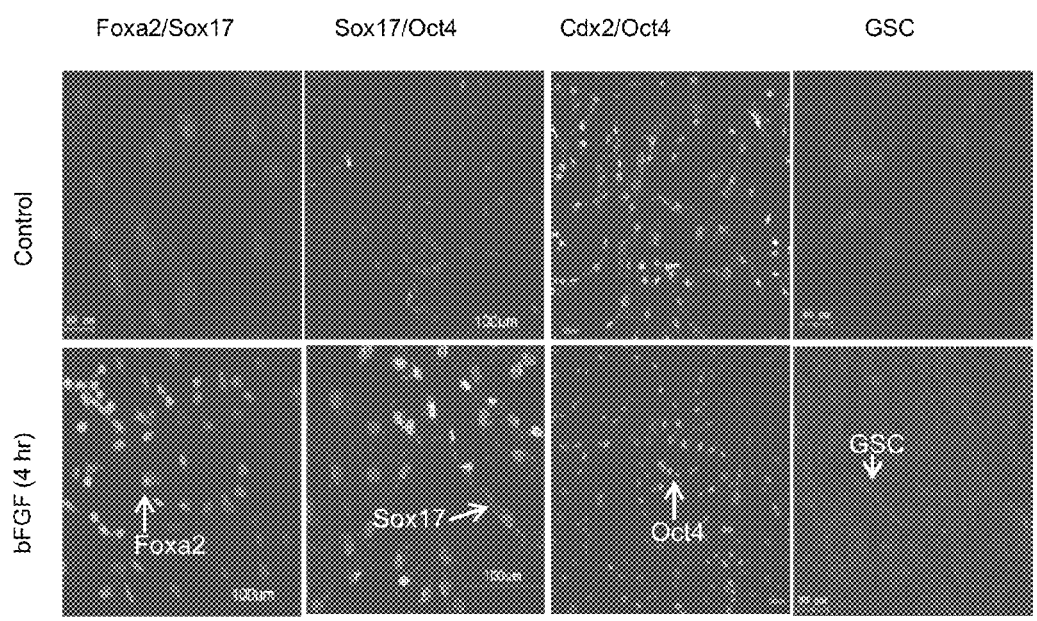
Figure 9:
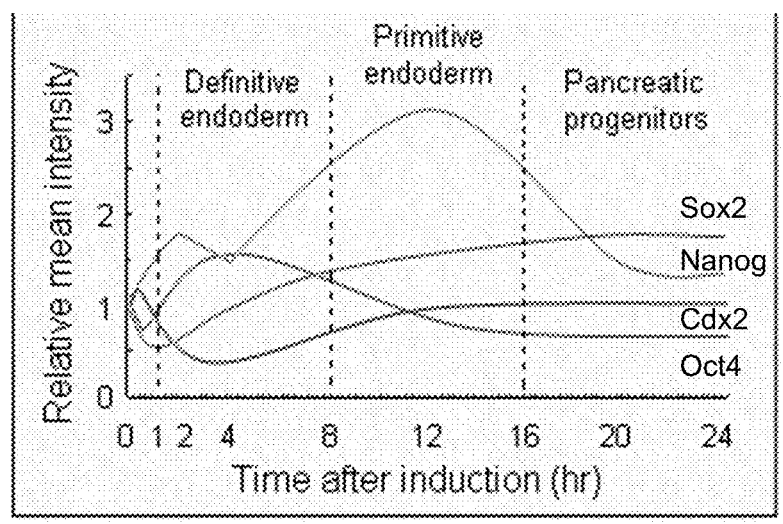
FIG. 9 is a schematic illustrating the negative autoregulatory feedback loop among the pluripotency transcription factors (Nanog, Sox2, Cdx2, and Oct4) in the bFGF-induced cell processes.
Figure 10:
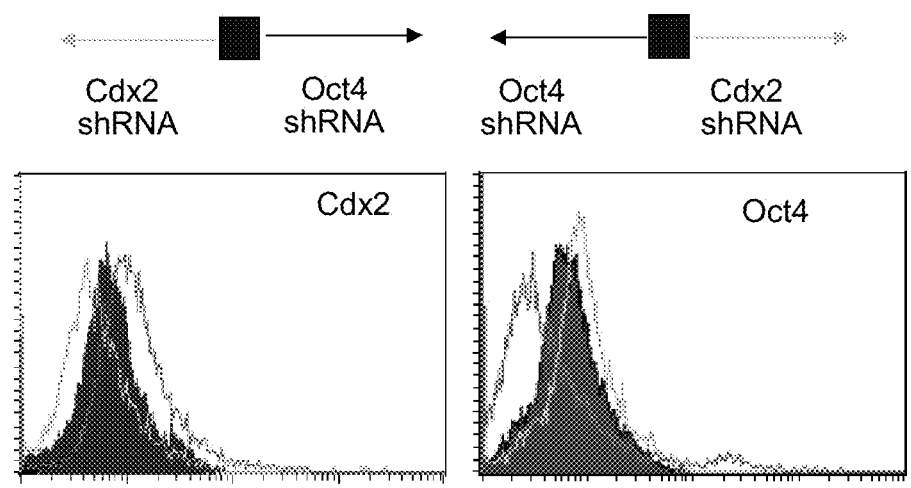
FIG. 10 is a set of flow cytometry images showing a reciprocal inhibitory relationship between Cdx2 (left) and Oct4 (right). Non-specific shRNA was used as control.
Figure 11:
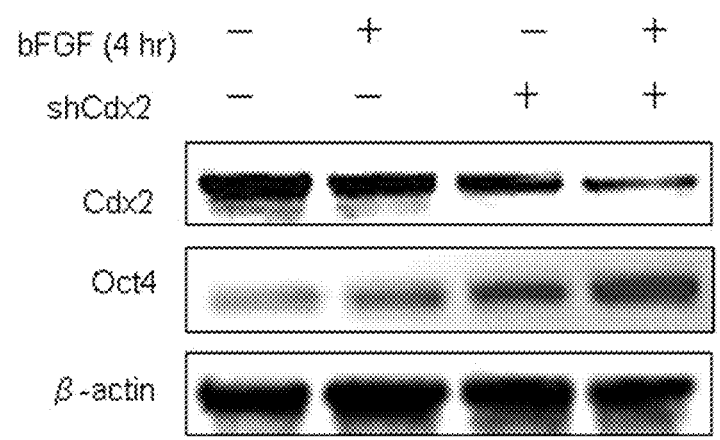
FIG. 11 is a set of western blot images showing that knockdown of Cdx2 up-regulated Oct4. Cells transfected with non-specific shRNA were used as control. β-actin was used as loading control.
Figure 12:
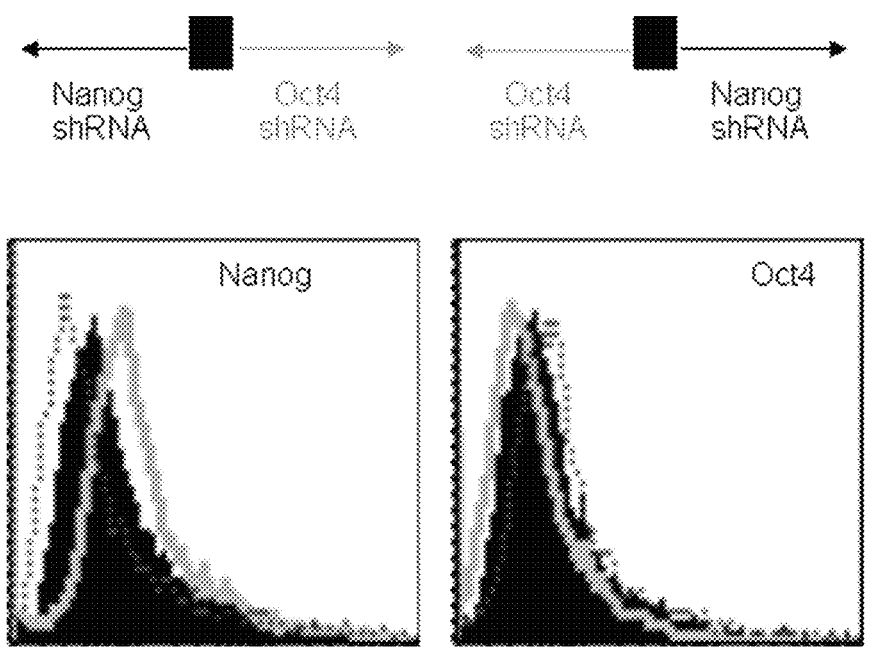
FIG. 12 is a set of flow cytometry images showing that knockdown of Oct4 up-regulated Nanog (left) and vice versa (right).
Figure 13:
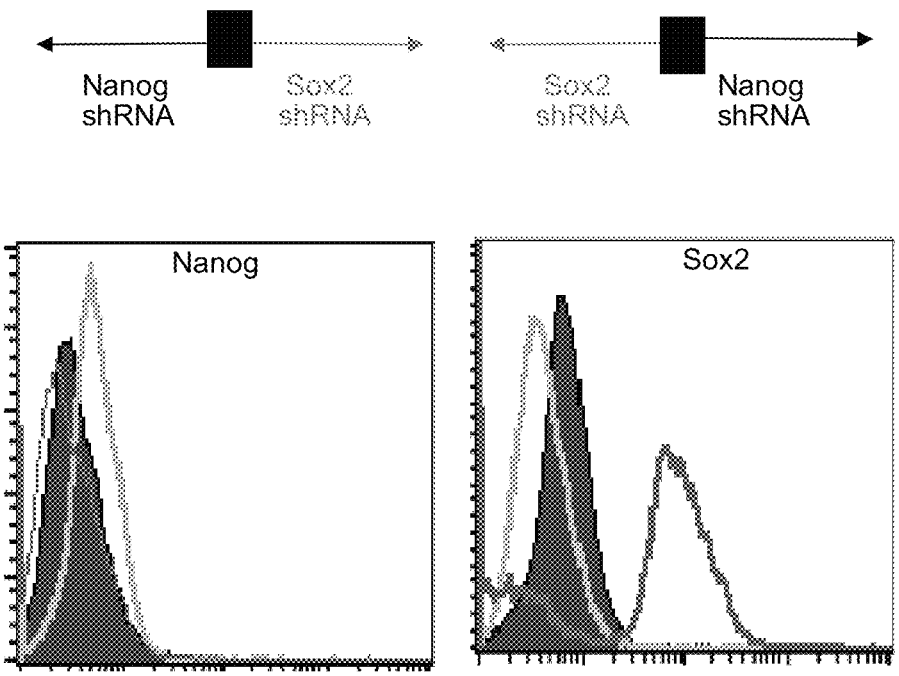
FIG. 13 is a set of flow cytometry images showing that knockdown of Nanog up-regulated Sox2 (right) and vice versa (left).
Figure 14:
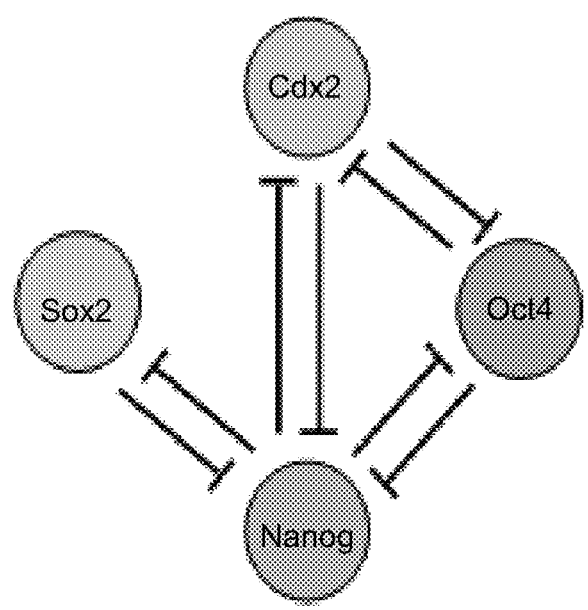
FIG. 14 is a scheme illustrating an autoregulatory loop of reciprocal repression among pluripotency transcription factors.
Figure 15:
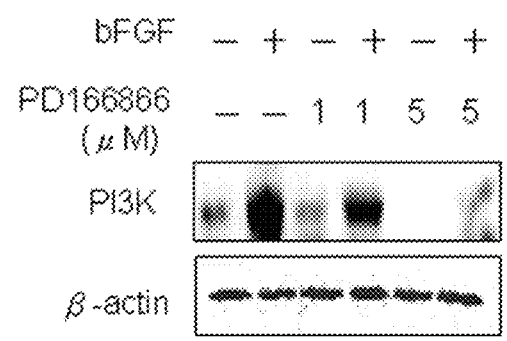
FIG. 15 is a set of western blotting images showing that FGFR inhibitor (PD 166866) blocked the bFGF-induced PI3K. β-actin was used as loading control.
Figure 16:
FIG. 16 is IP assay data showing that Akt interacted directly to CREB1.
Figure 17:
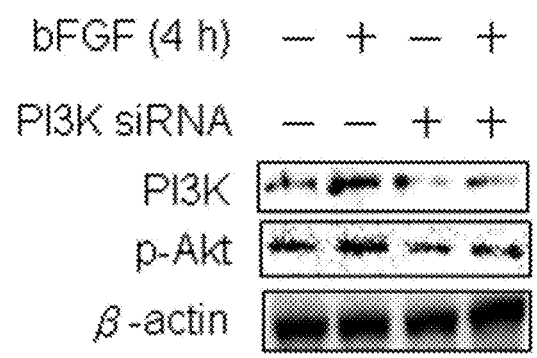
FIG. 17 is a set of western blotting images showing that PI3K siRNA inhibited expression of PI3K and p-Akt. Cells transfected with non-specific shRNA were used as control. β-actin was used as loading control.
Figure 18:
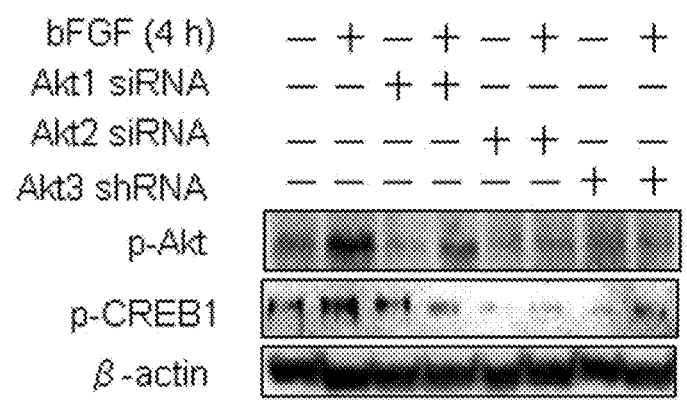
FIG. 18 is a set of western blotting images showing siRNAs against Akt subunits inhibited the bFGF-induced expressions of p-Akt and p-CREB1. Cells transfected with non-specific shRNA were used as control. β-actin was used as loading control.

FIG. 2A and FIG. 9 show a dynamic profile of Cdx2, Oct4, Nanog, and Sox2 in a time-course analysis. Dominant pluripotency transcription factors at each stage of differentiation include Cdx2 for mesendoderm, Oct4 and Nanog for DE, Cdx2 and Nanog for primitive gut endoderm, and Sox2 for pancreatic progenitors. Immunocytochemical studies indicated a reciprocal negative autoregulatory feedback loop (FIGS. 10-13) during cell transition (FIG. 2B, FIG. 14) that is compatible with findings in hES cells. FIG. 2C shows immunocytochemical overexpression of Oct4 along with Sox17, Foxa2, Pdx1, and Gsc at 4 hr, confirming Oct4 at DE stage. These results suggest a unique interplay of pluripotency transcription factor and phenotypic change that determined cell fate during pancreatic differentiation.

Figure 3A:
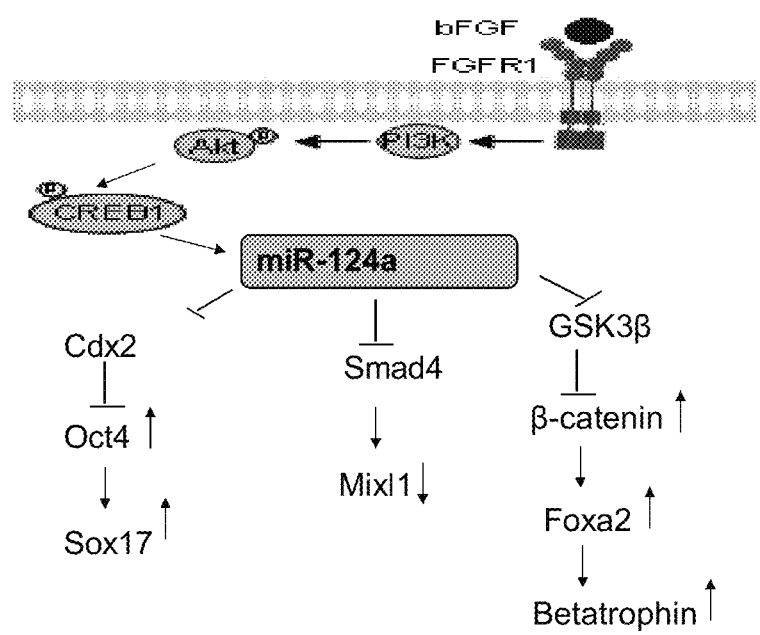
Figure 3B:
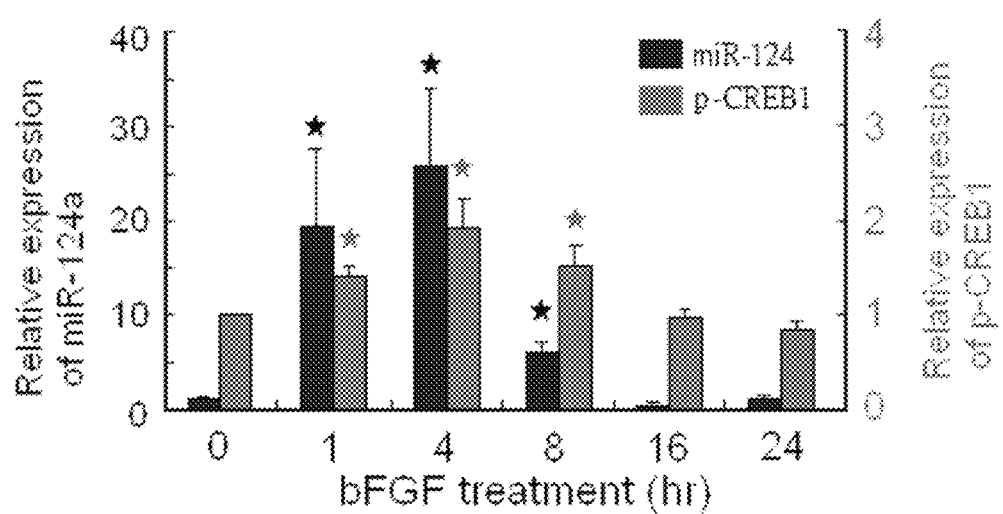
Figure 3C:
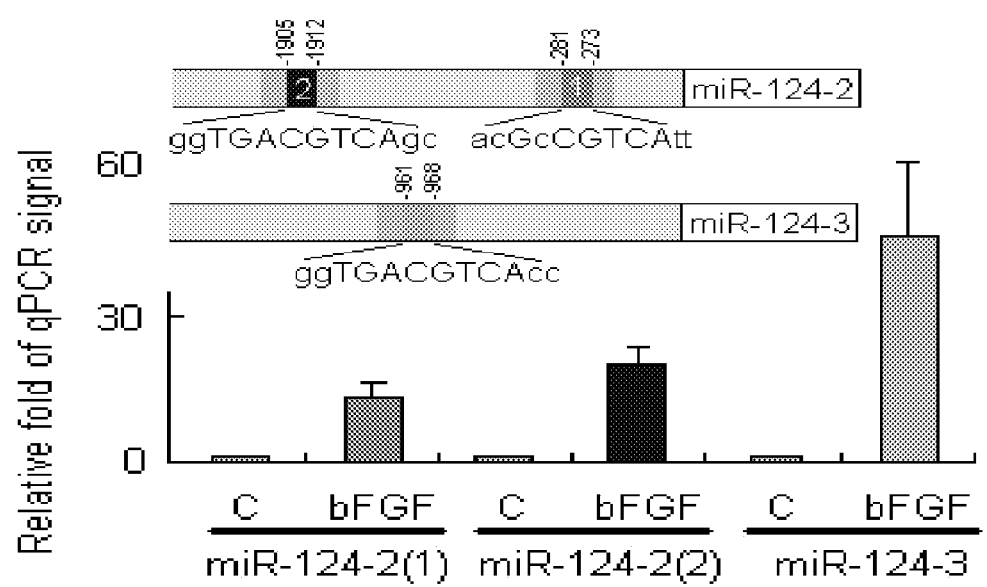
Figure 3D:
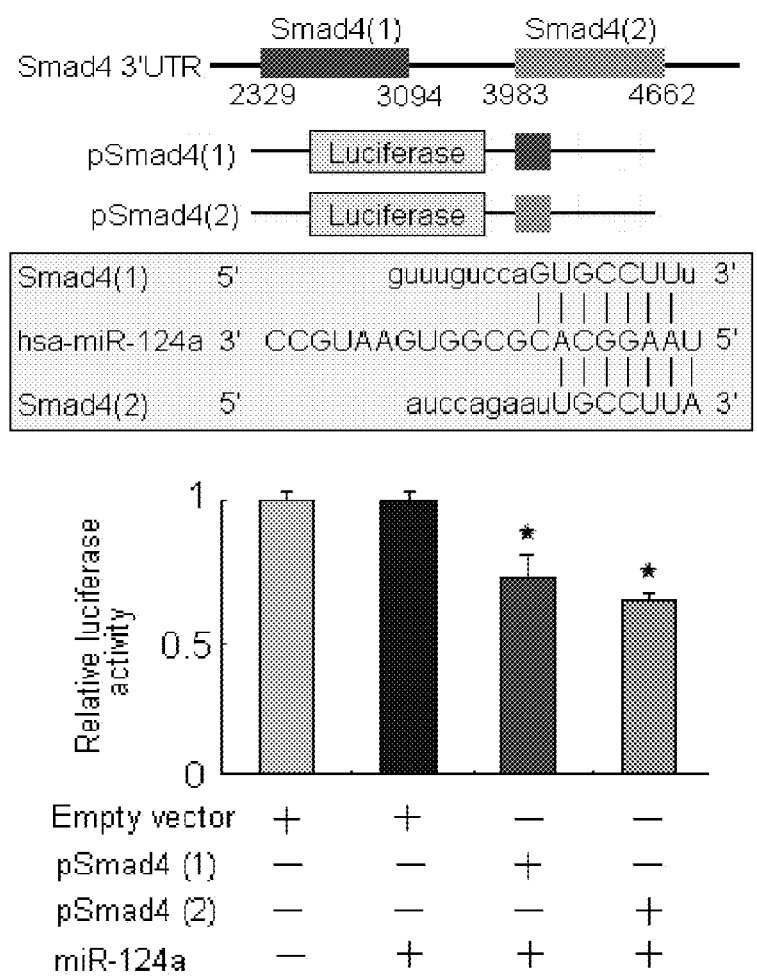
Figure 3E:
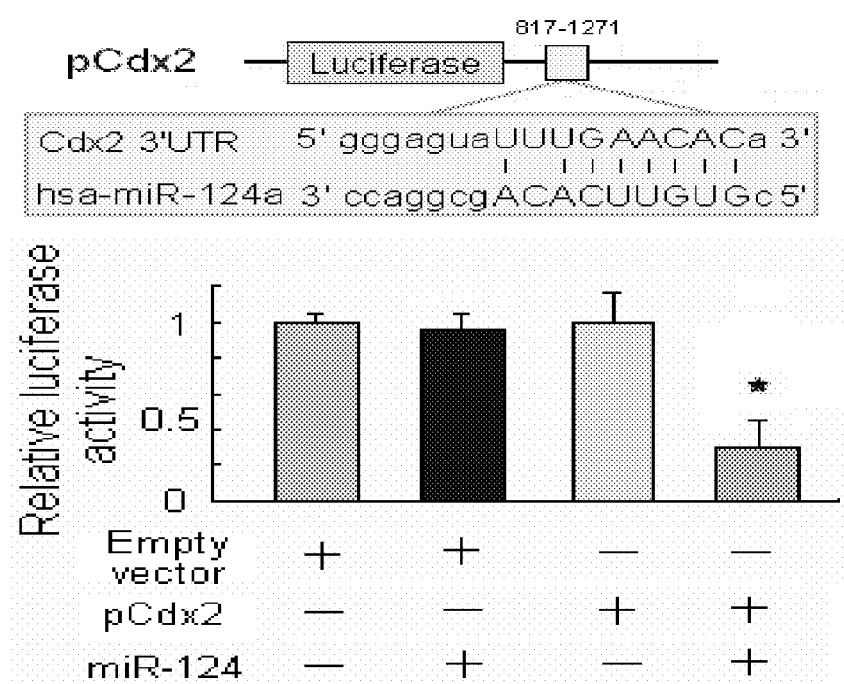
Figure 19:
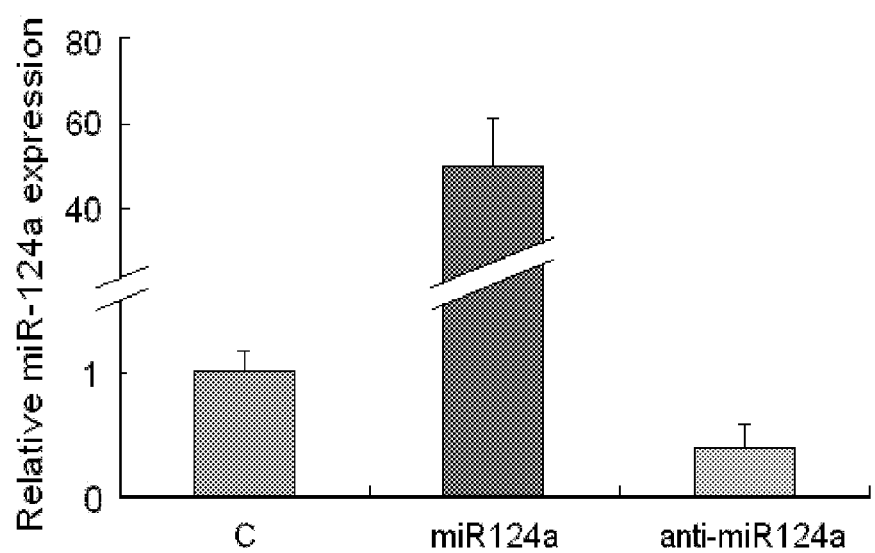
FIG. 19 is a bar chart showing relative miR-124a expression when plasmids containing miR-124a or anti-miR-124a cDNA were transfected into hTS cells for experimental setup in the assay. Data represent mean±SD, n=5.
Figure 20:
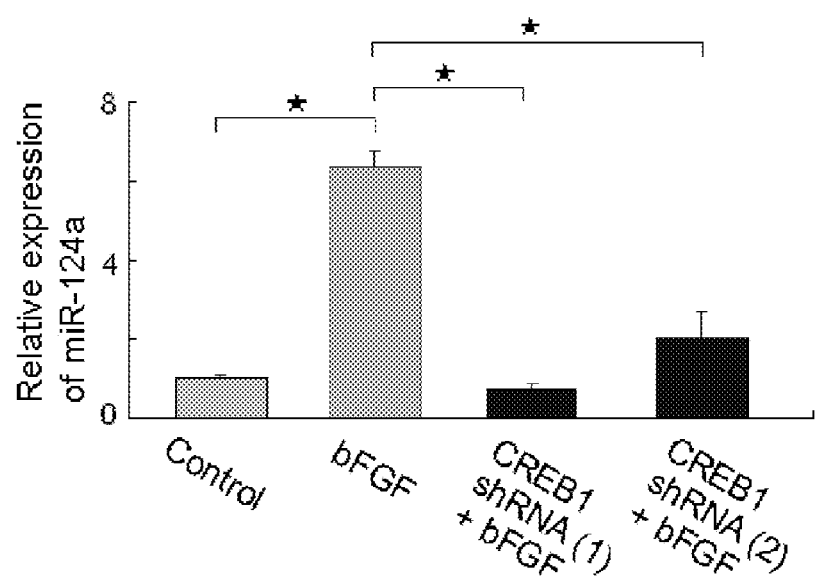
FIG. 20 is a bar chart showing relative miR-124a expressions of hTS cells induced with bFGF alone and bFGF-induced hTS cells transfected with CREB1 shRNAs. Non-specific shRNA was used as control. Data represent mean±SD, n=3, *p<0.05.

FIG. 3A illustrates the molecular pathways to DE specification via miR-124a. Immunoblotting assay revealed that bFGF activated the PI3K/Akt pathway and its downstream effecter cAMP response element-binding protein 1 (CREB1) via FGFR1 (FIGS. 15-18). A correlation between miR-124a and p-CREB1 expression was observed over-time (FIG. 3B), suggesting CREB1 promoted production of miR-124a (FIG. 3C, FIGS. 19-20). These results suggested that bFGF induced biogenesis of miR-124a via phosphorylation of CREB1.

miRNAs are post-transcriptional regulators of genes that target mRNA sequences within the 3' untranslated region (3'UTR) to inhibit translation and/or to cause RNA degradation. Through sequence analysis and luciferase reporter assays, miR-124a inhibited Smad4 (FIG. 3D), Cdx2 (FIG.

Figure 3F:
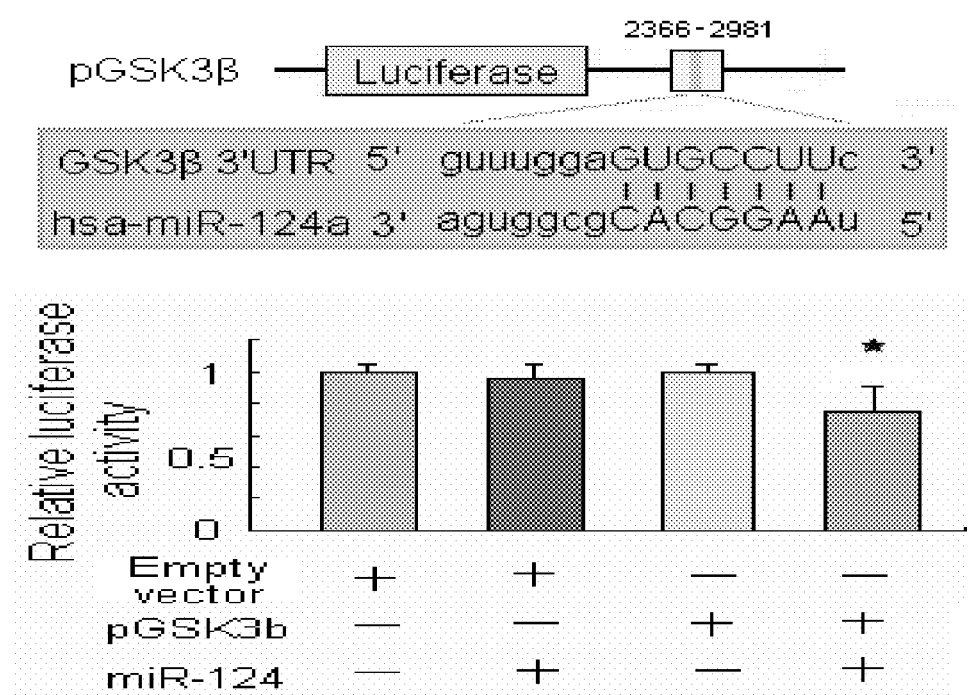
Figure 3G:
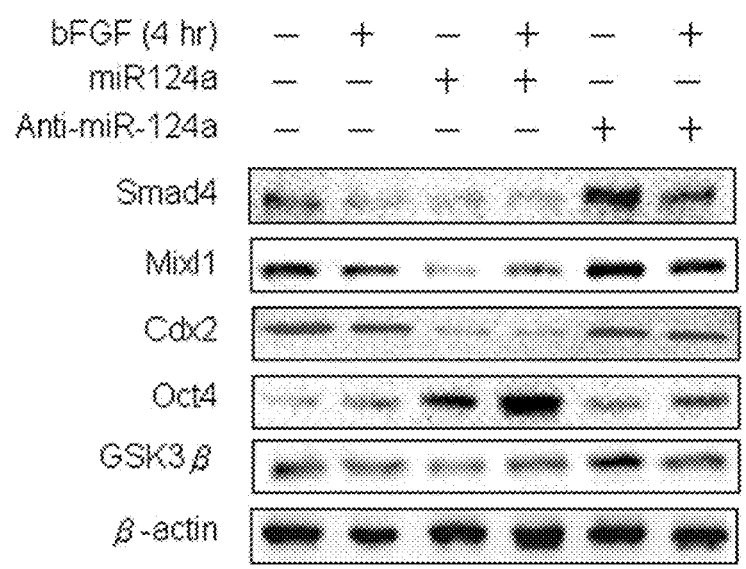
Figure 3H:
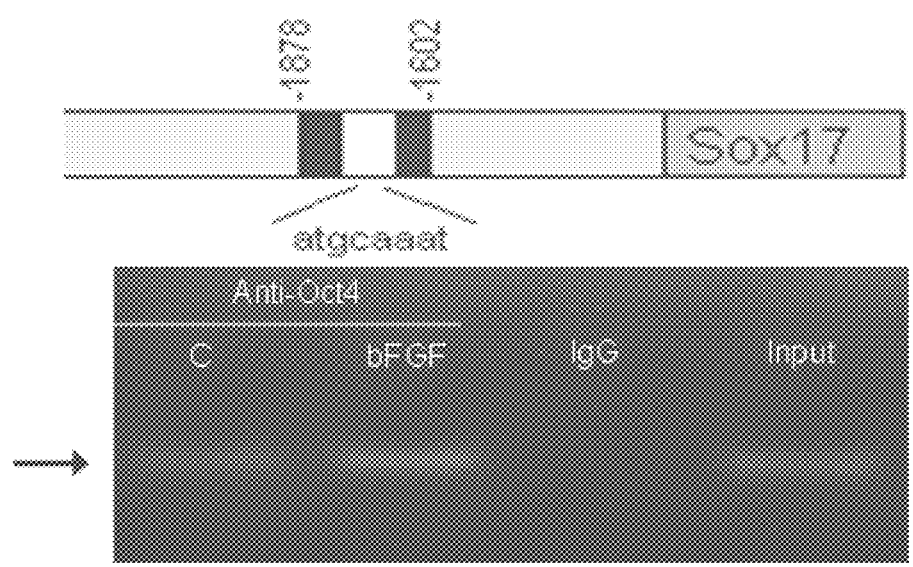
Figure 3I:
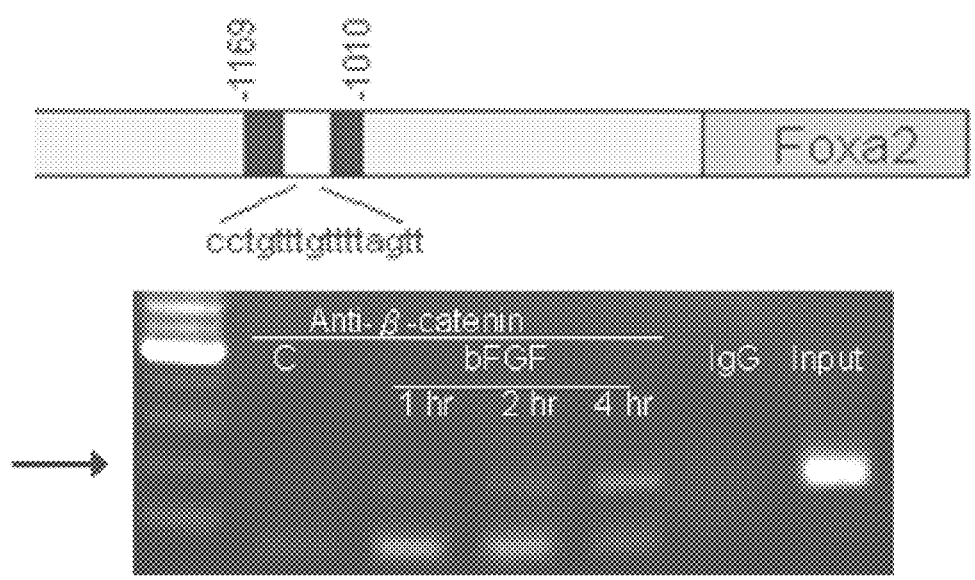
Figure 21:
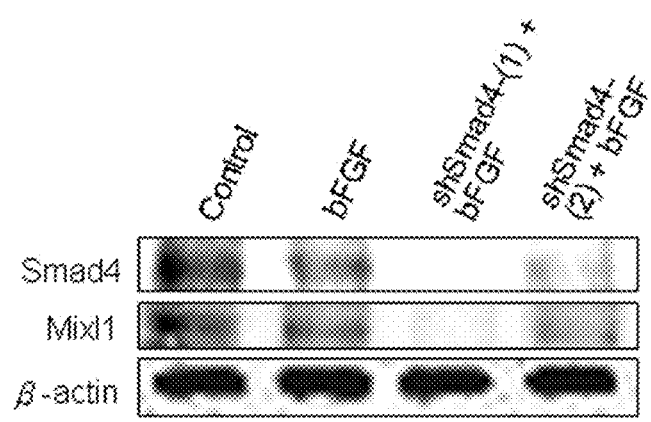
FIG. 21 is a set of western blotting images showing that bFGF-induced Mixl1 suppression was inhibited by using Smad4 shRNAs. Cells transfected with non-specific shRNA were used as control. β-actin was used as loading control.
Figure 22:
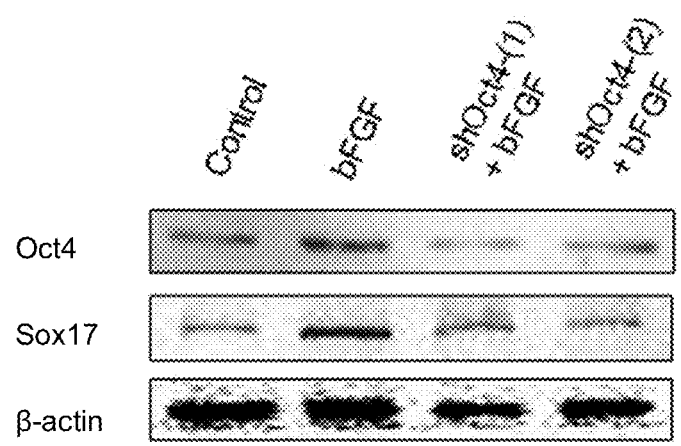
FIG. 22 is a set of western blotting images showing that bFGF-induced Oct4 and Sox17 expressions were inhibited by using Oct4 shRNAs. Cells transfected with non-specific shRNA were used as control. β-actin was used as loading control.
Figure 23:
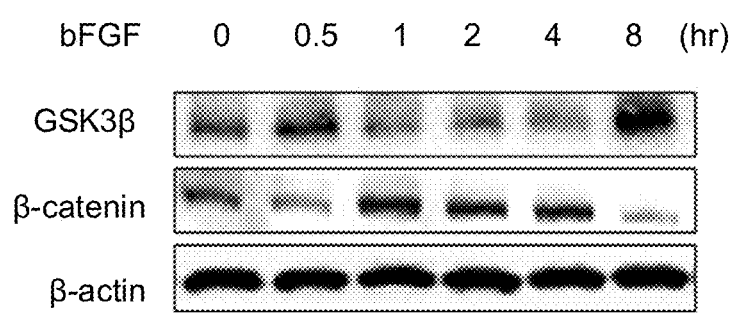
FIG. 23 is a set of western blotting images showing an inhibitory GSK3β between 1-4 hr after bFGF induction, resulted in an accumulation of β-catenin at the same period. β-actin was used as loading control.

3E), and GSK3β (FIG. 3F). Evidences confirmed these results by pre-transfection of miR-124a and anti-miR-124a (FIG. 3G). Consistent with reports, knockdown of Smad4 suppressed Mixl1 (FIG. 21), explaining the downregulation of Mixl1 during DE transition. Inhibition of Cdx2 then promoted Oct4 activation. Chromatin immunoprecipitation (ChIP) assay revealed that Oct4 targeted the promoter of Sox 17 (FIG. 3H) for Sox17 expression (FIG. 22). In turn, inhibition of GSK3β at 1-4 hr resulted in the stabilization and accumulation of β-catenin in the cytoplasm (FIG. 23). Nuclear translocation of β-catenin targeted the gene Foxa2 (FIG. 3I) for Foxa2 expression (FIG. 8). miR-124a was previously reported to regulate Foxa2 in β-cell lines. To this end, bFGF induced multifaceted functions of miR-124a via upregulation of Oct4, Sox17, and Foxa2, but downregulation of Smad4 and Mixl1 at the DE stage.

Figure 3J:
Figure 3K:
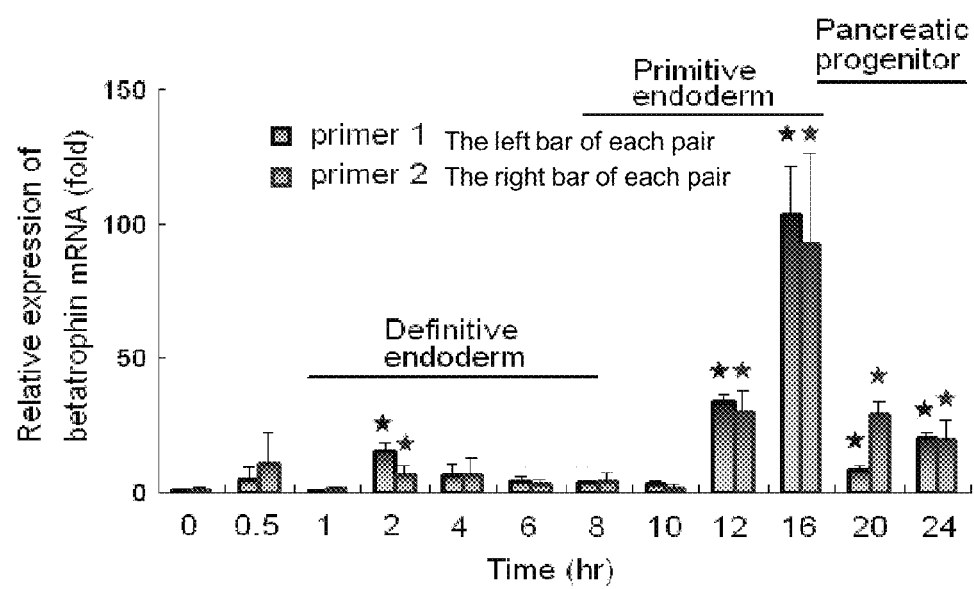
Figure 3L:
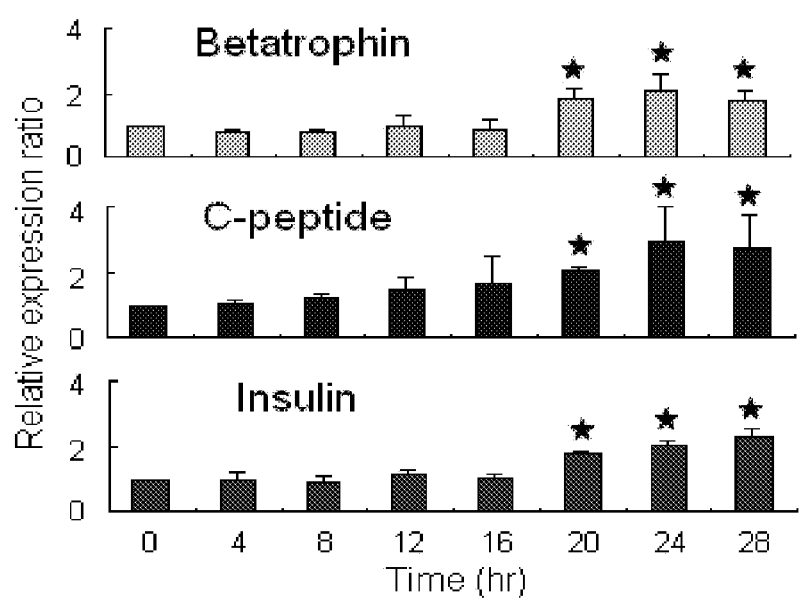
Figure 3M:
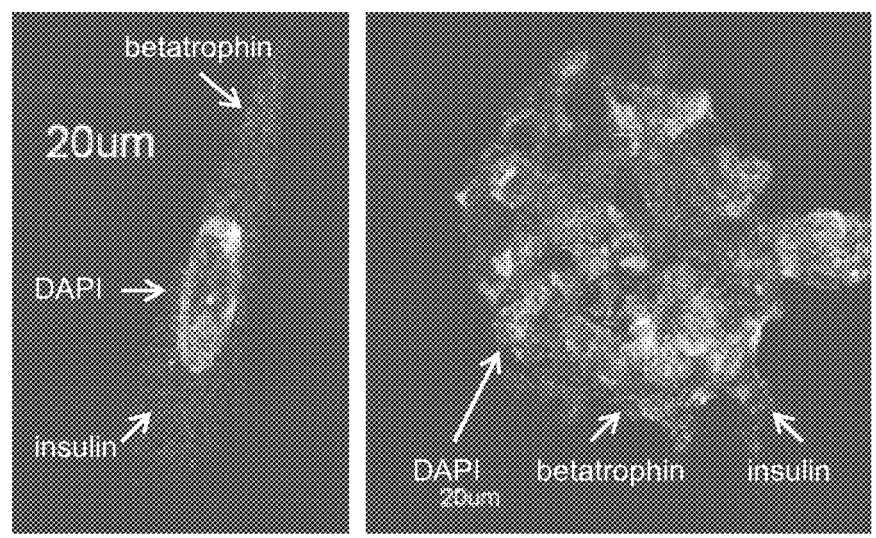
Figure 24:
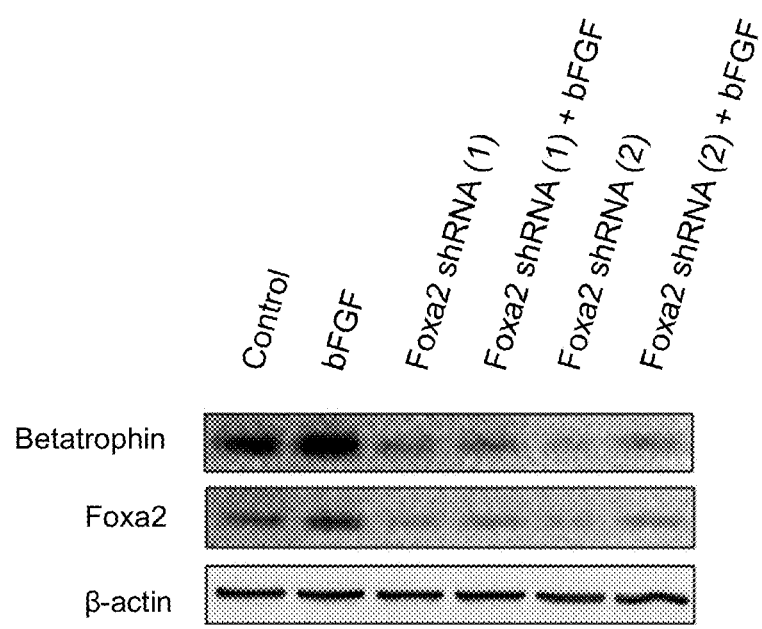
FIG. 24 is a set of a western blotting images showing that bFGF-induced Foxa2 expression was attenuated at the presence of shRNAs against Foxa2. Cells transfected with non-specific shRNA were used as control. β-actin was used as loading control.
Figure 25:
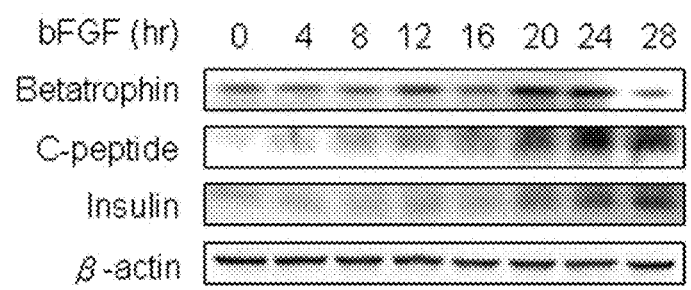
FIG. 25 is a set of western blotting images showing a dynamic correlation in expression among betatrophin, C-peptide, and insulin before 24 hr after bFGF induction. At 28 hr, a trend declined in betatrophin level while levels of C-peptide and insulin sustained at higher ones. β-actin was used as loading control.
Figure 26:
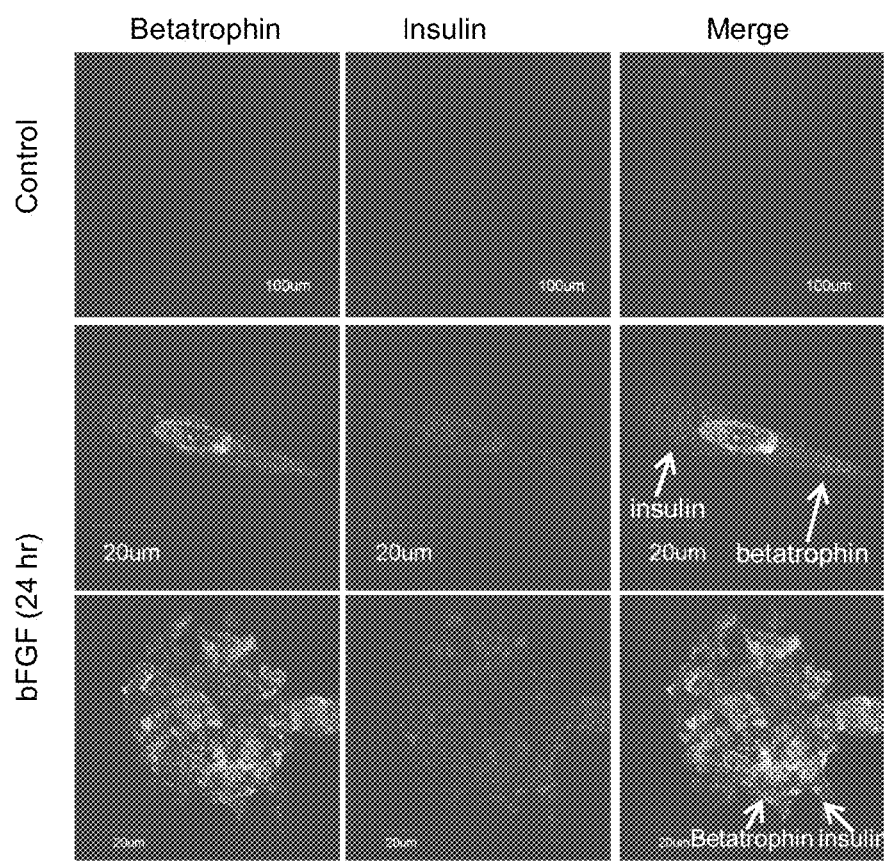
FIG. 26 is a set of immunocytochemistry images showing coexpression of betatrophin (light dots) and insulin (dark dots) in the bFGF-induced pancreatic progenitors.

Betatrophin, a protein hormone, is primarily expressed in the liver and functionally induces high pancreatic β-cell proliferation rates. Foxa2 targeted the promoter of gene C19orf80 to produce betatrophin at 12 hr (FIG. 3J, FIG. 24). qPCR analysis revealed a spatiotemporal elevation of betatrophin mRNA starting at 12 hr, peaking about 100% at 16 hr, and declining thereafter towards 24 hr (FIG. 3K). A parallel expression was observed among betatrophin, C-peptide, and insulin during 20-28 hr, covering both primitive gut endoderm and pancreatic progenitor stages (FIG. 3L, FIG. 25). Immunocytochemically, hTS cell-derived pancreatic progenitors co-expressed betatrophin and insulin (FIG. 3M, FIG. 26). Without being bound by or to any particular theory, it is believed that betatrophin might also modulate pancreatic progenitor proliferation during pancreatic development.

Example 3

Figure 4A:
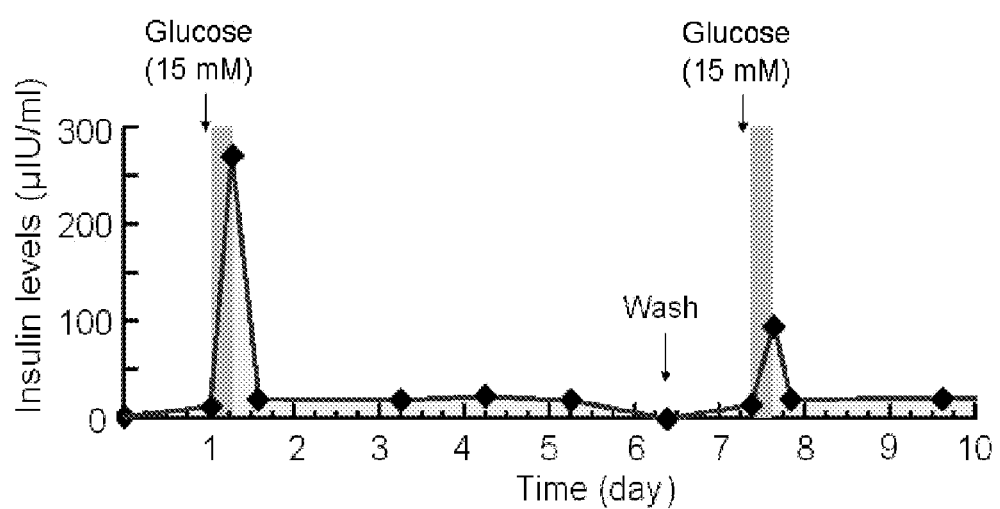
FIGS. 4A-4E are a set of graphs showing characteristics of the hTS cell-derived pancreatic progenitors.
Figure 4B:
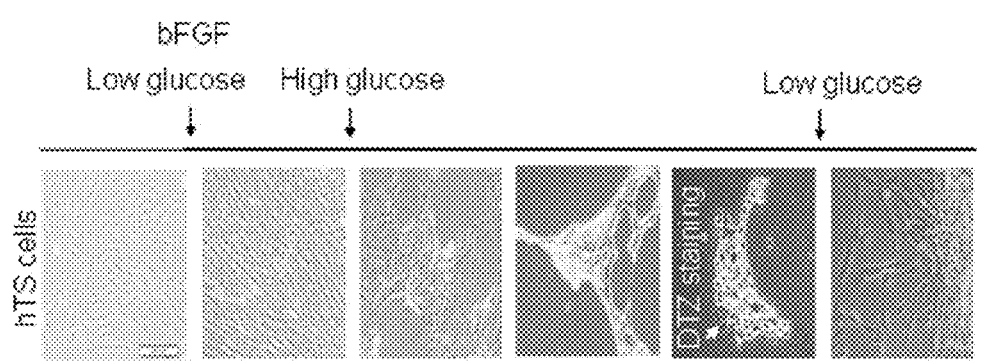

The hTS Cell-Derived Pancreatic Progenitors Secreted Insulin in Response to Glucose Stimulation The pancreatic progenitors monitored the glucose levels by secreting immunoreactive insulin into media (FIG. 4A). Interestingly, evidences show a rapid aggregation of cells to form 3D grape-like cell mass with positive dithizone (DTZ) staining, a specific staining for β-cells. Upon withdrawal of high glucose, the cell mass reverted back to fibroblast-like features (FIG. 4B). The cellular processes were recorded by a computer-microscopy-video system.

Figure 4C:
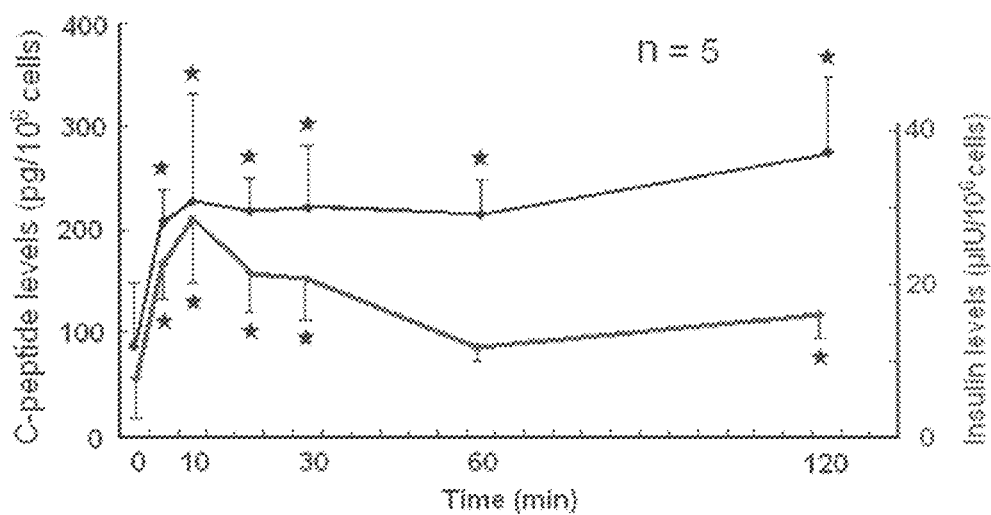
Figure 4D:
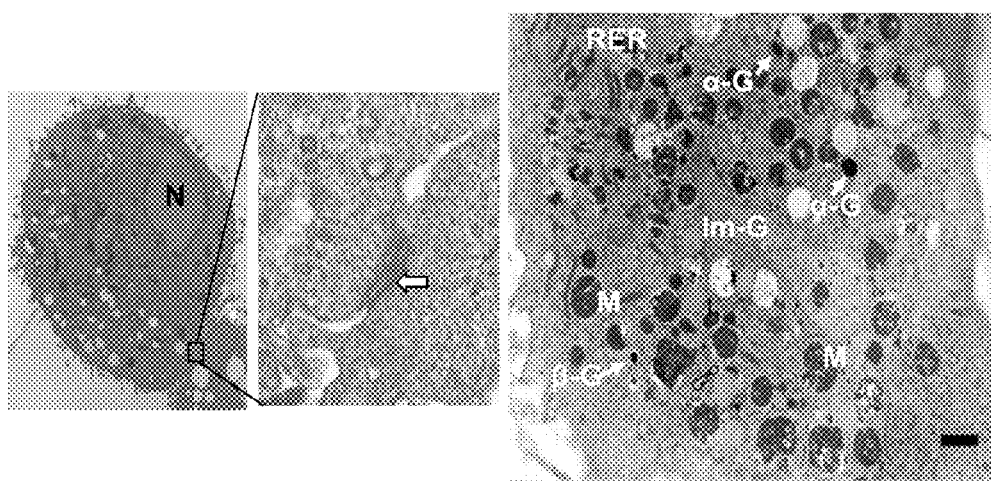

Radioimmunoassay measured a significant elevation of both immunoreactive C-peptide and insulin levels in response to the high glucose (25 mM) stimulation (FIG. 4C). Ultrastructural study of the DTZ-positive cell mass revealed the presence of round cells with a large cytoplasm to nuclear ratio, intercellular bridge (desmosome junction), abundant mitochondria, immature granules, and secretory granules mimicking those of α- and β-cells of the pancreas (FIG. 4D).

Figure 4E:
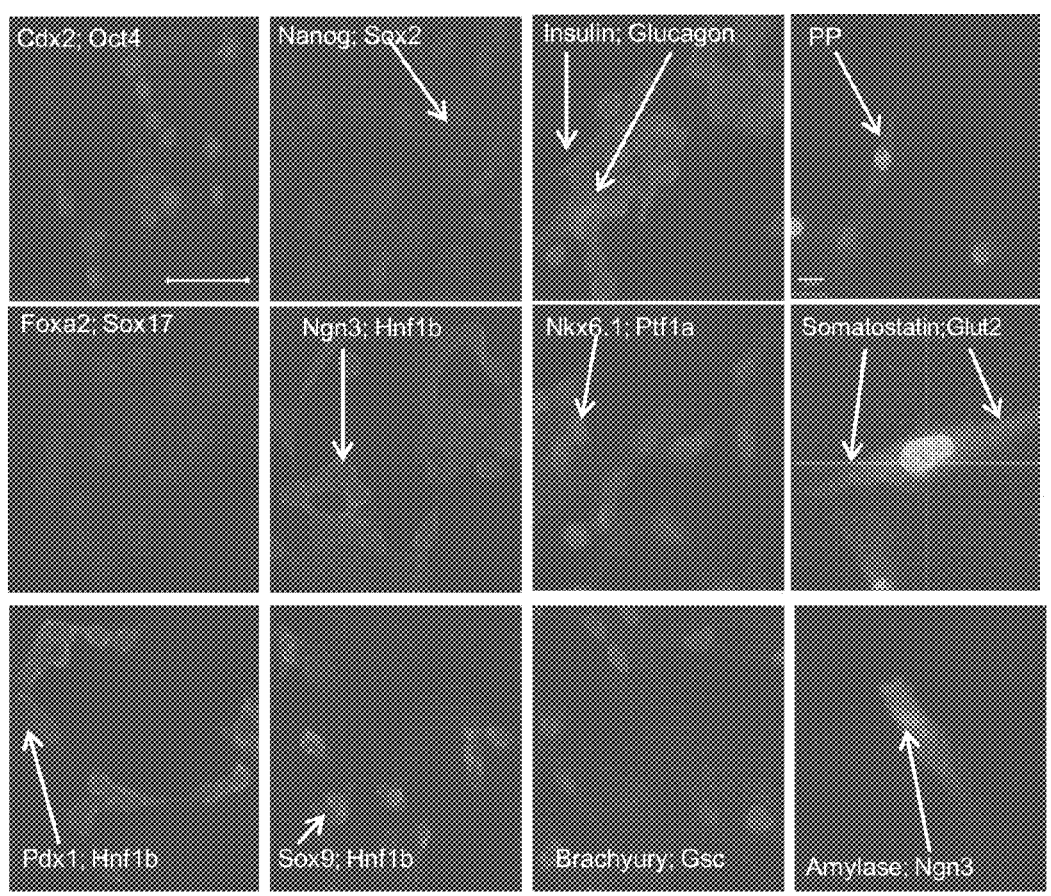

The hTS cell-derived pancreatic progenitor cells expressed a variety of markers, including Sox2, Nkx6.1, Ptf1a, Ngn3, Pdx1, Sox9, betatrophin as well as endocrine components such as insulin (β-cells), somatostatin (δ-cells), glucagon (α-cells), pancreatic polypeptide (PP-cells), glucose metabolic transporter Glut2, and catalytic enzyme amylase immunocytochemically (FIG. 4E). All the evidence suggested the presence of pancreatic progenitors and they responded positively to glucose stimulation test by expressing C-peptide and insulin.

Materials and Methods for Experiments Described in Examples 2-3

Cell Culture and Differentiation

Undifferentiated hTS cells were maintained in α-MEM (Gibco) supplemented with 10% (v/v) fetal bovine serum (SAFC Biosciences). Cultures were manually passaged at a 1:3-1:6 split ratio every 2-3 days. Differentiation of pancreatic progenitors was carried out by a conditioned α-MEM media containing 20% FBS, 1 mM 2-mercaptoethanol, 10 mM nicotinamide and 10 ng/ml bFGF for 24 hr in 37° C., 5% $CO_2$ incubator. The regimen of differentiation was determined by empirical experience as shown in FIGS. 5-7. Stage-specific differentiation of lineages was referred to a variety of cell markers as previously described (M. Borowiak, Rev. Diabet. Stud. 7, 93-104 (2010); K. A. D'Amour, et al., Nat. Biotech. 23, 1534-1541 (2005); E. Kroon, et al., Nat. Biotech. 26, 443-452 (2008)). Cells were harvested at time as indicated for different assays.

Reagents

DTZ (Merck KGaA, Darmstadt, Germany), bFGF (Sigma), fluorescein isothiocyanate (FITC), Texas Red 594 (Invitrogen), DyLight 488-, DyLight 594- (Thermo Scientific), phycoerythrin (PE)-conjugated secondary antibody (Jackson ImmunoResearch, Baltimore, Md.). shRNAs were purchased from National RNAi Core Facility, Academia Sinica, Taiwan.

Western Blot

Method of this assay was described previously (T. T. Y. Lee, et al., PLoS ONE 7, e52491 (2012)). Briefly, cells were harvested into RIPA lysis solution (Millipore, Billerica, Mass.) supplemented with protease and phosphatase inhibitors (Roche). After electrophoresis of 30-µg lysates on polyacrylamide gels, electroblotting onto PDVF membranes (Millipore) was performed. After blocked in 5% nonfat dry milk in PBS for 1 hr at room temperature, target proteins were detected by using primary antibodies. All membranes were incubated with chemiluminescent (Millipore) and imaging was captured by the ChemiDoc XRS system (Bio-RAD). Antibodies used were listed in Table 51. Data were analyzed by AlphaEaseFC (version 4.0.0).

Immunofluorescence

Slides with cell culture was fixed for 30 min at room temperature in 95% (v/v) ethanol, washed three times in PBS and incubated with blocking buffer PBS containing 0.1% (wt/v) Triton X-100 (Sigma) and 5% (v/v) normal donkey serum (Millipore) for 60 min. Primary and secondary antibodies were diluted in blocking buffer. Primaries were incubated at 4° C. (for 24 hr) or at room temperature for 2 hr. After incubation with specific primary antibody in PBS, appropriate fluorescein isothiocyante (FITC, Invitrogen) or Alexa Fluor 488, 594, 647 (Invitrogen) or Dylight 488, 594 (BioLegend) conjugated secondary antibody was added for 1 hr at room temperature. By 4',6-diamidino-2-phenylindole (DAPI) staining, nucleus (5 min) cells were subjected for microscopy. Followed by incubation with secondary antibodies (1 hr) at room temperature and washes, slides were mounted with 50% glycerol. Images were captured on confocal laser scanning microscopy (LSM700; Zeiss Z1 or Olympus FluoView 1000 confocal laser scanning microscope) or TissueFAXS system (TissueQnostics GmbH, Vienna, Austria) and data analysed by TissueQuest software as described previously (T. T. Y. Lee, et al., PLoS ONE 7, e52491 (2012)).

TaqMan miRNA and Quantitative Real-Time PCR Assay

RNA was isolated from hTS cells in triplicate or quintuple samples using TRIZOL reagent (Invitrogen) with DNAase I on-column digestion (Qiagen, Valencia, Calif.) according to manufacturer's protocol. Total RNA (500 ng) was used for reverse transcription with iScript cDNA synthesis kit (Bio- Rad). PCR was carried out in duplicate using $\frac{1}{40}^{th}$ of the cDNA per reaction and 400 nM forward and reverse primers. For miRNA stem-loop qPCR, single tube TaqMan miRNA assays were used per manufacturer's instruction (Applied Biosystems). All RT reactions, including no-template controls and RT minus controls, were carried out in a GeneAmp PCR 9700 Thermocycler (Applied Biosystems). Comparative real-time PCR was performed in triplicate or quintuple, including no-template controls, using specific primers for miR-124 or RNU6B (Applied Biosystems). U6 snRNA (RNU6B; Applied Biosystems) served as an endogenous control. Relative expression was calculated using SDS2.2.2 software (Applied Biosystems) was used for comparative $\Delta C_t$ analysis. Sequence of primers used for betatrophin mRNA: primer 1, forward: 5'-acatctccctccccagactc-3' (SEQ ID NO:122) and reverse: 5'-tgctctgtgctcagaagtgg-3' (SEQ ID NO:123); primer 2: forward: 5'-ctgtcggctgagggtttccat-3' (SEQ ID NO:124) and reverse: 5'-gagtctggggagggagatgt-3' (SEQ ID NO:125).

Immunoprecipitation (IP) Assay

Cell lysates of bFGF-treated hTS cells were collected. By incubation with protein G-agarose (Minipore) for 30 min, total protein (100 µg) was treated with specific primary antibodies listed in (Table 51) overnight. After treating with protein G-agarose beads for 2 h, the sample was washed three times with RIPA lysis buffer (Minipore), following by adding with protein loading dye and boiled for 5 min. The sample was resolved by 8% SDS-PAGE and subjected to immunoblotting analysis.

Chromatin Immunoprecipitation (ChIP) Assay

ChIP assay was performed by using ChIP assay kit (Millipore) as manufacturer's instructions. Briefly, immunoprecipitated DNA fragments were extracted from hTS cells ($1 \times 10^6$) and antibody anti-CREB1 or anti-Oct4 or anti-β-catenin was used as described previously (T. T. Y. Lee, et al., *PLoS ONE* 7, e52491 (2012)). Specific primers were used to amplify the conserved binding site at promoter regions of miR-124a or Sox17 or Foxa2 and listed as followings:

For promoter of miR124-2: forward, 5'-tctgcggctattg-gtttca-3'(SEQ ID NO:126), and reverse, 5'-tctgccttcagca-caagagg-3'(SEQ ID NO:127); and forward, 5'-gcggctcttg-gtttcaagg-3'(SEQ ID NO:128); reverse, 5'-ctgccttcagcacaagagga-3' (SEQ ID NO:129); For promoter of miR124-3: 5'-cccgcagttctcaaggacac-3' (SEQ ID NO:130), and reverse, 5'-agaagggagccaggcaagtc-3'(SEQ ID NO:131); for promoter of Sox17: 5'-ttgtagattgctctctctcctcc-3'(SEQ ID NO:132), and reverse, 5'-gtgaagccttggctagggg-3'(SEQ ID NO:133); For promoter of Foxa2: 5'-cccatcattgattcctggat-3' (SEQ ID NO:134), and reverse, 5'-ttgggaggctgagatttgtc-3' (SEQ ID NO:135); For promoter of betatrophin: 5'-gtcagc-cctccctgactgat-3'(SEQ ID NO:136) and reverse, 5'-catgtggatttccagcctgc-3'(SEQ ID NO:137).

Dual-Luciferase Assay

To prepare the luciferase-3' UTR reporter plasmids, amplified 3'UTR fragments were amplified from genomic DNA extract of hTS cells. The 3' UTR PCR fragment was cloned into the pGL4.51 vector (Promega, Madison, Wis.) downstream of the luciferase gene by using PsiI and MfeI (Thermo Scientific, Rockford, Ill.). Primers for 3' UTR reporter construct were listed as followings:

For Cdx2 3' UTR: forward, 5'-aaattataagctgtttgggttgttg-gtct-3' (SEQ ID NO:138) and reverse, 5'-aaacaattgc-ccccataatttctgactgc-3' (SEQ ID NO:139); For Smad4 3' UTR region 1: forward, 5'-aaattataactcccaaagtgctgggatta-3' (SEQ ID NO:140) and reverse, 5'-aaacaattgctgcactgttcacag-gagga-3 (SEQ ID NO:141); For Smad4 3' UTR region 2: forward, 5'-aaattataacagttgtcccagtgctgcta-3' (SEQ ID NO:142) and reverse, 5'-aaacaattgatgacttgcccaaaggtcac-3' (SEQ ID NO:143); For GSK3β 3' UTR: forward, 5'-aaat-tataacccacaactggggtaaaaga-3' (SEQ ID NO:144) and reverse, 5'-aaacaattgctgtggaagggggcaaagata-3' (SEQ ID NO:145).

For dual luciferase assays, firefly luciferase reporter (500 ng) or empty vector without any 3'UTR co-transfected with pGL4.74 *Renilla* luciferase plasmid (500 ng; Promega), and non-specific control miRNA (30 pmol) or miR-124a precursor (30 pmol; System Biosciences, Mountain View, Calif.) were co-transfected to hTS cells ($1.5 \times 10^4$ cells in each well) using TransIT®-LT1 transfection reagent (Minis Bio LLC, Madison, Wis., US). After transfection (36 hr), the luciferase activity was analyzed by the dual luciferase reporter assay system (Promega) and the Centro LB 960 Microplate Luminometer (Berthold Technologies, Bad Wildbad, Germany). For evaluation, *renilla* luciferase value was first normalized to the firefly luciferase activity and the calculated activity of each 3'UTR reporter was further normalized to that of the control vector. Data represented as mean±SD, n=8, p<0.05 as statistic significance. Whole cell extracts prepared in the cell lysis buffer were subjected to immunoblotting with Cdx2, Smad4, GSK3β, and β-actin antibodies.

Transfection of miR-124a Precursor or Anti-miR-124a miR-124a precursor and anti-miR-124a were purchased by System Biosciences. Briefly, miR-124a precursor (60 pmol) or anti-miR-124a (60 pmol) was transfected to hTS cells in 12-well culture dishes using TransIT-LT1 transfection reagent (Minis, Madison, Wis.). Total RNAs were used for quantifying miR-124a at 36 hr after transfection.

Radioimmunoassays of C-Peptide and Insulin

In glucose stimulation test, high glucose (25 mM) was added into α-MEM media (5 ml) at over 80% confluent cells after bFGF treatment. Media were collected at different time (5, 10, 20, 30, 60 and 120 min). Collected medium was freeze dried by lyophilizer (VirTis, Warminster, Pa.) and rehydrated with sterile water (400 µl) for radioimmunoassay. C-peptide and insulin levels in the media were determined by C-PEP II-RIA-CT (DIAsource ImmunoAssays S.A. Belgium) and Coat-A-Count insulin (Siemens Healthcare Diagnostics Inc. LA, Calif.), respectively. n=5, p<0.05 as statistic significance.

Flow Cytometry

After transfection with non-specific shRNA or shRNAs against Cdx2 or Oct4 or Sox2 or Nanog, cells ($5 \times 10^6$ cells/ml) were incubated with specific primary antibodies (listed in Table 51) for 30 min. By incubation with the appropriate fluorescent dye-conjugated primary antibodies at adjusted dilution for 1 hr at 4° C., samples were washed and re-suspended in PBS followed by passing through polystyrene round-bottom tube with cell strainer cap (BD Falcon) before flow cytometry (FACScan, BD Biosciences, San Jose, Calif.). The data were analyzed with Cell-Quest software (BD Biosciences).

Transmission Electron Microscopy

After high glucose stimulation, hTS cell-derived islet-like cell mass on the culture dish was dissected with wolfram needles. For transmission electron microscopy, the clumps of cells were fixed in 0.1 M sodium cacodylate buffer (pH 7.4) containing 3% wt/vol formaldehyde, 1.5% (wt/vol) glutaraldehyde and 2.5% (wt/vol) sucrose at room temperature for 1 hr and at 4° C. overnight. The samples were washed with sodium cacodylate buffer before and after 2 hr of osmication at 4° C. in Palade's fixative containing 1% (vol/vol) $OsO_4$, treated with tannic acid, stained with uranyl acetate, dehydrated through a graded series of ethanol solutions, and embedded in TABB epoxy resin (Agar Scientific Ltd.). Ultrathin sections were stained with uranyl acetate and lead citrate, and examined using JEM-2000 EXII (JEOL, Tokyo). Imaging of vesicle granules was referred to the previously described (K. A. D'Amour, et al., *Nat. Biotech.* 23, 1534-1541 (2005)).

Statistical Analysis

All of the experiments were conducted in triplicate and repeated two times or as indicated. Data obtained from western blots, qPCR, luciferase assay, and flow cytometry were calculated by Student's t-test. p-value<0.05 was considered statistically significant.

TABLE S1

Antibodies Used in This Study

| Target | Manufacture | Code no. | WB | Flow | IF |
|---|---|---|---|---|---|
| FGFR1 | Abcam | ab10646 | 1/400 | | 1/200 |
| Mixl1 | Abcam | ab57854 | 1/1000 | | 1/200 |
| Smad4 | Santa Cruz Biotechnology | sc-7966 | 1/200 | | |
| Cdx2 | Abcam | Ab76541 | 1/1000 | | 1/200 |
| | Cell signaling | 3977s | 1/1000 | | |
| | BD Pharmingen | 560395 | | 1/40 | |
| Oct4 | Abcam | Ab19857 | 5 µg/ml | | 1 µg/ml |
| | Millpore | MAB4419 | 2 µg/ml | 1/40 | 1/200 |
| | BD Pharmingen | 560794 (Cy 5.5) | | 1/40 | |
| Nanog | Chemicon | AB9220 | 1/1000 | | 1/200 |
| | Cell signaling | 3580s | 1/1000 | | 1/200 |
| | BD Pharmingen | 560791 | | 1/40 | |
| Sox2 | Epitomics | 2683s | 1/1000 | | |
| | Abcam | Ab59776 | 1/1000 | | 1/200 |
| | BD Pharmingen | 560291 (PE) | | 1/40 | |
| C-peptide | Abcam | Ab14181 | 1/100 | | 1/50 |
| | Santa Cruz Biotechnology | Sc-51647 | 1/100 | | 1/50 |
| β-actin | Santa Cruz Biotechnology | Sc-130065 | 1/2000 | | |
| Somato-statin | Santa Cruz Biotechnology | Sc-55565 | 1/200 | | 1/100 |
| Glut2 | Chemicon | AB1342 | | | 1/100 |
| Glucagon | Santa Cruz Biotechnology | Sc-13091 | 1/200 | | 1/100 |
| Insulin | Santa Cruz Biotechnology | sc-7839 | 1/100 | | 1/50 |

TABLE S1-continued

Antibodies Used in This Study

| Target | Manufacture | Code no. | WB | Flow | IF |
|---|---|---|---|---|---|
| Ngn3 | Santa Cruz Biotechnology | sc-25654 | 1/200 | | 1/100 |
| Amylase | Santa Cruz Biotechnology | sc-12821 | 1/200 | | 1/100 |
| Pancreatic polypeptide | Chemicon | sc-80494 | | | 1/100 |
| Pdx1 | BD Pharmingen | 562160 | 1/2000 | | 1/200 |
| | Cell signaling | 5679 | 1/1000 | | 1/200 |
| PI3K | Cell signaling | 4249s | 1/1000 | | |
| p-Akt (Ser473) | Cell signaling | 4058 | 1/1000 | | |
| Akt | Cell signaling | 4685 | 1/1000 | | |
| CREB1 | Cell signaling | 9197 | 1/1000 | | |
| p-CREB1 (Ser1330) | Cell signaling | 9191 | 1/1000 | | |
| β-catenin | Cell signaling | 9587 | 1/1000 | | |
| | Epitomics | 1247-1 | 1/200 | | |
| GSK3β | Cell signaling | 9315 | 1/1000 | | |
| p-GSK3β (Ser9) | Cell signaling | 9336 | 1/500 | | |
| GSK-3α/β (Tyr-279/Tyr-216) | ECM Biosciences | GM1321 | 1/500 | | |
| GSC | Abcam | ab117871 | 1/500 | | 1/100 |
| Brachyury | Abcam | Ab20680 | 1/1000 | | 1/200 |
| Sox17 | Origene | TA502483 | 1/200 | | 1/100 |
| Foxa2 | Abcam | Ab40874 | | | |
| Hnf1b | Abcam | ab59118 | 1/1000 | | 1/200 |
| Sox9 | Abcam | ab26414 | 1 µg/ml | | 1/200 |
| Ptf1a | Abcam | ab57257 | 1/500 | | 1/200 |
| Nkx6.1 | Abcam | ab90716 | 1 µg/ml | | 5 µg/ml |
| GATA4 | Abcam | ab84593 | 1/1000 | | 1/200 |
| Nkx2.2 | Abcam | An79916 | 1/1000 | | 1/200 |

One or more embodiments, instances, or aspects disclosed herein can be combined with any other embodiment(s), instance(s), or aspect(s) disclosed herein when suitable.

While some embodiments have been shown and described herein, such embodiments are provided by way of example only. Numerous variations, changes, and substitutions can occur without departing from the inventions. It should be understood that various alternatives to the embodiments of the inventions described herein can be employed in practicing the inventions.

What is claimed is:

1. A method of differentiating an isolated mammalian trophoblast stem cell, the method comprising contacting the isolated mammalian trophoblast stem cell with bFGF (basic fibroblast growth factor), 2-mercaptoethanol and nicotinamide, to induce differentiation of the isolated mammalian trophoblast stem cell to a pancreatic progenitor cell that expresses a marker selected from the group consisting of Ngn3, insulin, and a combination thereof, wherein the isolated mammalian trophoblast stem cell is from a human or a mouse.

2. The method of claim 1, wherein the isolated mammalian trophoblast stem cell is a human trophoblast stem cell (hTS cell).

3. The method of claim 1, wherein the method activates miR-124.

4. The method of claim 1, wherein the concentration of bFGF is no more than 100 ng/mL.

5. The method of claim 1, wherein the concentration of bFGF is from about 1 to about 100 ng/mL.

6. The method of claim 1, wherein the concentration of bFGF is about 10 ng/mL.

7. The method of claim 1, wherein the concentration of 2-mercaptoethanol is from about 0.1 to about 10 mmol/L.

8. The method of claim 7, wherein the concentration of 2-mercaptoethanol is about 1 mmol/L.

9. The method of claim 1, wherein the concentration of nicotinamide is from about 1 to about 100 mmol/L.

10. The method of claim 9, wherein the concentration of nicotinamide is about 10 mmol/L.

11. The method of claim 3, wherein the miR-124 is miR-124a.

12. The method of claim 3, wherein the miR-124 is *homo sapiens* miR-124a (hsa-miR-124a).

13. The method of claim 3, wherein the miR-124 is hsa-miR-124-5p (SEQ ID NO:1: CGUGUUCACAGCGGACCUUGAU) or a fragment thereof; or hsa-miR-124-3p (SEQ ID NO:2: UAAGGCACGCGGUGAAUGCC) or a fragment thereof.

14. The method of any one of claim 1, 2, 3, 4-6, or 7-13, wherein the pancreatic progenitor cell expresses Ngn3.

* * * * *